(12) United States Patent
Haystead et al.

(10) Patent No.: US 9,738,643 B2
(45) Date of Patent: Aug. 22, 2017

(54) SUBSTITUTED INDAZOLES FOR TARGETING HSP90

(71) Applicant: Duke University, Durham, NC (US)

(72) Inventors: Timothy Haystead, Chapel Hill, NC (US); Philip Floyd Hughes, Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/419,965

(22) PCT Filed: Mar. 14, 2013

(86) PCT No.: PCT/US2013/031614
§ 371 (c)(1),
(2) Date: Feb. 6, 2015

(87) PCT Pub. No.: WO2014/025395
PCT Pub. Date: Feb. 13, 2014

(65) Prior Publication Data
US 2015/0191471 A1 Jul. 9, 2015

Related U.S. Application Data

(60) Provisional application No. 61/680,107, filed on Aug. 6, 2012.

(51) Int. Cl.
| | | |
|---|---|---|
| C07D 231/54 | (2006.01) | |
| C07D 473/34 | (2006.01) | |
| C07D 405/14 | (2006.01) | |
| G01N 33/569 | (2006.01) | |
| G01N 33/574 | (2006.01) | |
| C07D 413/12 | (2006.01) | |
| C07D 473/24 | (2006.01) | |
| C07D 487/04 | (2006.01) | |
| C07D 493/10 | (2006.01) | |

(52) U.S. Cl.
CPC ......... *C07D 473/34* (2013.01); *C07D 231/54* (2013.01); *C07D 405/14* (2013.01); *C07D 413/12* (2013.01); *C07D 473/24* (2013.01); *C07D 487/04* (2013.01); *C07D 493/10* (2013.01); *G01N 33/56988* (2013.01); *G01N 33/574* (2013.01); *G01N 33/57496* (2013.01); *G01N 2333/47* (2013.01)

(58) Field of Classification Search
CPC .................................................. C07D 231/54
USPC ...................................................... 548/360.1
See application file for complete search history.

(56) References Cited

U.S. PATENT DOCUMENTS

| | | | |
|---|---|---|---|
| 5,260,291 A | 11/1993 | Lunt et al. | |
| 5,747,498 A | 5/1998 | Schnur et al. | |
| 7,344,699 B2 | 3/2008 | Lappin et al. | |
| 7,358,370 B2 | 4/2008 | Huang et al. | |
| 7,612,201 B2 | 11/2009 | Beswick et al. | |
| 7,678,803 B2 | 3/2010 | Huang et al. | |
| 7,906,529 B2 | 3/2011 | Huang et al. | |
| 7,928,135 B2 | 4/2011 | Huang et al. | |
| 2007/0207984 A1 | 9/2007 | Huang et al. | |
| 2008/0139587 A1 | 6/2008 | Huang et al. | |
| 2008/0269193 A1 | 10/2008 | Huang et al. | |
| 2009/0179638 A1 | 7/2009 | Barker et al. | |
| 2009/0226431 A1 | 9/2009 | Habib | |
| 2009/0298857 A1 | 12/2009 | Chiosis et al. | |
| 2011/0065198 A1 | 3/2011 | Friebe et al. | |
| 2011/0183977 A1 | 7/2011 | Huang et al. | |
| 2014/0079636 A1 | 3/2014 | Chimmanamada et al. | |
| 2015/0139905 A1 | 5/2015 | Chimmanamada et al. | |

FOREIGN PATENT DOCUMENTS

| | | |
|---|---|---|
| EP | 0520722 | 12/1992 |
| EP | 0564409 | 10/1993 |
| EP | 0566226 | 10/1993 |
| EP | 0787722 | 8/1997 |
| EP | 0837063 | 4/1998 |

(Continued)

OTHER PUBLICATIONS

Leamon et al. "Folate-targeted chemotherapy," Advanced Drug Delivery Reviews, 56, p. 1127-1141, 2004.

(Continued)

*Primary Examiner* — Douglas M Willis
(74) *Attorney, Agent, or Firm* — Michael Best & Friedrich LLP

(57) ABSTRACT

Described herein are substituted indazoles that may selectively bind to Hsp90, methods of using the compounds, and kits including the compounds. The compounds may include detection moieties such as fluorophores that may allow for selective detection of Hsp90 in a sample. Suitable compounds include those of formula (II):

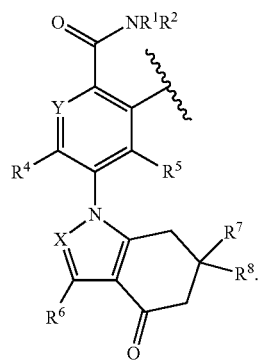

10 Claims, 23 Drawing Sheets

(56) References Cited

FOREIGN PATENT DOCUMENTS

| WO | WO 96/33980 | 10/1996 |
|---|---|---|
| WO | WO 97/02266 | 1/1997 |
| WO | WO 97/30034 | 8/1997 |
| WO | WO 97/38983 | 10/1997 |
| WO | WO 97/49688 | 12/1997 |
| WO | WO 98/10767 | 3/1998 |
| WO | WO 99/03854 | 1/1999 |
| WO | WO 02/22577 | 3/2002 |
| WO | WO 03/013541 | 2/2003 |
| WO | WO 2006/084030 | 8/2006 |
| WO | WO 2008/130879 | 10/2008 |
| WO | 2011/116181 | 9/2011 |
| WO | 2012/045237 | 4/2012 |
| WO | WO 2014/025395 | 2/2014 |

OTHER PUBLICATIONS

Koga et al., "Inhibition of Cancer Invasion and Metastasis by Targeting the Molecular Chaperone Heat-shock Protein 90," Anticancer Research 29, p. 797-808, 2009.
Wang et al. "Sta-9090, a small-molecule Hsp90 inhibitor for the potential treatment of cancer," Current Opinion in Investigational Drugs 11 (12), p1466-1476, 2010.
Barrott et al., "Optical and radioiodinated tethered Hsp90 inhibitors reveal selective internalization of ectopic Hsp90 in malignant breast tumor cells," Chem. Biol., 2013, 20(9):1187-97.
Bulinski, "Overexpression of MAP4 inhibits organelle motility and trafficking in vivo," J. Cell Sci., 1997, 110:3055-3064.
Caldas-Lopes et al., "Hsp90 inhibitor PU-H71, a multimodal inhibitor of malignancy, induces complete responses in triple-negative breast cancer models," Proc Natl Acad Sci U S A, 2009, 106(20):8368-73.
Chandarlapaty et al., "SNX2112, a synthetic heat shock protein 90 inhibitor, has potent antitumor activity against HER kinase-dependent cancers," Cancer Res., 2008, 14(1) 240.
Chun et al., "Regiospecific Syntheses of Functionalized Diaryliodonium Tosylates via [Hydroxy(tosyloxy)iodo]arenes Generated in Situ from (Diacetoxyiodo)arenes," J. Org. Chem., 2012, 77, 1931-1938.
Graves et al., "Discovery of novel targets of quinoline drugs in the human purine binding proteome," Mol. Pharmacol., 2002, 62(6):1364.
Huang et al., "Discovery of novel 2-aminobenzamide inhibitors of heat shock protein 90 as potent, selective and orally active antitumor agents," J. Med. Chem., 2009, 52(14):4288.
Hughes et al., "A highly selective Hsp90 affinity chromatography resin with cleavable linker," Bioorganic & Medicinal Chemistry 20, 2012, 3298-3305.
Koziorowski et al., "A new convenient route to radioiodinated N-succinimidyl 3- and 4-iodobenzoate, two reagents for radioiodination of proteins," Appl. Radiat. Isot., 1998, vol. 49, No. 8, pp. 955-959.
Muhlradt et al., "Epothilone B stabilizes microtubuli of macrophages like taxol without showing taxol-like endotoxin activity," Cancer Res., 1997, 57:3344-3346.
Nicolaou et al., "Synthesis of epothilones A and B in solid and solution phase," Nature, 1997, 387:268-272.
Panda et al., "Differential Effects of Vinblastine on Polymerization and Dynamics at Opposite Microtubule Ends," J. Biol. Chem., 1996, 271:29807-29812.
Panda, "Stabilization of microtubule dynamics by estramustine by binding to a novel site in tubulin: A possible mechanistic basis for its antitumor action," Proc. Natl. Acad. Sci. USA, 1997, 94:10560-10564.
Schulte et al., "The benzoquinone ansamycin 17-allylamino-17-demethoxygeldanamycin binds to Hsp90 and shares important biologic activities with geldanamycin," Cancer Chemoth. Pharm., 1998, 42(4) 273.
Taldone et al., "Design, synthesis, and evaluation of small molecule Hsp90 probes," Bioorganic & Medicinal Chemistry 19, 2011, 2603-2614.
Taldone et al., "Synthesis of purine-scaffold fluorescent probes for heay shock protein 90 with use in flow cytometry and fluorescence microscopy," Bioorganic & Medicinal Chemistry Letters 21, 2011, 5347-5352.
Vasquez, "Nanomolar concentrations of nocodazole alter microtubule dynamic instability in vivo and in vitro," Mol. Biol. Cell., 1997, 8:973-985.
Zagouri et al., "Hsp90 in the continuum of breast ductal carcinogenesis: Evaluation in precursors, preinvasive and ductal carcinoma lesions," BMC Cancer, 2010, 10:353.
International Search Report and Written Opinion for Application No. PCT/US2013/031614 dated May 23, 2013 (18 pages).
Extended European Search Report for Application No. 13828368.4 dated Apr. 26, 2016 (12 pages).
Extended European Examination Report for Application No. 13828368.4 dated Mar. 16, 2017 (4 pages).

SUBSTITUTED INDAZOLES FOR TARGETING HSP90

CROSS-REFERENCE TO RELATED APPLICATIONS

This patent application is a national stage filing under 35 U.S.C. 371 of International Patent Application No. PCT/US2013/031614, filed Mar. 14, 2013, which claims priority to U.S. Provisional Patent Application No. 61/680,107, filed Aug. 6, 2012, the entire contents of which are incorporated by reference in their entireties.

STATEMENT REGARDING FEDERALLY SPONSORED RESEARCH

This invention was made with U.S. Government support awarded by the National Institutes of Health, Grant Nos. 1R01-AI089526-01 and 1R01-AI090644-01. The U.S. Government has certain rights in this invention.

BACKGROUND

Heat shock protein 90 (Hsp90), one of the most abundant proteins expressed in cells, regulates cellular homeostasis by chaperoning protein folding and trafficking. Hsp90 is also highly upregulated in response to stress. The N-terminal domain of Hsp90 includes an ATP binding site, and ATPase activity is necessary for all of its cellular functions. To date, over 200 Hsp90 "client" proteins have been identified and many of these are involved in signal transduction.

Hsp90 has been implicated in diseases such as cancer, and its expression is up-regulated during oncogenesis. High expression is associated with poor prognosis for cancers, such as breast cancer, prostate cancer, non-small cell lung cancer, colorectal cancer and melanoma.

Proteins such as glucose-regulated protein 94 (GRP94) and tumor necrosis factor receptor-associated protein (TRAP1) share homology with Hsp90 and both proteins also possess ATPase activity. While inhibitors of Hsp90 have been shown to have antiproliferative and antitumor activities, current Hsp90 inhibitors may bind nonspecifically to GRP94 and TRAP1. There is a need for compounds that selectively bind to Hsp90.

SUMMARY

In one aspect, the disclosure provides a compound of formula (I):

$$A\text{-}X^1\text{-}L\text{-}X^2\text{---}B \qquad (I)$$

wherein:
A is an Hsp90 binding component;
$X^1$ is selected from the group consisting of —NH—, —O—, —S—, —C(O)— and —S(O)$_2$—;
$X^2$ is selected from the group consisting of —NR—, —O—, —S—, —C(O)— and —S(O)$_2$—
L is a divalent linker comprising at least twelve member atoms independently selected from carbon, nitrogen and oxygen, wherein at least one member atom is nitrogen or oxygen;
B is selected from the group consisting of a detection moiety, an anti-cancer agent, and an Hsp90 binding component; and
R is selected from the group consisting of hydrogen and a detection moiety.

In another aspect, the disclosure provides a method of detecting Hsp90 in a sample, comprising:
a) contacting the sample with a compound having the following formula (Ia):

$$A\text{-}X^1\text{-}L\text{-}X^2\text{---}B \qquad (Ia)$$

wherein:
A is an Hsp90 binding component;
$X^1$ is selected from the group consisting of —NH—, —O—, —S—, —C(O)— and —S(O)$_2$—;
$X^2$ is selected from the group consisting of —NR—, —O—, —S—, —C(O)— and —S(O)$_2$—;
L is a divalent linker comprising at least twelve member atoms independently selected from carbon, nitrogen and oxygen, wherein at least one member atom is nitrogen or oxygen;
B is a detection moiety; and
R is selected from the group consisting of hydrogen and a detection moiety; and
b) detecting a signal from the detection moiety.

In another aspect, the disclosure provides a method of detecting cancer in a subject, comprising:
a) contacting a biological sample from the subject with a compound having the following formula (Ia):

$$A\text{-}X^1\text{-}L\text{-}X^2\text{---}B \qquad (Ia)$$

wherein:
A is an Hsp90 binding component;
$X^1$ is selected from the group consisting of —NH—, —O—, —S—, —C(O)— and —S(O)$_2$—;
$X^2$ is selected from the group consisting of —NR—, —O—, —S—, —C(O)— and —S(O)$_2$—;
L is a divalent linker comprising at least twelve member atoms independently selected from carbon, nitrogen and oxygen, wherein at least one member atom is nitrogen or oxygen;
B is a detection moiety; and
R is selected from the group consisting of hydrogen and a detection moiety; and
b) detecting a signal from the detection moiety;
wherein cancer is detected in the sample when the signal from the detection moiety is higher relative to a signal from a reference sample.

In another aspect, the disclosure provides a method of treating cancer in a subject in need of treatment, comprising administering the subject a therapeutically effective amount of a compound having the following formula (Ib):

$$A\text{-}X^1\text{-}L\text{-}X^2\text{---}B \qquad (Ib)$$

wherein:
A is an Hsp90 binding component;
$X^1$ and $X^2$ are each independently selected from the group consisting of —NH—, —O—, —S—, —C(O)— and —S(O)$_2$—;
L is a divalent linker comprising at least twelve member atoms independently selected from carbon, nitrogen and oxygen, wherein at least one member atom is nitrogen or oxygen; and
B is selected from the group consisting of an anti-cancer agent and an Hsp90 binding component.

In another aspect, the disclosure provides a method of detecting Human Immunodeficiency Virus (HIV) in a subject, the method comprising:
a) contacting a biological sample from the subject with a compound having the following formula (Ia):

$$A\text{-}X^1\text{-}L\text{-}X^2\text{---}B \qquad (Ia)$$

wherein:
A is an Hsp90 binding component;
X¹ is selected from the group consisting of —NH—, —O—, —S—, —C(O)— and —S(O)₂—;
X² is selected from the group consisting of —NR—, —O—, —S—, —C(O)— and —S(O)₂—;
L is a divalent linker comprising at least twelve member atoms independently selected from carbon, nitrogen and oxygen, wherein at least one member atom is nitrogen or oxygen;
B is a detection moiety; and
R is selected from the group consisting of hydrogen and a detection moiety; and
b) detecting a signal from the detection moiety;
wherein HIV is detected in the sample when the signal from the detection moiety is higher relative to a signal from a reference sample.

In another aspect, the disclosure provides a pharmaceutical composition comprising a compound of formula (Ib):

A-X¹-L-X²—B          (Ib)

wherein:
A is an Hsp90 binding component;
X¹ and X² are each independently selected from the group consisting of —NH—, —O—, —S—, —C(O)— and —S(O)₂—;
L is a divalent linker comprising at least twelve member atoms independently selected from carbon, nitrogen and oxygen, wherein at least one member atom is nitrogen or oxygen; and
B is selected from the group consisting of an anti-cancer agent and an Hsp90 binding component;
and a pharmaceutically acceptable carrier.

In another aspect, the disclosure provides a kit comprising a compound of formula (I) as described herein.

Other aspects and embodiments will become apparent in light of the following description and drawings.

DETAILED DESCRIPTION

Figure 1:
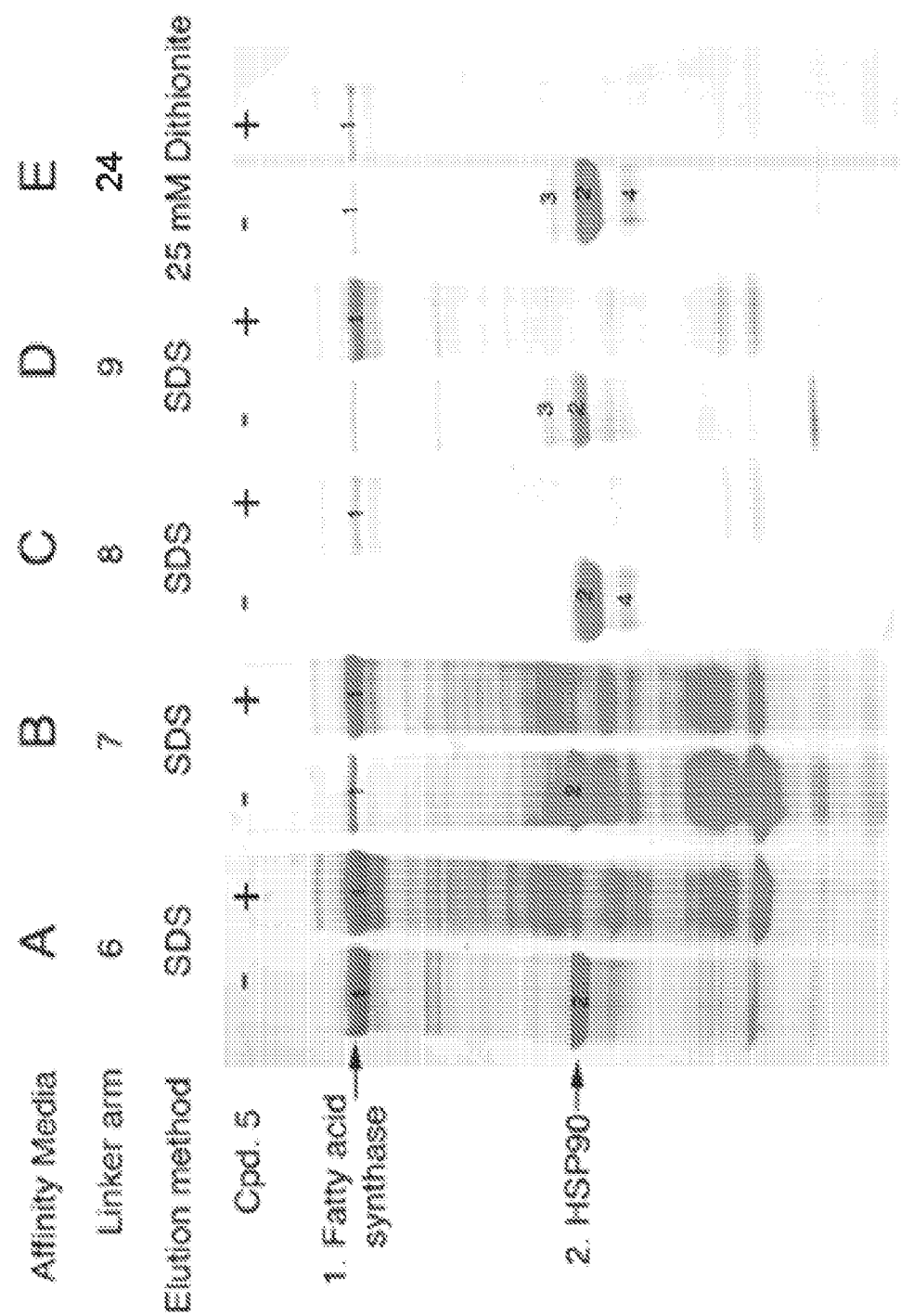
FIG. 1 is an SDS-PAGE silver stain showing the effect of different linker structures on Hsp90 recovery and recovery of non-specifically bound proteins. Selectivity towards Hsp90 was demonstrated by including 1 mM compound 5 in the tissue extract prior to mixing.

Described herein are compounds that may selectively bind to Hsp90. The compounds include an Hsp90 binding component, a linker, and an active moiety such as a detection group (e.g., a fluorophore or a radioisotope), an anti-cancer agent, or a second Hsp90 binding component. The compounds described herein may selectively bind to Hsp90 and may have significantly higher affinities for Hsp90 than for proteins with homology to Hsp90, such as GRP94 and TRAP1. The selective nature of the compounds may make them useful probes of Hsp90 in samples, and may allow for the selective targeting of Hsp90. For example, compounds described herein may be used to selectively detect Hsp90 in samples, and to selectively deliver anti-cancer agents to cells expressing high levels of Hsp90.

1. DEFINITIONS

The terminology used herein is for the purpose of describing particular embodiments only and is not intended to be limiting. As used in the specification and the appended claims, the singular forms "a," "and" and "the" include plural references unless the context clearly dictates otherwise.

Section headings as used in this section and the entire disclosure herein are not intended to be limiting.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such values are thus encompassed by the scope of the claims reciting the terms "about" and "approximately."

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Contacting" as used herein, e.g., as in "contacting a sample" refers to contacting a sample directly or indirectly in vitro, ex vivo, or in vivo (i.e. within a subject as defined herein). Contacting a sample may include addition of a compound to a sample (e.g., a sample comprising cells that contain Hsp90), or administration to a subject. Contacting encompasses administration to a solution, cell, tissue, mammal, subject, patient, or human. Further, contacting a cell includes adding an agent to a cell culture.

"Detection moiety" as used herein includes one or more groups that are detectable, either directly or indirectly, by methods such as spectroscopic, photochemical, biochemical, chemical, or other methods. For example, useful detectable moieties or labels include chromophores, fluorophores, biotin, radioactive compounds, and the like. The detection moiety often generates a measurable signal, such as a radioactive, chromogenic, luminescent, or fluorescent signal, which can be used to quantitate the amount of the detection moiety in a sample. In some embodiments a detection moiety may include more than one detectable group, e.g., a fluorophore and a radioactive moiety.

"Effective amount," as used herein, refers to a dosage or an amount of a compound or a composition effective for eliciting a desired effect. This term as used herein may also refer to an amount effective at bringing about a desired in vivo effect in an animal, e.g., a mammal, e.g., a human. For example, in methods of treating cancer, an effective amount may be an amount sufficient to treat the disorder.

"Member atom" as used herein refers to a polyvalent atom (e.g., a C, O, N, or S atom) in a chain or ring system that constitutes a part of the chain or ring. For example, in pyridine, five carbon atoms and one nitrogen atom are member atoms of the ring. In diethyl ether, four carbon atoms and one oxygen atom are member atoms of the chain. Member atoms will be substituted up to their normal valence. For example, in pyridine, the five carbon atoms will each be further substituted with a hydrogen or another substituent.

As used herein, the term "subject" is intended to include human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is cured, healed, alleviated, relieved, altered, remedied, ameliorated, or improved. Treating includes administering an amount effective to alleviate, relieve, alter, remedy, ameliorate, cure, improve or affect the disorder or the symptoms of the disorder. The treatment may inhibit deterioration or worsening of a symptom of a disorder.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a straight or branched saturated hydrocarbon chain. Alkyl groups may include a specified number of carbon atoms. For example, $C_1$-$C_{12}$ alkyl indicates that the alkyl group may have 1, 2, 3, 4, 5, 6, 7, 8, 9, 10, 11 or 12 carbon atoms. An alkyl group may be, e.g., a $C_1$-$C_{12}$ alkyl group, a $C_1$-$C_{10}$ alkyl group, a $C_1$-$C_8$ alkyl group, a $C_1$-$C_6$ alkyl group or a $C_1$-$C_4$ alkyl group. For example, exemplary $C_1$-$C_4$ alkyl groups include methyl, ethyl, n-propyl, isopropyl, n-butyl, sec-butyl, isobutyl and tert-butyl groups. An alkyl group may be optionally substituted with one or more substituents.

The term "alkylenyl" refers to a divalent alkyl group, examples of which include but are not limited to —CH$_2$—, —CH$_2$CH$_2$—, —CH$_2$CH$_2$CH$_2$— and —CH$_2$CH(CH$_3$)CH$_2$—. An alkylenyl group may be optionally substituted with one or more substituents.

The term "alkenyl" refers to a straight or branched hydrocarbon chain having one or more double bonds. Alkenyl groups may include a specified number of carbon atoms. For example, $C_2$-$C_{12}$ alkenyl indicates that the alkenyl group may have 2, 3, 4, 5, 6, 7, 8, 9, 10, 11 or 12 carbon atoms. An alkenyl group may be, e.g., a $C_2$-$C_{12}$ alkenyl group, a $C_2$-$C_{10}$ alkenyl group, a $C_2$-$C_8$ alkenyl group, a $C_2$-$C_6$ alkenyl group or a $C_2$-$C_4$ alkenyl group. Examples of alkenyl groups include but are not limited to allyl, propenyl, 2-butenyl, 3-hexenyl and 3-octenyl groups. One of the double bond carbons may optionally be the point of attachment of the alkenyl substituent. An alkenyl group may be optionally substituted with one or more substituents.

The term "alkenylenyl" refers to a divalent alkenyl group, examples of which include but are not limited to —CH=CH—, —CH=CH—CH$_2$—, —CH=CH—CH$_2$—CH$_2$— and —CH$_2$—CH=CH—CH$_2$—. An alkenylenyl group may be optionally substituted with one or more substituents.

The term "alkynyl" refers to a straight or branched hydrocarbon chain having one or more triple bonds. Alkynyl groups may include a specified number of carbon atoms. For example, $C_2$-$C_{12}$ alkynyl indicates that the alkynyl group may have 2, 3, 4, 5, 6, 7, 8, 9, 10, 11 or 12 carbon atoms. An alkynyl group may be, e.g., a $C_2$-$C_{12}$ alkynyl group, a $C_2$-$C_{10}$ alkynyl group, a $C_2$-$C_8$ alkynyl group, a $C_2$-$C_6$ alkynyl group or a $C_2$-$C_4$ alkynyl group. Examples of alkynyl groups include but are not limited to ethynyl, propargyl, and 3-hexynyl. One of the triple bond carbons may optionally be the point of attachment of the alkynyl substituent. An alkynyl group may be optionally substituted with one or more substituents.

The term "alkynylenyl" refers to a divalent alkynyl group, examples of which include but are not limited to —C≡C—, —C≡C—CH$_2$—, —C≡C—CH$_2$—CH$_2$— and —CH$_2$—C≡C—CH$_2$—. An alkynylenyl group may be optionally substituted with one or more substituents.

The term "aryl" refers to an aromatic monocyclic, bicyclic, or tricyclic hydrocarbon ring system, wherein any ring atom capable of substitution can be substituted (e.g., with one or more substituents). Examples of aryl moieties include but are not limited to phenyl, naphthyl, and anthracenyl. Aryl groups may be optionally substituted with one or more substituents.

The term "arylalkyl" refers to an alkyl moiety in which at least one alkyl hydrogen atom is replaced with an aryl group. Arylalkyl includes groups in which more than one hydrogen atom has been replaced with an aryl group. Examples of arylalkyl groups include but are not limited to benzyl, 2-phenylethyl, 3-phenylpropyl, 9-fluorenyl, benzhydryl, and trityl groups. Arylalkyl groups may be optionally substituted with one or more substituents, on either the aryl moiety or the alkyl moiety.

The term "cycloalkyl" as used herein refers to nonaromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include but are not limited to cyclopropyl, cyclobutyl, cyclopentyl, cyclohexyl, cyclohexenyl, cyclohexadienyl, methylcyclohexyl, adamantyl, norbornyl, norbornenyl, tetrahydronaphthalenyl and dihydroindenyl. Cycloalkyl groups may be optionally substituted with one or more substituents.

The term "cycloalkylalkyl", as used herein, refers to an alkyl group in which at least one hydrogen atom is replaced with a cycloalkyl group. Cycloalkylalkyl groups include those in which more than one hydrogen atom of the alkyl group is replaced with a cycloalkyl group. Examples of cycloalkylalkyl groups include but are not limited to cyclohexylmethyl, cyclopentylmethyl, cyclobutylmethyl and cyclopropylmethyl. Cycloalkylalkyl groups can be optionally substituted with one or more substituents, on either the cycloalkyl moiety or the alkyl moiety.

The term "halo" or "halogen" as used herein refers to any radical of fluorine, chlorine, bromine or iodine.

The term "haloalkyl" as used herein refers to an alkyl group as defined herein, in which one or more hydrogen atoms are replaced with halogen atoms, and includes alkyl moieties in which all hydrogens have been replaced with halogens (e.g., perfluoroalkyl such as CF$_3$).

"Heteroalkyl" refers to an alkyl, alkenyl or alkynyl group as defined herein, wherein at least one carbon atom of the alkyl group is replaced with a heteroatom. Heteroalkyl groups may contain from 1 to 18 non-hydrogen atoms (carbon and heteroatoms) in the chain, or 1 to 12 atoms, or 1 to 6 atoms, or 1 to 4 atoms. Heteroalkyl groups may be straight or branched, and saturated or unsaturated. Unsaturated heteroalkyl groups have one or more double bonds and/or one or more triple bonds. Heteroalkyl groups may be unsubstituted or substituted. Exemplary heteroalkyl groups include but are not limited to alkoxyalkyl (e.g., methoxymethyl), and aminoalkyl (e.g., alkylaminoalkyl and dialkylaminoalkyl). Heteroalkyl groups may be optionally substituted with one or more substituents.

The term "heteralkylenyl" refers to a divalent heteroalkyl group, examples of which include but are not limited to —CH$_2$OCH$_2$—, —CH$_2$NHCH$_2$—, polyethyleneglycol groups (e.g., —(CH$_2$CH$_2$O)$_n$—), polyethyleneimine groups (e.g., —(CH$_2$CH$_2$NH)$_n$—), and the like. A heteroalkylenyl group may be optionally substituted with one or more substituents.

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include but are not limited to radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines. Heteroaryl groups may be optionally substituted with one or more substituents.

The term "heteroarylalkyl" refers to an alkyl moiety in which at least one alkyl hydrogen atom is replaced with a heteroaryl group. Heteroarylalkyl includes groups in which more than one hydrogen atom has been replaced with a heteroaryl group. Examples of heteroarylalkyl groups include but are not limited to imidazolylmethyl (e.g., 1H-imidazol-2-ylmethyl and 1H-imidazol-4-ylmethyl), pyridinylmethyl (e.g., pyridin-3-ylmethyl and pyridin-4-ylmethyl), pyrimidinylmethyl (e.g., pyrimidin-5-ylmethyl), furylmethyl (e.g., fur-2-ylmethyl and fur-3-ylmethyl), and thienylmethyl (e.g., thien-2-ylmethyl and thien-3-ylmethyl) groups. Heteroarylalkyl groups may be optionally substituted with one or more substituents, on either the heteroaryl moiety or the alkyl moiety.

The term "heteroatom", as used herein, refers to a non-carbon or hydrogen atom such as a nitrogen, sulfur, oxygen, silicon or phosphorus atom. Groups containing more than one heteroatom may contain different heteroatoms.

The term "heterocyclyl", as used herein, refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include but are not limited to radicals of tetrahydrofuran, tetrahydrothiophene, tetrahydropyran, oxetane, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like. Heterocyclyl groups may be optionally substituted with one or more substituents.

The term "heterocyclylalkyl" refers to an alkyl moiety in which at least one alkyl hydrogen atom is replaced with a heterocyclyl group. Heterocyclylalkyl includes groups in which more than one hydrogen atom has been replaced with a heterocyclyl group. Examples of heterocyclylalkyl groups include but are not limited to oxetanylmethyl, morpholinomethyl, and pyrrolidinylmethyl groups, and the like. Heterocyclylalkyl groups may be optionally substituted with one or more substituents, on either the heterocyclyl moiety or the alkyl moiety.

The term "hydroxy" refers to an —OH radical. The term "alkoxy" refers to an —O— alkyl radical. The term "aryloxy" refers to an —O-aryl radical.

The term "oxo" refers to an oxygen atom, which forms a carbonyl when attached to carbon, an N-oxide when attached to nitrogen, and a sulfoxide or sulfone when attached to sulfur (i.e. =O).

The term "mercapto" or "thiol" refers to an —SH radical. The term "thioalkoxy" or "thioether" refers to an —S-alkyl radical. The term "thioaryloxy" refers to an —S-aryl radical.

The term "substituents" refers to a group "substituted" on an alkyl, alkenyl, alkynyl, cycloalkyl, heterocyclyl, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In embodiments, substituents on a group are independently any one single, or any combination of the aforementioned substituents. In embodiments, a substituent may itself be substituted with any one of the above substituents.

The above substituents may be abbreviated herein. For example, the abbreviations Me, Et, Ph and Bn represent methyl, ethyl, phenyl and benzyl, respectively. A more comprehensive list of standard abbreviations used by organic chemists appears in a table entitled Standard List of Abbreviations of the Journal of Organic Chemistry. The abbreviations contained in said list are hereby incorporated by reference.

For compounds described herein, groups and substituents thereof may be selected in accordance with permitted valence of the atoms and the substituents, and such that the selections and substitutions result in a stable compound, e.g., a compound that does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulae herein to depict the bond that is the point of attachment of the moiety or substituent to the core or backbone structure.

2. COMPOUNDS

Compounds that may selectively bind to Hsp90 include compounds of formula (I):

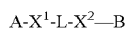          (I)

wherein:

A is an Hsp90 binding component;

$X^1$ is selected from the group consisting of —NH—, —O—, —S—, —C(O)— and —S(O)$_2$—;

$X^2$ is selected from the group consisting of —NR—, —O—, —S—, —C(O)— and —S(O)$_2$—;

L is a divalent linker comprising at least twelve member atoms independently selected from carbon, nitrogen and oxygen, wherein at least one member atom is nitrogen or oxygen;

B is selected from the group consisting of a detection moiety, an anti-cancer agent, and an Hsp90 binding component; and R is selected from the group consisting of hydrogen and a detection moiety.

Compounds that may be used in methods described herein also include compounds of formula (Ia):

          (Ia)

wherein:

A is an Hsp90 binding component;

$X^1$ is selected from the group consisting of —NH—, —O—, —S—, —C(O)— and —S(O)$_2$—;

$X^2$ is selected from the group consisting of —NR—, —O—, —S—, —C(O)— and —S(O)$_2$—;

L is a divalent linker comprising at least twelve member atoms independently selected from carbon, nitrogen and oxygen, wherein at least one member atom is nitrogen or oxygen;

B is a detection moiety; and

R is selected from the group consisting of hydrogen and a detection moiety.

Compounds that may be used in methods described herein also include compounds of formula (Ib):

          (Ib)

wherein:

A is an Hsp90 binding component;

$X^1$ and $X^2$ are each independently selected from the group consisting of —NH—, —O—, —S—, —C(O)— and —S(O)$_2$—;

L is a divalent linker comprising at least twelve member atoms independently selected from carbon, nitrogen and oxygen, wherein at least one member atom is nitrogen or oxygen; and B is selected from the group consisting of an anti-cancer agent and an Hsp90 binding component.

a. Hsp90 Binding Components

In the compounds of formula (I), A is an Hsp90 binding component. The compounds of formula (I) include at least one Hsp90 binding component, and may include two Hsp90 binding components in embodiments in which B is also an Hsp90 component. Any molecule that binds to Hsp90 can be used as the basis for the Hsp90 binding component. Based on the complete structure of the compounds of formula (I), it will be understood that the Hsp90 binding component corresponds to an Hsp90 binding compound in which an atom or a group of atoms is removed, to provide a point of attachment to the —X$^1$-L-X$^2$—B moiety of the remainder of the compound of formula (I) (or the —X$^2$-L-X$^1$-A moiety in embodiments in which B is an Hsp90 binding component).

In embodiments, an Hsp90 binding component has the following formula (II):

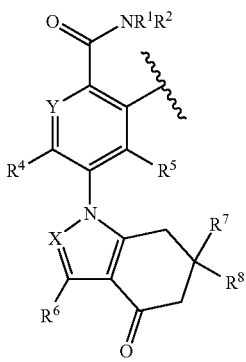
(II)

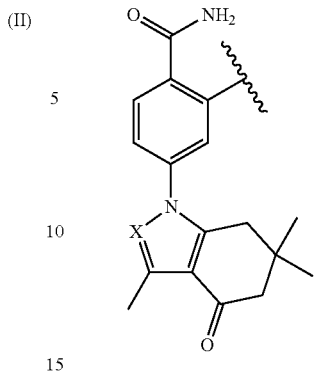

wherein:
each $Y^1$ is independently selected from the group consisting of CH and N;
R is alkylenyl or heteroalkylenyl;
each $Z^1$ is taken together with the carbon atoms to which they are attached to form a heterocyclic ring;
$Z^2$ is hydrogen or halo;
$Z^3$ is $CH_2$, S, O, or NH;
$Z^4$ is hydrogen or halo; and

represents the point of attachment to the remainder of the compound of formula (I), e.g., to the —$X^1$-L-$X^2$—B moiety, or to the $X^2$-L-$X^1$-A moiety when B is an Hsp90 binding component having the formula (III).

In embodiments, a group of formula (III) is the following:

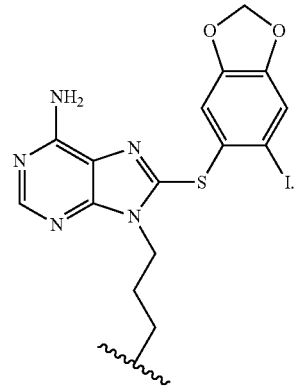

wherein:
$R^1$ and $R^2$ are independently selected from the group consisting of —H and —$C_{1-8}$-alkyl;
Y is $CR^3$ or N;
$R^3$ is —H, —F or —$OCH_3$;
$R^4$ and $R^5$ are independently selected from the group consisting of —H, —F and —$OCH_3$;
$R^6$ is —$C_{1-8}$-alkyl, —$C_{2-8}$-alkenyl, —$C_{2-8}$-alkynyl, —$C_{3-8}$-cycloalkenyl, —$C_{3-8}$-cycloalkenyl-$C_{1-8}$-alkyl, —$C_{3-8}$-cycloalkyl, —$C_{3-8}$-cycloalkyl-$C_{1-8}$-alkyl, aryl, aryl-$C_{1-8}$-alkyl, halo-$C_{1-8}$-alkyl, heteroaryl, heteroaryl-$C_{1-8}$-alkyl, heterocyclyl, heterocyclyl-$C_{1-8}$-alkyl, or hydroxy-$C_{1-8}$-alkyl;
$R^7$ and $R^8$ are independently selected from the group consisting of —H and —$C_{1-8}$-alkyl; or $R^7$ and $R^8$ taken together with the carbon atom to which they are attached form a $C_{3-8}$-cycloalkyl group;
X is N or $CR^9$; and
$R^9$ is —H or —$C_{1-8}$-alkyl; and

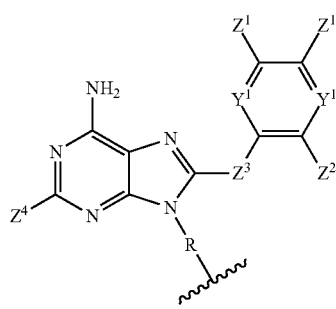
(III)

represents the point of attachment to the —$X^1$-L-$X^2$—B moiety of the compound of formula (I).

In embodiments of formula (II), $R^1$ and $R^2$ are each —H, Y is $CR^3$, $R^3$ is —H, $R^4$ and $R^5$ are each —H, $R^6$ is —$C_{1-8}$-alkyl (e.g., methyl) or halo-$C_{1-8}$-alkyl (e.g., trifluoromethyl), $R^7$ and $R^8$ are independently —$C_{1-8}$-alkyl (e.g., methyl), and X is N. In embodiments, formula (II) is the following:

In embodiments, an Hsp90 binding component has the following formula (III):

The Hsp90 binding component may comprise any known Hsp90 binding compound or a portion thereof that retains affinity for Hsp90. Other compounds that bind to Hsp90 are known in the art, and include, for example, geldanamycin, herbimycin, radicicol, deguelin, derrubone and macebecin. Other compounds that bind to Hsp90 may include but are not limited to those described in U.S. Pat. Nos. 7,358,370, 7,678,803, 7,906,529 and 7,928,135, U.S. Patent Publication No. 2011/0183977, and International Patent Publication Nos. WO2008/130879 and WO2006/084030.

b. Linker

In the compounds of formula (I), L is a divalent linker comprising at least twelve member atoms independently selected from carbon, nitrogen and oxygen, wherein at least one member atom is nitrogen or oxygen. In embodiments, L is a heteroalkylenyl group comprising at least twelve member atoms. In some embodiments, L comprises 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 atoms. In some embodiments, the heteroalkylenyl group may be optionally substituted (e.g., a carbon may be substituted with an oxo group).

In embodiments, L is a straight-chain heteroalkylenyl group. In embodiments, L includes at least one monomer of a polyethylene glycol group (i.e. —(CH$_2$CH$_2$O)—), or it may include at least two, three, four, five, six or more such monomers.

In some embodiments, L has the formula —(CH$_2$)$_m$—(OCH$_2$CH$_2$)$_n$—O—(CH$_2$)$_p$—, wherein m is 2 or 3, n is 3, 4, 5, 6, 7, 8, 9, 10, 11, 12, 13, 14, 15, 16, 17, 18, 19 or 20, and p is 2 or 3. In embodiments, m is 2. In embodiments, m is 3. In embodiments, n is 4, 5, 6, 7, 8, 9 or 10. In embodiments, n is 4. In embodiments, p is 2. In embodiments, p is 3.

A suitable linker has the following formula:

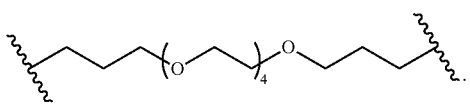

c. $X^1$ and $X^2$

The groups $X^1$ and $X^2$ in the compounds formula (I) are each independently selected from the group consisting of —NH—, O, S, C(O)— and —S(O)$_2$—. These groups serve as bridges between the linker and the A and B groups of the compound of formula (I). During the synthesis of these molecules (described in further detail below), the $X^1$ and $X^2$ groups may be derived from a linker precursor compound. For example, in some embodiments $X^1$ and $X^2$ may be —NH—. In such embodiments, a suitable linker precursor compound may have the formula H$_2$N-Linker-NH$_2$. In this case, the terminal amino groups of the linker precursor compound provide the source of the $X^1$ and $X^2$ groups.

In some embodiments, $X^2$ may be NR, wherein R is selected from the group consisting of hydrogen and a detection moiety. Such compounds may be synthesized, for example, by first synthesizing a group in which $X^2$ is NH and then further derivatizing the NH group with a compound comprising an additional detection moiety.

d. Detection Moieties

In embodiments of the compounds of formula (I), B is a detection moiety. The detection moiety comprises one or more groups that are, either directly or indirectly, detectable via a method such as a spectroscopic method. Exemplary detection moieties may comprise, for example, a chromophore, a fluorophore, a luminescent moiety or a radioisotope. In some embodiments, B comprises one or more detection moieties, such as, for example, a fluorophore and a radioisotope.

In embodiments, the detection moiety comprises a fluorophore. Suitable fluorophores include fluoresceins, rhodamines, coumarins, cyanines, and boron-dipyrromethenes (also known as BODIPYs). The fluorophores may be attached to the remainder of a compound of formula (I), for example, by using a reagent comprising a fluorophore and a reactive group such as a carboxylic acid, an isothiocyanate, a maleimide, or an ester such as a succinimidyl, pentafluorophenyl or tetrafluorophenyl ester. Such groups may react with a group present on a linker precursor compound, such as an amine, to attach the fluorophore to the remainder of the molecule of formula (I).

Suitable reagents comprising fluorophores, which may be used to prepare compounds of formula (I), are known in the art, and include but are not limited to fluoresceins, rhodamines, coumarins, cyanines and boron-dipyrromethenes. For example, reagents comprising fluorophores that are commercially available include but are not limited to: 5- and 6-carboxyfluoresceins and esters thereof; fluorescein-5-isothiocyanate and fluorescein-6-isothiocyanate; BODIPY® dyes commercially available from Molecular Probes; Alexa Fluor® dyes commercially available from Molecular Probes; CyDye fluors commercially available from GE Healthcare Biosciences, including but not limited to Cy3, Cy 5, Cy5.5 and Cy 7 esters; and VivoTag™ fluorophores available from PerkinElmer, including but not limited to VivoTag 645, VivoTag 645-MAL, VivoTag 680, VivoTag 680-MAL, VivoTag 680 XL, VivoTag-S 680, VivoTag 750, VivoTag-S 750, VivoTag 750-MAL, and VivoTag 800.

It will be understood by the skilled artisan that when B is a detection moiety, e.g., a detection moiety comprising a fluorophore, the detection moiety may include the detectable moiety as well as additional atoms or groups of atoms. For example, as will be further described in the synthesis section, a fluorophore may be attached to the remainder of a compound of formula (I), for example, by reacting a compound of the formula A-X$_1$-L-NH$_2$ with a reagent comprising a fluorophore and a reactive group, such as an isothiocyanate or N-succinimidyl ester. A reaction with an isothiocyanate will produce a compound A-X$_1$-L-NH—C(S)—NH-fluorophore. In such instances, it is understood that the —NH— group attached to -L-corresponds to the —X$_2$— group of formula (I), while the group —B corresponding to the "detection moiety" includes not only the fluorophore but also the —C(S)—NH— linking atoms.

In other embodiments, the detection moiety may comprise a radioisotope. Such detection moieties may be useful for detection in samples by scintillation counting, or for radioimaging applications. Suitable radioisotopes include, but are not limited to, tritium (i.e. hydrogen-3), carbon-14, nitrogen-15, phosphorus-32, iodine-125 and iodine-131. For example, compounds comprising iodine-131 may be useful as radiopharmaceuticals.

e. Anti-Cancer Agents

In embodiments of the compounds of formula (I), B comprises an anti-cancer agent. Exemplary anti-cancer/chemotherapeutic agents include, but are not limited to, the following:

alkylating agents (including, without limitation, nitrogen mustards, ethylenimine derivatives, alkyl sulfonates, nitrosoureas and triazenes): uracil mustard (Aminouracil Mustard®, Chlorethaminacil®, Demethyldopan®, Desmethyldopan®, Haemanthamine®, Nordopan®, Uracil nitrogen Mustard®, Uracillost®, Uracilmostaza®, Uramustin®, Uramustine®), bendamustine (Treakisym®, Ribomustin®, Treand®) chlormethine (Mustargen®), cyclophosphamide (Cytoxan®, Neosar®, Clafen®, Endoxan®, Procytox®, Revimmune™), ifosfamide (Mitoxana®), melphalan (Alkeran®), Chlorambucil (Leukeran®), pipobroman (Amedel®, Vercyte®), triethylenemelamine (Hemel®, Hexylen®, Hexastat®), triethylenethiophosphoramine, Temozolomide (Temodar®), thiotepa (Thioplex®), busulfan (Busilvex®, Myleran®), carmustine (BiCNU®), lomustine (CeeNU®), streptozocin (Zanosar®), estramustine (Emcyt®, Estracit®), fotemustine, irofulven, mannosulfan, mitobronitol, nimustine, procarbazine, ranimustine, semustine, triaziquone, treosulfan, and Dacarbazine (DTIC-Dome®).

anti-EGFR antibodies (e.g., cetuximab (Erbitux®), panitumumab (Vectibix®), and gefitinib (Iressa®)).

anti-Her-2 antibodies (e.g., trastuzumab (Herceptin®) and other antibodies from Genentech).

antimetabolites (including, without limitation, folic acid antagonists (also referred to herein as antifolates), pyrimidine analogs, purine analogs and adenosine deaminase inhibitors): methotrexate (Rheumatrex®, Trexall®), 5-fluorouracil (Adrucil®, Efudex®, Fluoroplex®), floxuridine (FUDF®), carmofur, cytarabine (Cytosar-U®, Tarabine PFS), 6-mercaptopurine (Puri-Nethol®)), 6-thioguanine (Thioguanine Tabloid®), fludarabine phosphate (Fludara®), pentostatin (Nipent®), pemetrexed (Alimta®), raltitrexed (Tomudex®), cladribine (Leustatin®), clofarabine (Clofarex®, Clolar®), mercaptopurine (Puri-Nethol®), capecitabine (Xeloda®), nelarabine (Arranon®), azacitidine (Vidaza®), decitabine (Dacogen®), enocitabine (Sunrabin®), sapacitabine, tegafur-uracil, tiazofurine, tioguanine, trofosfamide, and gemcitabine (Gemzar®).

vinca alkaloids: vinblastine (Velban®, Velsar®), vincristine (Vincasar®, Oncovin®), vindesine (Eldisine®), vinorelbine (Navelbine®), vinflunine (Javlor®).

platinum-based agents: carboplatin (Paraplat®, Paraplatin®), cisplatin (Platinol®), oxaliplatin (Eloxatin®), nedaplatin, satraplatin, triplatin.

anthracyclines: daunorubicin (Cerubidine®, Rubidomycin®), doxorubicin (Adriamycin®), epirubicin (Ellence®), idarubicin (Idamycin®), mitoxantrone (Novantrone®), valrubicin (Valstar®), aclarubicin, amrubicin, liposomal doxorubicin, liposomal daunorubicin, pirarubicin, pixantrone, zorubicin.

topoisomerase inhibitors: topotecan (Hycamtin®), irinotecan (Camptosar®), etoposide (Toposar®, VePesid®), teniposide (Vumon®), lamellarin D, SN-38, camptothecin (e.g., IT-101), belotecan, rubitecan.

taxanes: paclitaxel (Taxol®), docetaxel (Taxotere®), larotaxel, cabazitaxel, ortataxel, tesetaxel.

antibiotics: actinomycin (Cosmegen®), bleomycin (Blenoxane®), hydroxyurea (Droxia®, Hydrea®), mitomycin (Mitozytrex®, Mutamycin®).

immunomodulators: lenalidomide (Revlimid®), thalidomide (Thalomid®).

immune cell antibodies: alemtuzamab (Campath®), gemtuzumab (Myelotarg®), rituximab (Rituxan®), tositumomab (Bexxar®).

interferons (e.g., IFN-alpha (Alferon®, Roferon-A®, Intron®-A) or IFN-gamma (Actimmune®)).

interleukins: IL-1, IL-2 (Proleukin®), IL-24, IL-6 (Sigosix®), IL-12.

HSP90 inhibitors (e.g., geldanamycin or any of its derivatives). In certain embodiments, the HSP90 inhibitor is selected from geldanamycin, 17-alkylamino-17-desmethoxygeldanamycin ("17-AAG") or 17-(2-dimethylaminoethyl)amino-17-desmethoxygeldanamycin ("17-DMAG").

anti-androgens which include, without limitation nilutamide (Nilandron®) and bicalutamide (Caxodex®).

antiestrogens which include, without limitation tamoxifen (Nolvadex®), toremifene (Fareston®), letrozole (Femara®), testolactone (Teslac®), anastrozole (Arimidex®), bicalutamide (Casodex®), exemestane (Aromasin®), flutamide (Eulexin®), fulvestrant (Faslodex®), raloxifene (Evista®, Keoxifene®) and raloxifene hydrochloride.

anti-hypercalcaemia agents which include without limitation gallium (III) nitrate hydrate (Ganite®) and pamidronate disodium (Aredia®).

apoptosis inducers which include without limitation ethanol, 2-[[3-(2,3-dichlorophenoxyl)propyl]amino]-(9Cl), gambogic acid, elesclomol, embelin and arsenic trioxide (Trisenox®).

Aurora kinase inhibitors which include without limitation binucleine 2.

Bruton's tyrosine kinase inhibitors which include without limitation terreic acid.

calcineurin inhibitors which include without limitation cypermethrin, deltamethrin, fenvalerate and tyrphostin 8.

CaM kinase II inhibitors which include without limitation 5-Isoquinolinesulfonic acid, 4-[{2S)-2-[(5-isoquinolinylsulfonyl)methylamino]-3-oxo-3-{4-phenyl-1-piperazinyl)propyl]phenyl ester and benzenesulfonamide.

CD45 tyrosine phosphatase inhibitors which include without limitation phosphonic acid.

CDC25 phosphatase inhibitors which include without limitation 1,4-naphthalene dione, 2,3-bis[(2-hydroxyethyl) thio]-(9Cl).

CHK kinase inhibitors which include without limitation debromohymenialdisine.

cyclooxygenase inhibitors which include without limitation 1H-indole-3-acetamide, 1-(4-chlorobenzoyl)-5-methoxy-2-methyl-N-(2-phenylethyl)-(9Cl), 5-alkyl substituted 2-arylaminophenylacetic acid and its derivatives (e.g., celecoxib (Celebrex®), rofecoxib (Vioxx®), etoricoxib (Arcoxia®), lumiracoxib (Prexige®), valdecoxib (Bextra®) or 5-alkyl-2-arylaminophenylacetic acid).

cRAF kinase inhibitors which include without limitation 3-(3,5-dibromo-4-hydroxybenzylidene)-5-iodo-1,3-dihydroindol-2-one and benzamide, 3-(dimethylamino)-N-[3-[(4-hydroxybenzoyl)amino]-4-methylphenyl]-(9Cl).

cyclin dependent kinase inhibitors which include without limitation olomoucine and its derivatives, purvalanol B, roascovitine (Seliciclib®), indirubin, kenpaullone, purvalanol A and indirubin-3'-monooxime.

cysteine protease inhibitors which include without limitation 4-morpholinecarboxamide, N-[(1S)-3-fluoro-2-oxo-1-(2-phenylethyl)propyl]amino]-2-oxo-1-(phenylmeth-yl) ethyl]-(9Cl).

DNA intercalators which include without limitation plicamycin (Mithracin®) and daptomycin (Cubicin®).

DNA strand breakers which include without limitation bleomycin (Blenoxane®).

E3 ligase inhibitors which include without limitation N-((3,3,3-trifluoro-2-trifluoromethyl)propionyl)sulfanilamide.

EGF Pathway Inhibitors which include, without limitation tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747,498, WO 98/10767, WO 97/30034, WO 97/49688, WO 97/38983 and WO 96/33980.

farnesyltransferase inhibitors which include without limitation a-hydroxyfarnesylphosphonic acid, butanoic acid, 2-[(2S)-2-[[(2S,3S)-2-[[(2R)-2-amino-3-mercaptopropyl] amino]-3-methylpent-yl]oxy]-1-oxo-3-phenylpropyl] amino]-4-(methylsulfonyl)-1-methylethylester (2S)-(9Cl), tipifarnib (Zarnestra®), and manumycin A.

Flk-1 kinase inhibitors which include without limitation 2-propenamide, 2-cyano-3-[4-hydroxy-3,5-bis(1-methylethyl)phenyl]-N-(3-phenylpropyl)-(2E-)-(9Cl).

glycogen synthase kinase-3 (GSK3) inhibitors which include without limitation indirubin-3'-monooxime.

histone deacetylase (HDAC) inhibitors which include without limitation suberoylanilide hydroxamic acid (SAHA), [4-(2-amino-phenylcarbamoyl)-benzyl]-carbamic acid pyridine-3-ylmethylester and its derivatives, butyric acid, pyroxamide, trichostatin A, oxamflatin, apicidin, depsipeptide, depudecin, trapoxin, vorinostat (Zolinza®), and compounds disclosed in WO 02/22577.

I-kappa B-alpha kinase inhibitors (IKK) which include without limitation 2-propenenitrile, 3-[(4-methylphenyl)sulfonyl]-(2E)-(9CI).

imidazotetrazinones which include without limitation temozolomide (Methazolastone®, Temodar® and its derivatives (e.g., as disclosed generically and specifically in U.S. Pat. No. 5,260,291) and Mitozolomide.

insulin tyrosine kinase inhibitors which include without limitation hydroxyl-2-naphthalenylmethylphosphonic acid.

c-Jun-N-terminal kinase (JNK) inhibitors which include without limitation pyrazoleanthrone and epigallocatechin gallate.

mitogen-activated protein kinase (MAP) inhibitors which include without limitation benzenesulfonamide, N-[2-[[[3-(4-chlorophenyl)-2-propenyl]methyl]amino]methyl]phenyl]-N-(2-hy-droxyethyl)-4-methoxy-(9CI).

MDM2 inhibitors which include without limitation trans-4-iodo, 4'-boranyl-chalcone.

MEK inhibitors which include without limitation butanedinitrile, bis[amino[2-aminophenyl)thio]methylene]-(9CI).

MMP inhibitors which include without limitation Actinonin, epigallocatechin gallate, collagen peptidomimetic and non-peptidomimetic inhibitors, tetracycline derivatives marimastat (Marimastat®), prinomastat, incyclinide (Metastat®), shark cartilage extract AE-941 (Neovastat®), Tanomastat, TAA211, MMI270B or AAJ996.

mTor inhibitors which include without limitation rapamycin (Rapamune®), and analogs and derivatives thereof, AP23573 (also known as ridaforolimus, deforolimus, or MK-8669), CCI-779 (also known as temsirolimus) (Torisel®) and SDZ-RAD.

NGFR tyrosine kinase inhibitors which include without limitation tyrphostin AG 879.

p38 MAP kinase inhibitors which include without limitation Phenol, 4-[4-(4-fluorophenyl)-5-(4-pyridinyl)-1H-imidazol-2-yl]-(9CI), and benzamide, 3-(dimethylamino)-N-[3-[(4-hydroxylbenzoyl)amino]-4-methylphenyl]-(9CI).

p56 tyrosine kinase inhibitors which include without limitation damnacanthal and tyrphostin 46.

PDGF pathway inhibitors which include without limitation tyrphostin AG 1296, tyrphostin 9, 1,3-butadiene-1,1,3-tricarbonitrile, 2-amino-4-(1H-indol-5-yl)-(9CI), imatinib (Gleevec®) and gefitinib (Iressa®) and those compounds generically and specifically disclosed in European Patent No.: 0 564 409 and PCT Publication No.: WO 99/03854.

phosphatidylinositol 3-kinase inhibitors which include without limitation wortmannin, and quercetin dihydrate.

phosphatase inhibitors which include without limitation cantharidic acid, cantharidin, and L-leucinamide.

protein phosphatase inhibitors which include without limitation cantharidic acid, cantharidin, L-P-bromotetramisole oxalate, 2(5H)-furanone, 4-hydroxy-5-(hydroxymethyl)-3-(1-oxohexadecyl)-(5R)-(9CI) and benzylphosphonic acid.

PKC inhibitors which include without limitation 1-H-pyrollo-2,5-dione,3-[1-3-(dimethylamino)propyl]-1H-indol-3-yl]-4-(1H-indol-3-yl)-(9CI), Bisindolylmaleimide IX, Sphinogosine, staurosporine, and Hypericin.

PKC delta kinase inhibitors which include without limitation rottlerin.

polyamine synthesis inhibitors which include without limitation DMFO.

PTP1B inhibitors which include without limitation L-leucinamide.

protein tyrosine kinase inhibitors which include, without limitation tyrphostin Ag 216, tyrphostin Ag 1288, tyrphostin Ag 1295, geldanamycin, genistein and 7H-pyrrolo[2,3-d] pyrimidine derivatives as generically and specifically described in PCT Publication No.: WO 03/013541 and U.S. Publication No.: 2008/0139587.

SRC family tyrosine kinase inhibitors which include without limitation PP1 and PP2.

Syk tyrosine kinase inhibitors which include without limitation piceatannol.

Janus (JAK-2 and/or JAK-3) tyrosine kinase inhibitors which include without limitation tyrphostin AG 490 and 2-naphthyl vinyl ketone.

retinoids which include without limitation isotretinoin (Accutane®, Amnesteem®, Cistane®, Claravis®, Sotret®) and tretinoin (Aberel®, Aknoten®, Avita®, Renova®, Retin-A®, Retin-A MICRO®, Vesanoid®).

RNA polymerase II elongation inhibitors which include without limitation 5,6-dichloro-1-beta-D-ribofuranosylbenzimidazole.

serine/Threonine kinase inhibitors which include without limitation 2-aminopurine.

sterol biosynthesis inhibitors which include without limitation squalene epoxidase and CYP2D6.

VEGF pathway inhibitors, which include without limitation anti-VEGF antibodies, e.g., bevacizumab, and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™)

Examples of chemotherapeutic agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Other exemplary anti-cancer agents include alitretinon, altretamine, aminopterin, aminolevulinic acid, amsacrine (Amsidine®), asparaginase (crisantaspase, Erwinase®), atrasentan, bexarotene (Targretin®), carboquone, demecolcine, efaproxiral, elsamitrucin, etoglucid, ferrocene, Gliadel implants, hydroxycarbamide, leucovorin, lonidamine, lucanthone, masoprocol, methyl aminolevulinate, mitoguazone, mitotane (Lysodren®), oblimersen, omacetaxine (Genasense®), pegaspargase (Oncaspar®), porfimer sodium (Photofrin®), prednimustine, sitimagene ceradenovec (Cerepro®), talaporfin, temoporfin, trabectedin (Yondelis®), and verteporfin.

It will be understood by the skilled artisan that when B comprises an anti-cancer agent, the anti-cancer agent may be attached to the linker group of the compound of formula (I) by any suitable linkage. For example, if the anti-cancer agent has a reactive moiety such as a hydroxyl group, an amine group, or the like, such groups may be used to attach the anti-cancer agent to the remainder of the compound of formula (I). Alternatively, an anti-cancer agent may be further derivatized with an atom or a group of atoms in order to provide a reactive group. In such instances, it is understood that the group —B corresponding to the anti-cancer agent includes not only the anti-cancer agent itself but also the linking atoms.

f. Preparation of Compounds

Compounds described herein may be prepared according to a variety of methods. A representative synthesis of exemplary compounds of formula (I) is illustrated in Scheme 1.

Scheme 1. Exemplary Synthesis

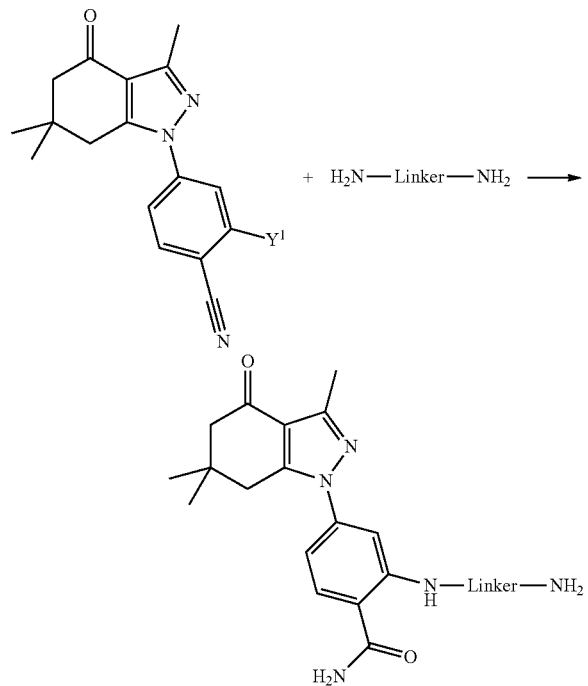

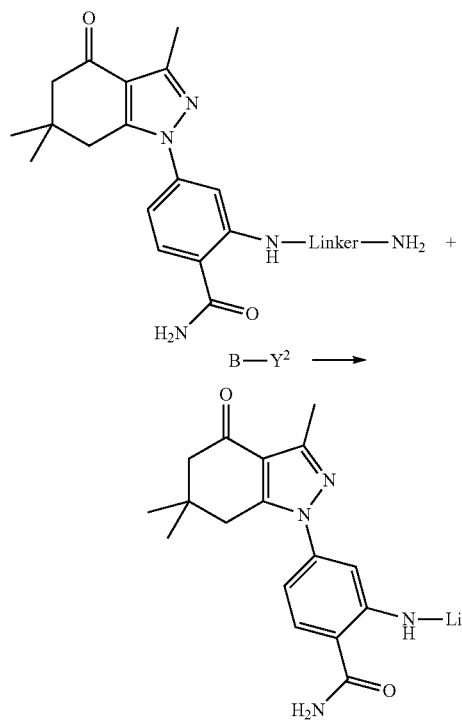

In reaction 1 of Scheme 1, the starting material includes an exemplary Hsp90-binding moiety precursor, and the group $Y^1$ is a leaving group or a reactive group. For example and as illustrated in Scheme 1, $Y^1$ may be leaving group such as a halogen, such that the compound $H_2N$-Linker-$NH_2$ may react with the compound via a reaction such as nucleophilic aromatic substitution. The nitrile can then be subsequently hydrolyzed to produce the Hsp90-binding moiety.

In reaction 2 of Scheme 1, the product of the initial reaction is further reacted with a compound B—$Y^2$, where B comprises a detection moiety, an anti-cancer agent or an Hsp90 binding component, and $Y^2$ is a leaving group or a reactive group. For example, $Y^2$ may be reactive group such as an isothiocyanate or a maleimide.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

g. Evaluation of Compounds

Compounds can be evaluated by determining their ability to bind to Hsp90. The selectivity for Hsp90 over other proteins, such as GRP94 and TRAP1, may also be determined For example, prior to attachment of a detection moiety, an A-Linker-$NH_2$ compound can be bound to Sepharose resin. Such a resin can be exposed to a pig mammary gland extract, which is a tissue known to be high in ATP binding proteins including native forms of Hsp90, GRP94 and TRAP1. Media can be incubated with extract, washed stringently, and bound proteins removed with SDS and subsequently characterized. Preincubation of the resin with a known Hsp90 inhibitor should selectively block binding of Hsp90 and associated proteins, while those recovered in the presence of such a quenching agent are likely to be non-specifically bound.

Compounds of formula (I) may have increased selectivity for Hsp90 compared to proteins that share sequence homology with Hsp90. For example, the compounds may bind to Hsp90 with an affinity that is at least about 100 to 1000 fold higher than the affinity for GRP94, a molecular chaperone that functions in the processing and transport of secreted proteins. The Hsp90 affinity probe may bind to Hsp90 with an affinity that is at least about 100 fold to 1000-fold higher than the affinity for TRAP1, (TNF receptor-associated protein 1), a heat shock protein of 75 kDa. This increased selectivity may lead to more accurate detection and targeting of Hsp90.

3. METHODS OF USE

Compounds of formula (I) may be used in a variety of methods, such as methods of detecting Hsp90 in a sample, methods of detecting cancer in a subject, and methods of treating cancer in a subject.

a. Methods of Detecting Hsp90

In some embodiments, compounds described herein can be used in methods of detecting Hsp90 in a sample, the methods comprising:

a) contacting the sample with a compound having the following formula (Ia):

$$A\text{-}X^1\text{-}L\text{-}X^2\text{--}B \qquad (Ia)$$

wherein:

A is an Hsp90 binding component;

$X^1$ is selected from the group consisting of —NH—, —O—, —S—, —C(O)— and —S(O)$_2$—;

$X^2$ is selected from the group consisting of —NR—, —O—, —S—, —C(O)— and —S(O)$_2$—;

L is a divalent linker comprising at least twelve member atoms independently selected from carbon, nitrogen and oxygen, wherein at least one member atom is nitrogen or oxygen;

B is a detection moiety; and

R is selected from the group consisting of hydrogen and a detection moiety; and b) detecting a signal from the detection moiety.

In some embodiments, the sample is an in vitro sample, such as a cell or tissue extract. In some embodiments, the sample is a cell culture. For example, the sample may be a culture of cells such as cancer cells.

In some embodiments, the sample is a biological sample from a subject, such as a human. In some embodiments, the biological sample is selected from the group consisting of a tissue sample, bodily fluid, whole blood, plasma, serum, urine, bronchoalveolar lavage fluid, and a cell culture suspension or fraction thereof. In embodiments in which Hsp90 is detected in a biological sample from a subject, the methods may further involve providing or obtaining a biological sample from the subject, which can be obtained by any known means including needle stick, needle biopsy, swab, and the like. In an embodiment of such methods, the biological sample is a blood sample, such as a blood plasma or serum sample, which may be obtained by any standard technique such as, for example, by venipuncture. Biological samples used in the methods may be stored or banked under suitable tissue storage conditions, or can be accessed from samples that have been previously stored or banked under suitable conditions.

Following contacting the sample with a compound, the method further includes detecting a signal from the detection moiety. A signal may be detected by any suitable means appropriate for the particular detection moiety being used. For example, when the detection moiety comprises a fluorophore, a signal may be detected using a fluorometer or a fluorescence plate reader, or by using fluorescence techniques such as fluorescence microscopy, fluorescence resonance energy transfer, flow cytometry and fluorescence-activated cell sorting. In embodiments in which the detection moiety comprises a radioisotope, a signal may be detected using scintillation counting or radioimaging techniques.

A signal from the detection moiety may be quantitated, for example, by comparing the quantity of the signal to that of a reference sample.

b. Methods of Detecting Cancer

In some embodiments, compounds described herein can be used in a method of detecting cancer in a subject, the method comprising:

a) contacting a biological sample from the subject with a compound having the following formula (Ia):

$$A\text{-}X^1\text{-}L\text{-}X^2\text{--}B \qquad (Ia)$$

wherein:

A is an Hsp90 binding component;

$X^1$ is selected from the group consisting of —NH—, —O—, —S—, —C(O)— and —S(O)$_2$—;

$X^2$ us selected from the group consisting of —NR—, —O—, —S—, —C(O)— and —S(O)$_2$—;

L is a divalent linker comprising at least twelve member atoms independently selected from carbon, nitrogen and oxygen, wherein at least one member atom is nitrogen or oxygen;

B is a detection moiety; and

R is selected from the group consisting of hydrogen and a detection moiety; and b) detecting a signal from the detection moiety;

wherein cancer is detected in the sample when the signal from the detection moiety is higher relative to a signal from a reference sample.

In some embodiments, the method further comprises obtaining the biological sample from the subject, such as a biological sample described herein, according to methods described herein. In some embodiments, the subject is a human.

A reference sample may be a sample from a healthy subject, i.e. a subject having no clinical signs or symptoms of cancer. Suitably, the healthy subject may be clinically evaluated for otherwise undetected signs or symptoms of cancer, which evaluation may include routine physical examination and/or laboratory testing.

In embodiments, the cancer may be any type of cancer, such as a cancer recognized by the National Cancer Institute. In embodiments, the cancer may be a type of cancer associated with elevated levels of Hsp90. Exemplary types of cancers include the following:

Digestive/gastrointestinal cancers such as anal cancer; bile duct cancer; extrahepatic bile duct cancer; appendix cancer; carcinoid tumor, gastrointestinal cancer; colon cancer; colorectal cancer including childhood colorectal cancer; esophageal cancer including childhood esophageal cancer; gallbladder cancer; gastric (stomach) cancer including childhood gastric (stomach) cancer; hepatocellular (liver) cancer including adult (primary) hepatocellular (liver) cancer and childhood (primary) hepatocellular (liver) cancer; pancreatic cancer including childhood pancreatic cancer; sarcoma, rhabdomyosarcoma; islet cell pancreatic cancer; rectal cancer; and small intestine cancer;

Breast cancer, including childhood breast cancer, male breast cancer and breast cancer during pregnancy;

Genitourinary cancers such as bladder cancer including childhood bladder cancer; renal cell (kidney) cancer; ovarian cancer including childhood ovarian cancer; ovarian epithelial cancer; ovarian low malignant potential tumor; penile cancer; prostate cancer; renal cell cancer including childhood renal cell cancer; renal pelvis and ureter, transitional cell cancer; testicular cancer; urethral cancer; vaginal cancer; vulvar cancer; cervical cancer; Wilms tumor and other childhood kidney tumors; endometrial cancer; and gestational trophoblastic tumor;

Lung cancer such as non-small cell lung cancer; and small cell lung cancer;

Respiratory cancers such as malignant mesothelioma, adult; malignant mesothelioma, childhood; malignant thymoma; childhood thymoma; thymic carcinoma; bronchial adenomas/carcinoids including childhood bronchial adenomas/carcinoids; pleuropulmonary blastoma; non-small cell lung cancer; and small cell lung cancer; and Skin cancers such as Kaposi's sarcoma; Merkel cell carcinoma; melanoma; and childhood skin cancer.

In suitable embodiments, the cancer may be a cancer that is associated with increased levels of Hsp90, including but not limited to breast cancer, prostate cancer, non-small cell lung cancer, colorectal cancer, pancreatic cancer, ovarian cancer and melanoma. In particular embodiments, the cancer is breast cancer or prostate cancer.

c. Methods of Treating Cancer

In some embodiments, compounds described herein can be used in a method of treating cancer in a subject in need of treatment. Such methods comprise administering the subject a therapeutically effective amount of a compound having the following formula (Ib):

$$A\text{-}X^1\text{-}L\text{-}X^2\text{---}B \tag{Ib}$$

wherein:

A is an Hsp90 binding component;

$X^1$ and $X^2$ are each independently selected from the group consisting of —NH—, —O—, —S—, —C(O)— and —S(O)$_2$—;

L is a divalent linker comprising at least twelve member atoms independently selected from carbon, nitrogen and oxygen, wherein at least one member atom is nitrogen or oxygen; and B is selected from the group consisting of an anti-cancer agent and an Hsp90 binding component.

In embodiments, the cancer is a cancer described herein. In embodiments, the cancer is selected from the group consisting of breast cancer, prostate cancer, non-small cell lung cancer, colorectal cancer, pancreatic cancer, ovarian cancer and melanoma. In particular embodiments, the cancer is breast cancer or prostate cancer.

In embodiments, the anti-cancer agent is an anti-cancer agent described herein. In embodiments, B is an anti-cancer agent selected from the group consisting of a protein kinase inhibitor, a protein phosphatase inhibitor and a histone deacetylase inhibitor.

In the methods of treating cancer, a compound, or a pharmaceutical composition comprising the compound, may be administered to the subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Additional modes of administration may include adding the compound and/or a composition comprising the compound to a food or beverage, including a water supply for an animal, to supply the compound as part of the animal's diet.

While it is possible for the compound to be administered alone, in some embodiments the compound may be presented as a pharmaceutical composition (e.g., formulation) comprising at least one compound, as defined above, together with one or more pharmaceutically-acceptable carriers, adjuvants, excipients, diluents, fillers, buffers, stabilizers, preservatives, lubricants, or other materials well known to those skilled in the art and optionally other therapeutic or prophylactic agents.

Thus, the disclosure further provides pharmaceutical compositions, as defined above, and methods of making a pharmaceutical composition comprising admixing at least one compound, as defined above, together with one or more pharmaceutically acceptable carriers, excipients, buffers, adjuvants, stabilizers, or other materials, as described herein.

Suitable carriers, excipients, etc. can be found in standard pharmaceutical texts, for example Remington's Pharmaceutical Sciences, 18th edition, Mack Publishing Company, Easton, Pa., 1990.

The formulations may conveniently be presented in unit dosage form and may be prepared by any method well known in the art of pharmacy. Such methods include the step of bringing into association the compound with the carrier which constitutes one or more accessory ingredients. In general, the formulations may be prepared by uniformly and intimately bringing into association the compound with liquid carriers or finely divided solid carriers or both, and then if necessary shaping the product.

Formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g., compression or molding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g., transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with compounds and optionally one or more excipients or diluents. In addition, a formulation may be added to a conventional bandage, e.g. to a gauze portion that contacts a wound, as an antimicrobial agent.

Formulations suitable for topical administration in the mouth include lozenges comprising the compound in a flavored basis, usually sucrose and acacia or tragacanth; pastilles comprising the compound in an inert basis such as gelatin and glycerin, or sucrose and acacia; and mouthwashes comprising the compound in a suitable liquid carrier.

Formulations suitable for topical administration to the eye also include eye drops wherein the compound is dissolved or suspended in a suitable carrier, especially an aqueous solvent for the compound.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the compound.

Formulations suitable for administration by inhalation include those presented as an aerosol spray from a pressurized pack, with the use of a suitable propellant, such as dichlorodifluoromethane, trichlorofluoromethane, dichlorotetrafluoroethane, carbon dioxide, or other suitable gases.

Formulations suitable for topical administration via the skin include ointments, creams, and emulsions. When formulated in an ointment, the compound may optionally be employed with either a paraffinic or a water-miscible ointment base. Alternatively, the compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Suitable emulgents and emulsion stabilizers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats in addition to the compound, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the compound in the solution is from about 1 ng/ml to about 1 µg/ml, although other concentrations are possible and are encompassed within the invention. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the compound to blood components or one or more organs.

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the compound is in the range of about 100 µg to about 250 mg per kilogram body weight of the subject per day.

The composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved.

The present compounds, compositions, and methods may be administered as part of a therapeutic regimen along with other treatments appropriate for the particular injury or disease being treated.

d. Methods of Detecting HIV

In some embodiments, compounds described herein can be used in a method of detecting Human Immunodeficiency Virus (HIV) in a subject, the method comprising:

a) contacting a biological sample from the subject with a compound having the following formula (Ia):

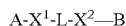
(Ia)

wherein:
A is an Hsp90 binding component;
$X^1$ is selected from the group consisting of —NH—, —O—, —S—, —C(O)— and —S(O)$_2$—;
$X^2$ is selected from the group consisting of —NR—, —O—, —S—, —C(O)— and —S(O)$_2$—;
L is a divalent linker comprising at least twelve member atoms independently selected from carbon, nitrogen and oxygen, wherein at least one member atom is nitrogen or oxygen;
B is a detection moiety; and
R is selected from the group consisting of hydrogen and a detection moiety; and b) detecting a signal from the detection moiety; wherein HIV is detected in the sample when the signal from the detection moiety is higher relative to a signal from a reference sample.

4. KITS

In another aspect, the disclosure provides a kit, which may be used for detecting Hsp90 in a sample, for detecting cancer in a sample, or for treating cancer in a subject.

A kit will include a compound of formula (I) as described herein. A kit may also include instructions for use of the compound of formula (I). Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD, DVD), and the like. As used herein, the term "instructions" can include the address of an internet site that provides the instructions.

In one embodiment, the disclosure provides a kit for detecting Hsp90 in a sample. The kit comprises at least one compound of formula (I), and instructions for assaying the test sample for Hsp90. For example, the kit can comprise instructions for assaying the test sample for Hsp90 by fluorescence detection. The kit may further comprise a calibrator or control, e.g., purified, and optionally lyophilized, (e.g., Hsp90), and/or at least one container (e.g., tube, microtiter plates or strips) for conducting the assay, and/or a buffer, such as an assay buffer or a wash buffer, either one of which can be provided as a concentrated solution. Preferably, the kit comprises all components, i.e., reagents, standards, buffers, diluents, etc., which are necessary to perform the assay. The instructions also can include instructions for generating a standard curve or a reference standard for purposes of quantifying Hsp90.

The kit can also optionally include other reagents required to conduct a diagnostic assay or facilitate quality control evaluations, such as buffers, salts, enzymes, enzyme cofactors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a blood sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

It will be readily apparent to those skilled in the art that other suitable modifications and adaptations of the compounds and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

EXAMPLES

General Experimental and Analytical Details

Reagents were obtained from commercial sources and used without further purification. 1,19-Diamino-4,7,10,13,16-pentaoxanonadecane was obtained from Berry and Associates. Proton NMR spectra were obtained on Varian 400 and 500 MHz spectrometers. LC/MS were obtained on an Agilent ion-trap LC/MS system. HRMS results were obtained on an Agilent 6224 LCMS-TOF and are reported as an average of four runs.

Example 1. Synthesis of 2-Fluoro-4-(3,6,6-trimethyl-4-oxo-4,5,6,7-tetrahydro-1H-indazol-1-yl)benzonitrile (2)

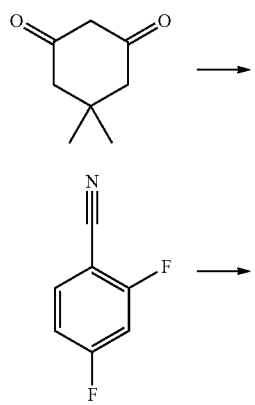

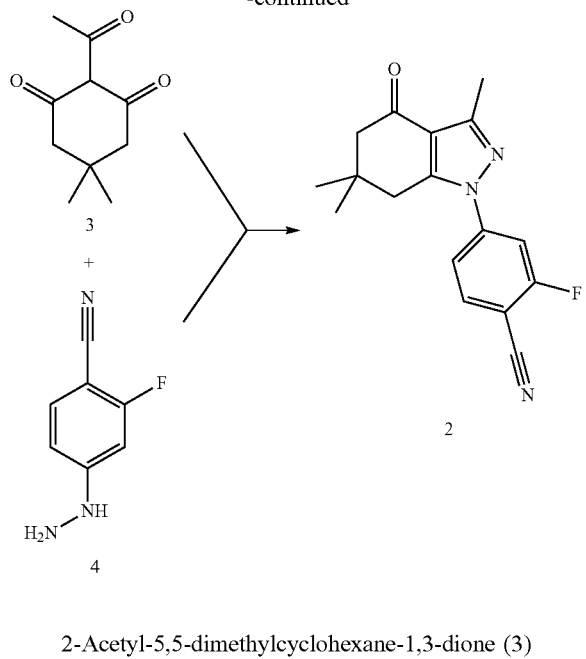

2-Acetyl-5,5-dimethylcyclohexane-1,3-dione (3)

Dimedone (10 g, 71.3 mmol) was dissolved in methylene chloride (200 mL) and treated with Hunig's base (9.7 g, 74.9 mmol) and DMAP (440 mg, 3.6 mmol) followed by slow addition of acetic anhydride (7.65 g, 74.9 mmol). After 24 h, the mixture was concentrated, partitioned between hexanes (150 mL) and 1 N HCl (70 mL), then washed with brine (50 mL), treated with Norit A and then dried (MgSO$_4$), filtered and concentrated to give 2-acetyl-5,5-dimethylcyclohexane-1,3-dione 3 (~11+g) as a yellow oil. The entire product was used in the next step.

2-Fluoro-4-hydrazinylbenzonitrile (4)

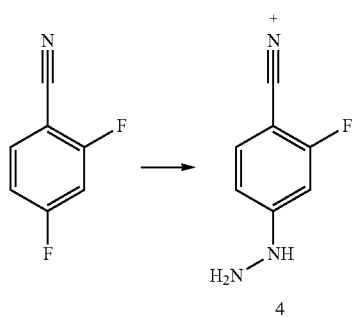 [SMILES: N#Cc1ccc(F)cc1F ; N#Cc1ccc(NN)cc1F]

2,4-difluorobenzonitrile (10 g, 72 mmol) was dissolved in methanol (100 mL) and treated drop wise with hydrazine hydrate (18 g, 0.36 mol) and stirred at RT. After 16 h, the reaction mixture, containing a mixture of isomers, was concentrated then partitioned between ethyl acetate (100 mL), water (70 mL) and 1 N NaOH (30 mL). The organic layer was washed with brine (40 mL) then concentrated to give 2,4-difluorobenzonitrile (4) in a mixture of isomers as a white solid.

2-Fluoro-4-(3,6,6-trimethyl-4-oxo-4,5,6,7-tetrahydro-1H-indazol-1-yl)benzonitrile (2)

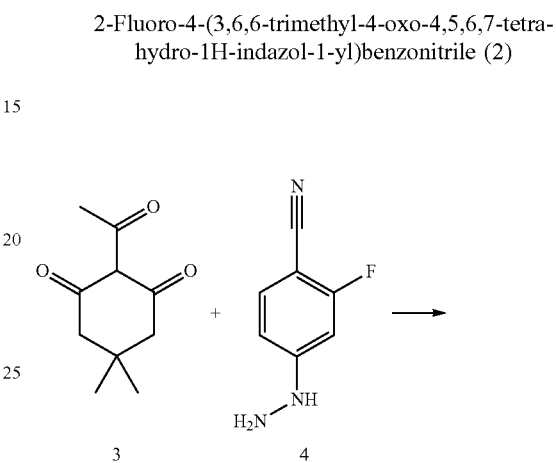

All of 3 (assume 13 g, 71.8 mmol) and 4 (assume 10.9 g, 71.8 mmol) were combined, then dissolved in methanol (40 mL) and treated with acetic acid (1 mL) and stirred at RT for 3 days. The mixture was concentrated and then dissolved in methylene chloride (20 ml). The mixture was chromatographed in a number of batches, with the best approach to load a DCE solution onto a dry column, wait a bit (maybe 15 to 20 min) then elute with 10% ethyl acetate in hexanes to remove the yellow (isomeric product) followed by elution with 20% to get the product. The chromatographed products were recrystallized from ethyl acetate/hexanes to give 2 (10.4 g, 49%). TLC (hexane/EtOAc: 60/40) R$_f$=0.47; $^1$H NMR (CDCl$_3$) δ 7.73 (dd, J=7, 8.5 Hz, 1H), 7.49 (dd, J=2, 9.8 Hz, 1H), 7.45 (dd, J=2, 8.5 Hz, 1H), 2.90 (s, 2H) 2.54 (s, 3H) 2.43 (s, 2H), 1.14 (s, 6H); MS (ESI): m/z 298.2 [M+H]$^+$.

Example 2. Synthesis of 2-(((1r,4r)-4-Hydroxycyclohexyl)amino)-4-(3,6,6-trimethyl-4-oxo-4,5,6,7-tetrahydro-1H-indazol-1-yl)benzamide (5)

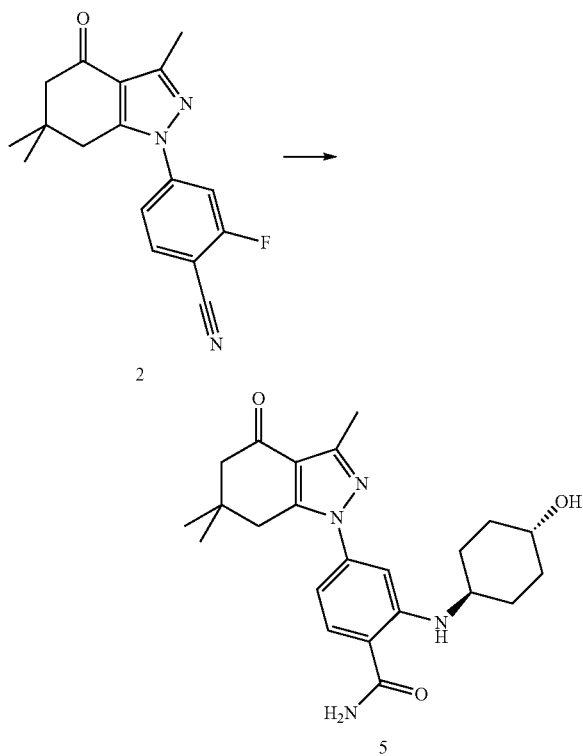

A mixture of nitrile 2 (200 mg, 0.67 mmol) and trans-4-aminocyclohexanol (232 g, 2.0 mmol), Hunig's base (117 μL) and DMSO (300 μL) were heated to 90° C. for 30 m. The mixture diluted with ethanol (2 mL) and treated with 50% NaOH (5 drops) and then, very slowly, a drop at a time, with hydrogen peroxide. After each drop, the reaction foamed up a bit. After adding 5 drops over 10 m, the mixture was diluted with water (18 mL) and allowed to cool slowly with rapid stirring. After stirring overnight, the solid was filtered off to give the product 5 (251 mg, 91%) as a white powder. TLC (EtOAc) $R_f$=0.25; $^1$H NMR (CDCl$_3$) δ 8.07 (d, J=7.2 Hz), 7.44 (d, J=8.6 Hz, 1H), 6.75 (d, J=2 Hz, 1H), 6.60 (dd, J=2, 8.6 Hz, 1H), 5.6 (br s, 2H), 3.71 (m, 1H), 3.35 (m, 1H), 2.80 (s, 2H) 2.53 (s, 3H) 2.38 (s, 2H), 2.13 (m, 2H), 2.02 (m, 2H), 1.64 (br s, 1H), 1.41 (m, 4H), 1.09 (s, 6H); MS (ESI): m/z 411.3 [M+H]$^+$.

Example 3. Attachment of Linkers

6 R = —(CH$_2$)$_2$—O—CH$_2$CH$_2$O—(CH$_2$)$_2$—NH$_2$
7 R = —(CH$_2$)$_{10}$—NH$_2$
8 R = —(CH$_2$)$_3$—O—(CH$_2$CH$_2$O)$_4$—(CH$_2$)$_3$—NH$_2$
9 R = —(CH$_2$)$_3$—O—(CH$_2$CH$_2$O)$_2$—(CH$_2$)$_3$—NH$_2$ 2-((2-(2-(2-aminoethoxyl)ethoxy)ethyl)amino)-4-(3,6,6-trimethyl-4-oxo-4,5,6,7-tetrahydro-1H-indazol-1-yl)benzamide (6)

A mixture of 2 (500 mg, 1.7 mmol) and 2,2'-(ethylenedioxy)bis(ethylamine) (1.2 g, 8.4 mmol) in DMSO (1 mL) were and heated to 90° C. for 30 minutes. The mixture was diluted with ethanol (2 mL) and, still at 90° C., treated with 50% NaOH (20 drops) and very slowly with 30% hydrogen peroxide (40 drops). The reaction mixture was diluted with methylene chloride and methanol and adsorbed onto silica gel. The mixture was chromatographed (silica gel, 1.5 cm×20 cm) and eluted with 9/1 CH$_2$Cl$_2$/MeOH, followed by 9/1/0.1 CH$_2$Cl$_2$/MeOH/NH$_3$ to give 6 (670 mg, 89%) as a clear glass. TLC (4/1/0.1 CH$_2$Cl$_2$/MeOH/NH$_3$) R$_f$=0.14; $^1$H NMR (CDCl$_3$) δ 8.17 (t, J=5 Hz), 7.47 (d, J=8.4 Hz, 1H), 6.77 (d, J=2 Hz, 1H), 6.60 (dd, J=2, 8.4 Hz, 1H), 6.1 (br s, 2H), 3.73 (t, 3H), 3.65 (m, 4H), 3.50 (t, 2H), 3.36 (m, 2H), 2.85 (t, 2H), 2.77 (s, 2H) 2.51 (s, 3H) 2.36 (s, 2H), 1.07 (s, 6H); HRMS (ESI) [M+H]$^+$ calcd for C$_{23}$H$_{34}$N$_5$O$_4$, 444.2605; found 444.2607.

2-((10-aminodecyl)amino)-4-(3,6,6-trimethyl-4-oxo-4,5,6,7-tetrahydro-1H-indazol-1-yl)benzamide (7)

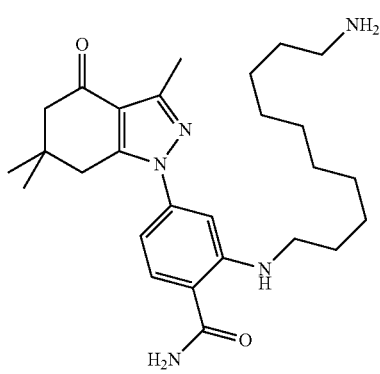

Compound 7 was made in an analogous manner to 6. HRMS (ESI) [M+H]$^+$ calcd for C$_{22}$H$_{42}$N$_5$O$_2$, 468.3333; found 468.3342.

2-((19-Amino-4,7,10,13,16-pentaoxanonadecyl)amino)-4-(3,6,6-trimethyl-4-oxo-4,5,6,7-tetrahydro-1H-indazol-1-yl)benzamide (8)

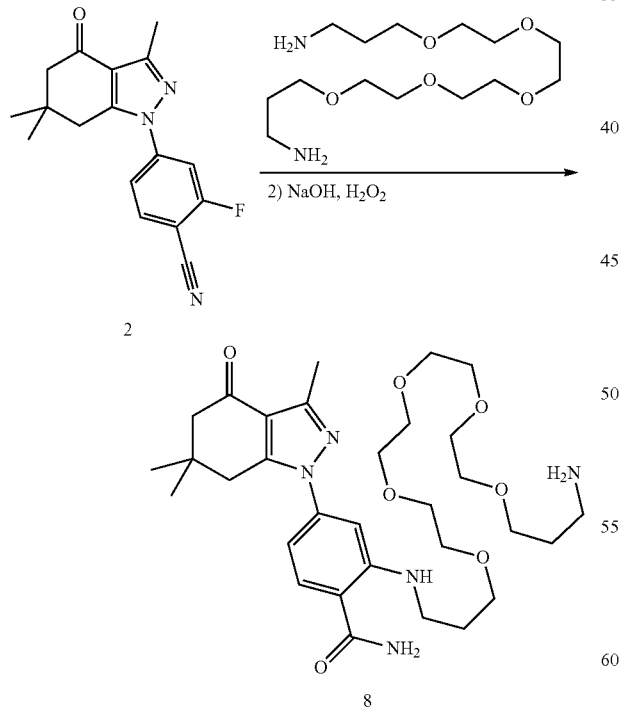

A mixture of 2 (482 mg, 1.62 mmol) and 1,19-diamino-4,7,10,13,16-pentaoxanonadecane (1 g, 3.24 mol), diisopropylethylamine (628 mg, 4.8 mmol) and DMSO (1 mL) were heated to 90° C. for 20 m. Still at 90° C., the mixture diluted with ethanol (2 mL) and treated with 50% NaOH (10 drops) and then, very slowly, a drop at a time, with hydrogen peroxide. After each drop, the reaction foamed up substantially. After about 10 drops over 10 m, the reaction mixture was diluted with ethanol and added to silica gel (6 g) and left overnight. The next day, the slurry was concentrated to a powder, added to a silica gel column (2.5×20 cm) and chromatographed with CH$_2$Cl$_2$ (300 mL), CH$_2$Cl$_2$/MeOH/NH$_3$ 19/0.9/0.1 (300 mL), 9/0.9/0.1 (300 mL) and 4/0.9/0.1 (500 mL). Fractions containing two by-products were set aside (see below). The cleanest fractions were combined to give 8 (600 mg, 61%) as a lightly yellow glass. TLC (4/1/0.1 CH$_2$Cl$_2$/MeOH/NH$_3$) R$_f$=0.30; $^1$H NMR (CDCl$_3$) δ 7.98 (t, J=4 Hz), 7.47 (d, J=8.4 Hz, 1H), 6.77 (d, J=2 Hz, 1H), 6.60 (dd, J=2, 8.4 Hz, 1H), 6.0 (br s, 2H), 3.61 (m, 16H), 3.28 (m, 2H), 2.85 (t, 2H), 2.79 (s, 2H), 2.52 (s, 3H) 2.37 (s, 2H), 2.28 (br s, 2H), 1.94 (m, 2H), 1.76 (m, 2H), 1.07 (s, 6H); HRMS (ESI) [M+H]$^+$ calcd for C$_{31}$H$_{50}$N$_5$O$_7$, 604.3705; found 604.3715.

2-((3-(2-(2-(3-aminopropoxyl)ethoxy)ethoxy)propyl)amino)-4-(3,6,6-trimethyl-4-oxo-4,5,6,7-tetrahydro-1H-indazol-1-yl)benzamide (9)

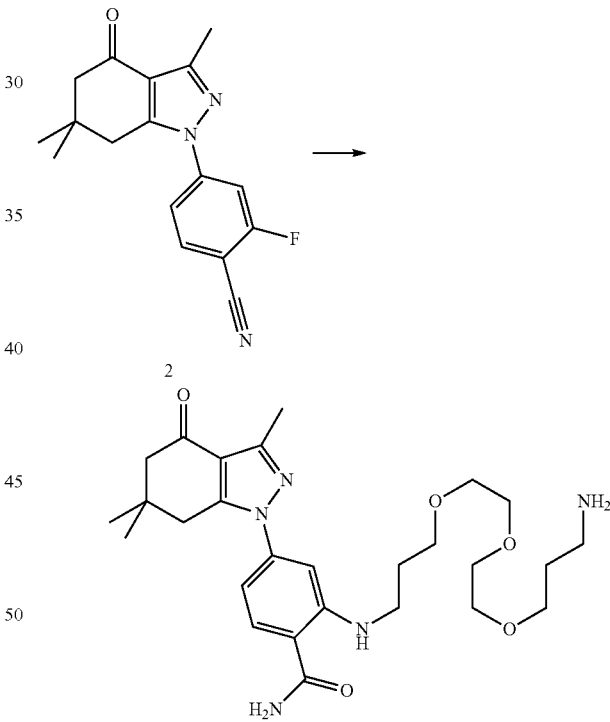

Compound 9 was prepared in the same way as compound 6. TLC (4/1/0.1 CH$_2$Cl$_2$/MeOH/NH$_3$) R$_f$=0.39; $^1$H NMR (CDCl$_3$) δ 8.00 (t, J=5 Hz, 1H), 7.46 (d, J=8.2 Hz, 1H), 6.77 (s, 1H), 6.60 (d, J=8.4 Hz, 1H), 6.1 (br s, 2H), 3.59 (m, 8H), 3.29 (m, 2H), 2.82 (t, 2H), 2.79 (s, 2H) 2.59 (br s, 2H), 2.51 (s, 3H), 2.37 (s, 2h), 1.93 (M, 2h), 1.73 (m, 2H), 1.07 (s, 6H); HRMS (ESI) [M+H]$^+$ calcd for C$_{27}$H$_{42}$N$_5$O$_5$, 516.3180; found 516.3191.

Example 4. Synthesis of Probe Compounds 2-((1-((3',6'-dihydroxy-3-oxo-3H-spiro[isobenzofuran-1,9'-xanthen]-5-yl)amino)-1-thioxo-6,9,12,15,18-pentaoxa-2-azahenicosan-21-yl)amino)-4-(3,6,6-trimethyl-4-oxo-4,5,6,7-tetrahydro-1H-indazol-1-yl)benzamide (10)

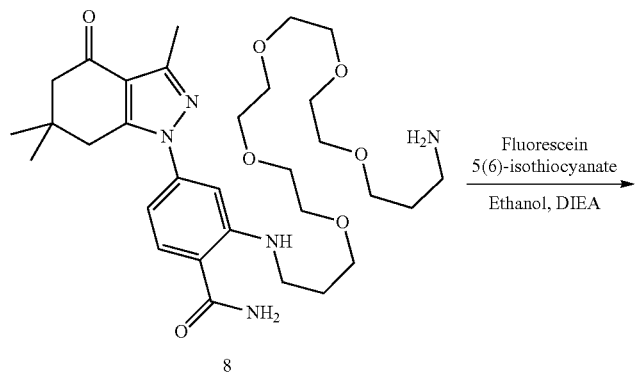

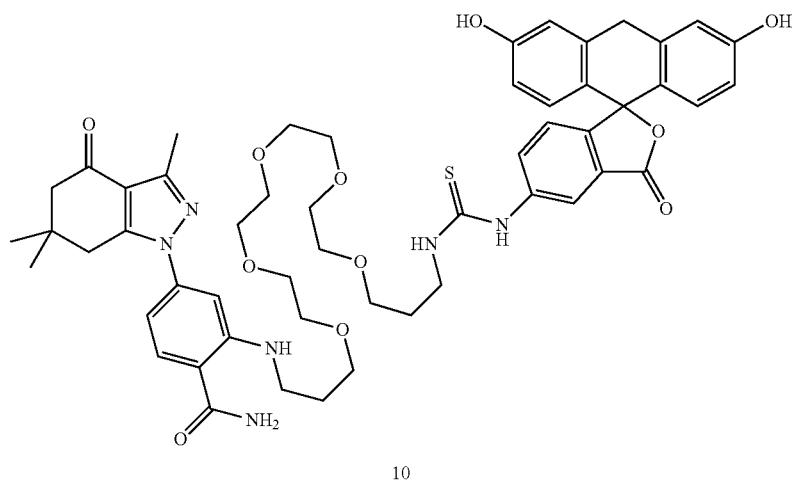

2-((1-((3',6'-dihydroxy-3-oxo-3H-spiro[isobenzofuran-1,9'-xanthen]-5-yl)amino)-1-thioxo-6,9,12,15,18-pentaoxa-2-azahenicosan-21-yl)amino)-4-(3,6,6-trimethyl-4-oxo-4,5,6,7-tetrahydro-1H-indazol-1-yl)benzamide (10). Fluorescein 5(6)-isothiocyanate (35 mg, 90 μmol) was dissolved in ethanol (10 mL) and treated with amine 8 (54.2 mg, 90 μmol) followed by Hunig's base (35 mg, 270 μmol) and stored in a drawer overnight. TLC (CH$_2$Cl$_2$/MeOH/AcOH: 4/1/0.1) showed formation of a new product. The reaction mixture was concentrated to a glass and dissolved in DMSO/water (4/1, 2.5 mL). About half of the product was purified in two injections by chromatography (5 to 100% MeOH, Agilent C-18 21.2×250 mm) to give the product (45 mg) as a yellow solid. TLC (4/0.9/0.1 CH$_2$Cl$_2$/MeOH/NH$_3$) R$_f$=0.3; $^1$H NMR (DMSO-d$_6$) δ 10.2 (br s, 2H), 8.40 (br t, 1H), 8.34 (br s, 1H), 8.23 (s, 1H), 7.92 (b s, 1H), 7.73 (d, J=8.1 Hz, 2H), 7.26 (br s, 1H), 7.15 (d, J=8.1 Hz, 1H), 6.76 (s, 1H), 6.67 (s, 1H), 6.65 (br s, 2H), 6.59 (d, J=8.5 Hz, 2H), 6.54 (d, J=8.5 Hz, 2H), 3.47 (m, 20H), 3.19 (m, 2H), 2.91 (s, 2H), 2.38 (s, 3H), 2.31 (s, 2H), 1.79 (m, 4H), 1.00 (s, 6H); MS (ESI): m/z 993.5 [M+H]$^+$.

2-((19-((7-nitrobenzo[c][1,2,5]oxadiazol-4-yl)amino)-4,7,10,13,16-pentaoxanonadecyl)amino)-4-(3,6,6-trimethyl-4-oxo-4,5,6,7-tetrahydro-1H-indazol-1-yl)benzamide (11)

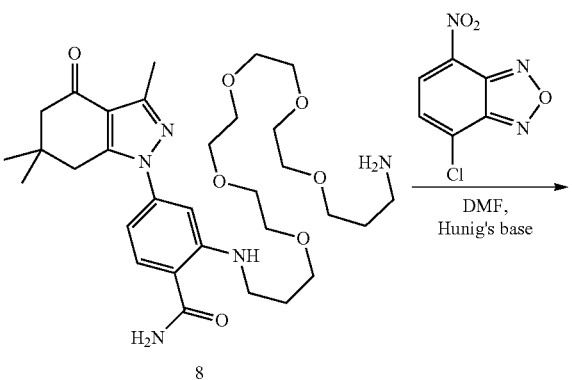

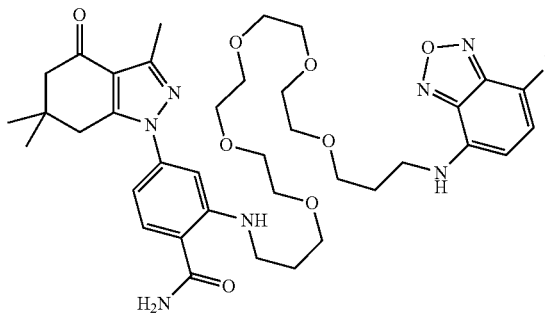

11

2-((19-((7-nitrobenzo[c][1,2,5]oxadiazol-4-yl)amino)-4,7,10,13,16-pentaoxanonadecyl)amino)-4-(3,6,6-trimethyl-4-oxo-4,5,6,7-tetrahydro-1H-indazol-1-yl)benzamide (11). A mixture of Amine 8 (100 mg, 165 μmol) and 4-chloro-7-nitro-1,2,3-benzoxadiazole (40 mg, 200 μmol), Hunig's base (87 μL) and DMF (1 ml) were mixed. The solution turned immediately much darker. TLC (9/1: CH$_2$Cl$_2$/MeOH) showed no starting materials and a major new yellow product, which changed color under UV light. The mixture was concentrated and then chromatographed with CH$_2$Cl$_2$ (200 mL), CH$_2$Cl$_2$/MeOH 19/1 (300 mL), 9/1 (300 mL). The cleanest fractions were combined and then rechromatographed with CH$_2$Cl$_2$ (200 mL), CH$_2$Cl$_2$/MeOH 19/1 (500 mL), 9/1 (300 mL). to give the product (11) (52 mg, 41%) as a dark brown oil. MS (ESI): m/z 767.4 [M+H]$^+$.

VivoTag 645 Compound (12)

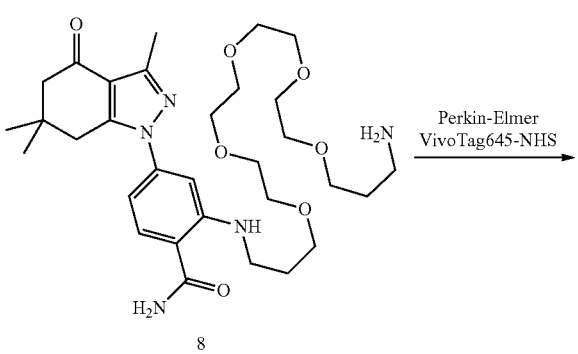

8

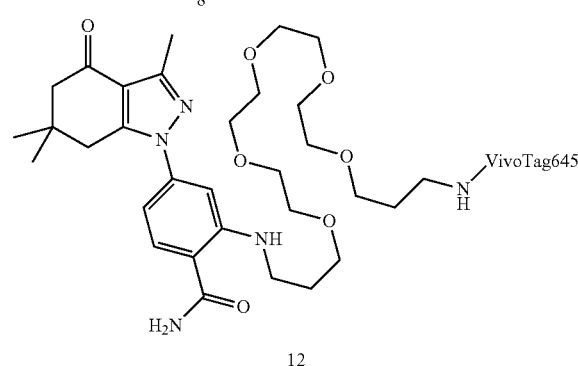

12

Amine 8 (4.5 mg, 7.45 μmol) was dissolved in DMSO (200 μL) and added to VivoTag 645 (Perkin Elmer, 2.5 mg, 1.8 μmol) in its original container and placed back into the freezer overnight. The sample was purified in 3 portions by reverse-phase chromatography and concentrated to give VivoTag 645 compound (12) (~3 mg) as a blue solid. MS (ESI): m/z 1577.5 [M$^-$].

VivoTag 800 Compound (13)

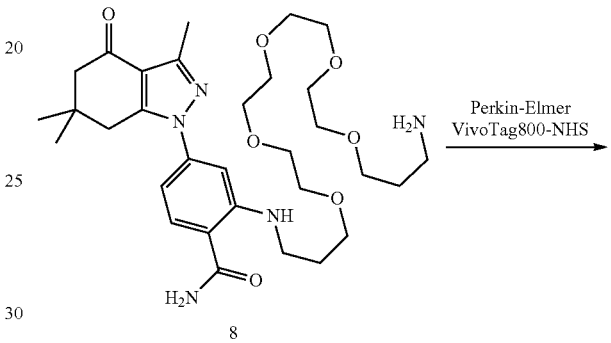

8

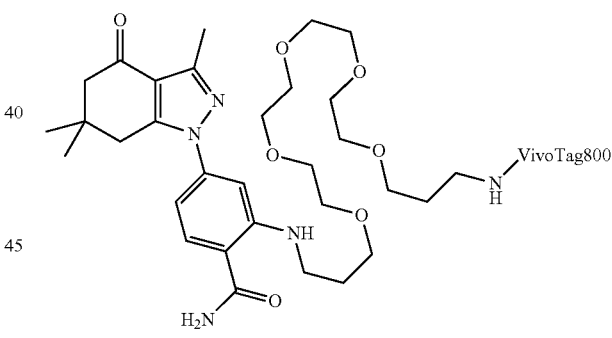

14

VivoTag 800 compound (13). Amine 8 (4.3 mg, 7.2 μmol) was dissolved in DMSO (100 μL) and treated with Hunig's base (10 μL) and added to VivoTag 800 (Perkin Elmer, 5 mg, 3.42 μmol) in its original container. The starting material vial was washed twice with DMSO (100 μL), which was added to the reaction mixture. The mixture was left in an aluminum bag at RT for 30 m, then placed back into the freezer for the 3 d. The sample was purified in 3 portions by reverse-phase chromatography and concentrated to give VivoTag 800 compound (13) (~9 mg) as a blue solid. MS (ESI): m/z 823.7 [M-2]$^{2-}$.

2-((E)-2-((E)-2-((19-((2-carbamoyl-5-(3,6,6-trim-
ethyl-4-oxo-4,5,6,7-tetrahydro-1H-indazol-1-yl)phe-
nyl)amino)-4,7,10,13,16-pentaoxanonadecyl)amino)-
3-((E)-2-(3,3-dimethyl-1-propylindolin-2-ylidene)
ethylidene)cyclohex-1-en-1-yl)vinyl)-3,3-dimethyl-
1-propyl-3H-indol-1-ium (14)

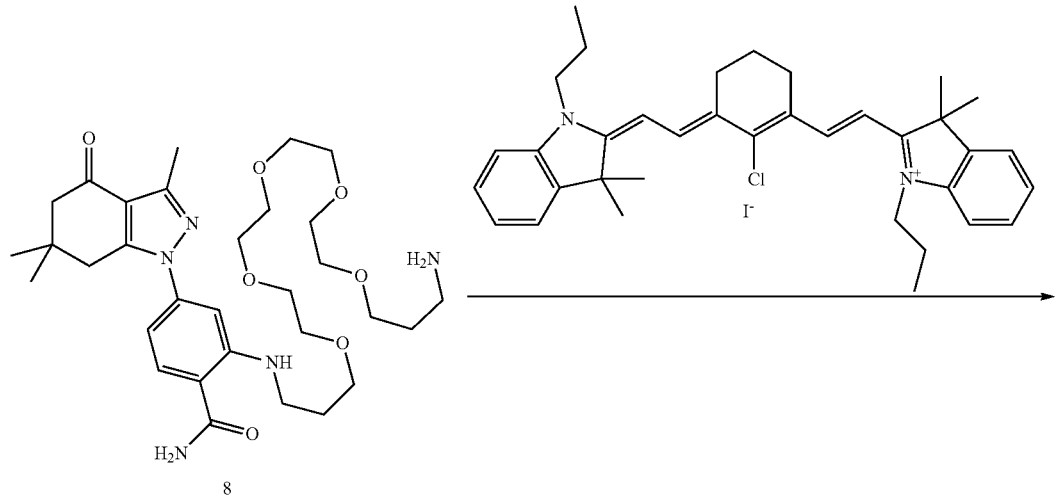

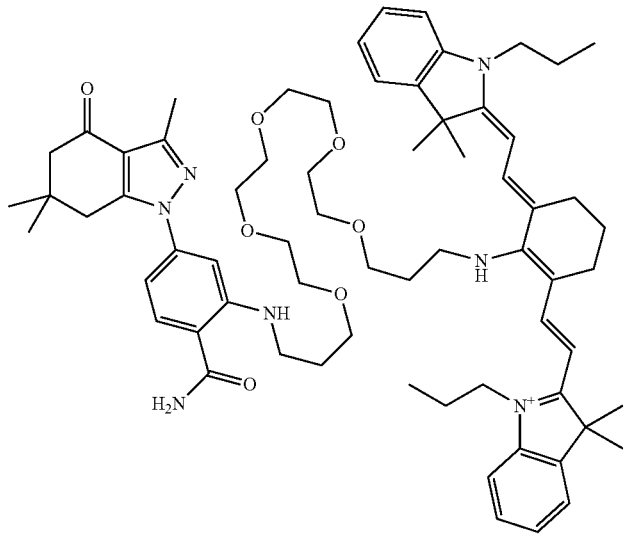

14

Amine 8 (12.1 mg, 20 μmol) was dissolved in DMSO (200 μL) and added to IR-780 iodide (7 mg, 10 μmol) and treated with Hunig's base (15 μL) followed by ethanol (100 μL). The sample was heated for 3 h at 70° C. The entire sample was added to a silica gel column (2.5×20 cm) and chromatographed with $CH_2Cl_2$ (200 mL), $CH_2Cl_2$/MeOH/ $NH_3$ 39/0.9/0.1 (240 mL), 19/0.9/0.1 (240 mL) and 12.3/ 0.9/0.1 (240 mL). The blue band was concentrated to give product 14 (2.4 mg, 22%) as a blue solid. MS (ESI): m/z 554.1 $[M+H]^{2+}$.

N-(19-((2-Carbamoyl-5-(3,6,6-trimethyl-4-oxo-4,5, 6,7-tetrahydro-1H-indazol-1-yl)phenyl)amino)-4,7, 10,13,16-pentaoxanonadecyl)-4-(4-hydroxyphenoxyl)benzamide (15)

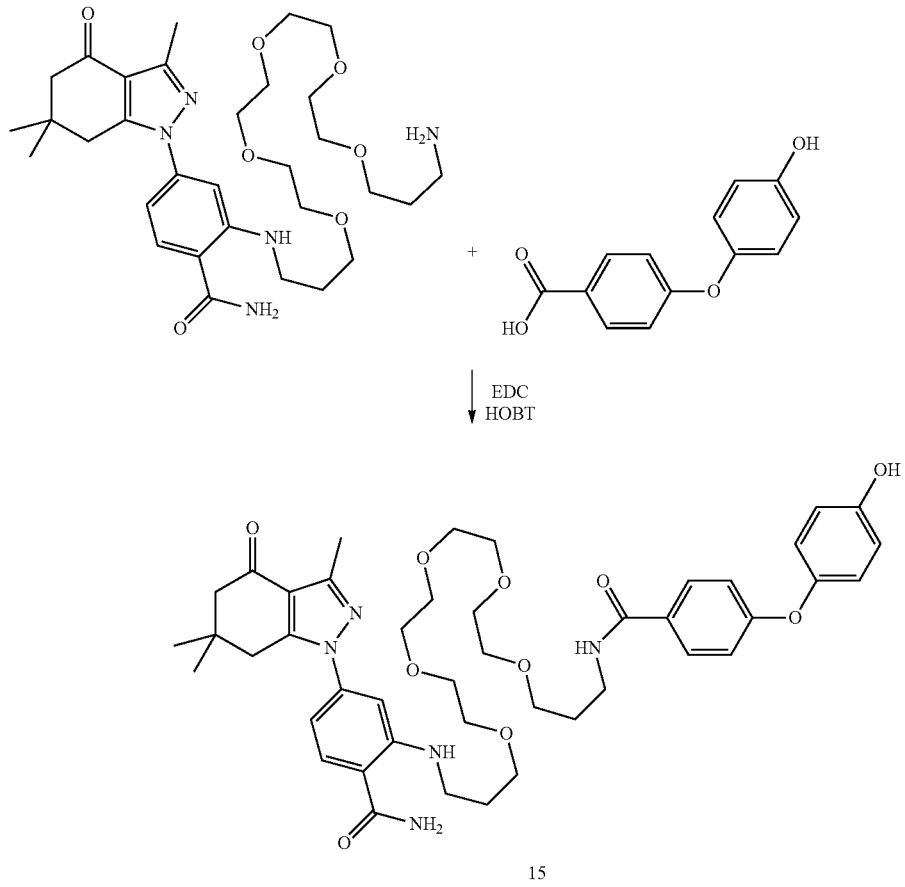

Amine 8 (90 mg, 149 μmol), 4-(4-hydroxyphenoxy)benzoic acid (38 mg, 164 μmol), EDC (43 mg, 224 μmol), HOBT (21 mg, 156 μmol) and 1 chip of DMAP were dissolved in DMF (1 mL) and stirred at RT. Additional acid and EDC were added until starting amine disappeared (by TLC analysis). The mixture was then treated with 1N HCl (5 mL) and extracted with ethyl acetate (5×5 mL). The organic layer was concentrated, dissolved in DMSO and injected on the prep HPLC (50 to 100% methanol, Agilent C-18, 21.1× 25 cm). The product peak was concentrated to give 15 (44 mg, 36%) as a clear glass. (ESI): m/z 816.6 [M+H]$^+$.

The phenol moiety of compound 15 will be iodinated using standard methods to produce the following compounds:

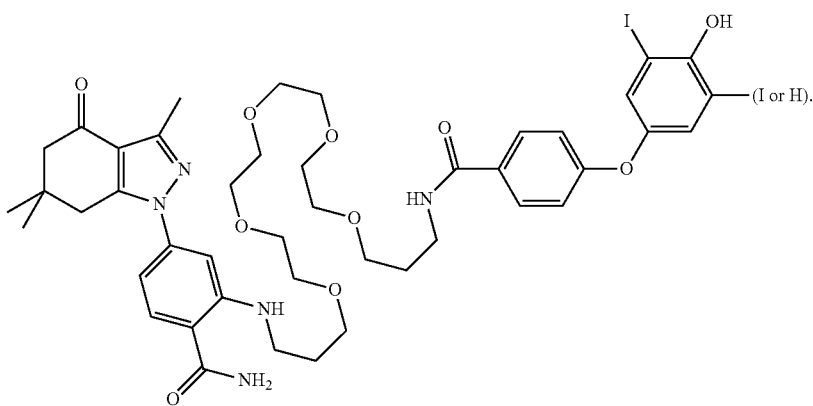

(S)-1-((2-Carbamoyl-5-(3,6,6-trimethyl-4-oxo-4,5,6,7-tetrahydro-1H-indazol-1-yl)phenyl)amino)-24-(4-(((2,4-diaminopteridin-6-yl)methyl)(methyl)amino)benzamido)-21-oxo-4,7,10,13,16-pentaoxa-20-azapentacosan-25-oic acid (16)

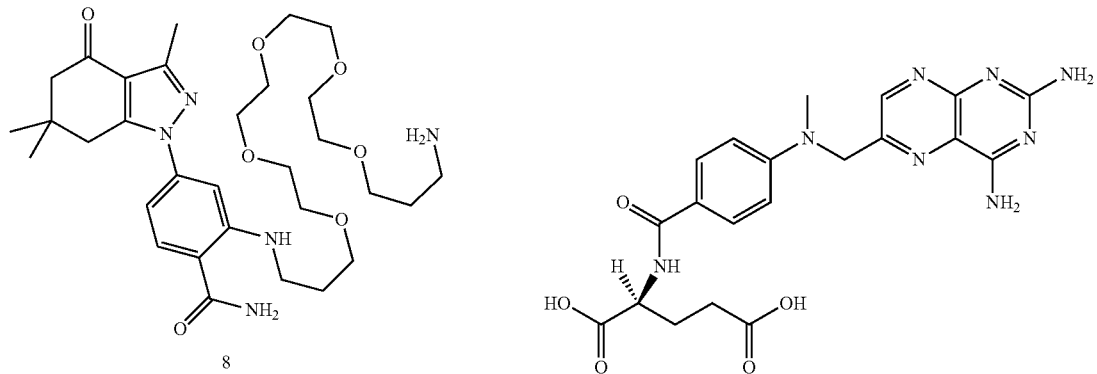

Amine 8 (36 mg, 60 μmol) and methotrexate (MTX, 30 mg, 65 μmol) were dissolved in DMF (0.5 mL) and then treated with EDC (12 mg, 62 μmol) in DMF (150 μL) quickly and stirred at room temperature. After one day, more MTX (6 mg) was added to the mixture followed by more EDC (1.2 mg). After another 2 h the reaction mixture was shot directly onto a prep HPLC (Agilent Prep C-18, 2.5×25 cm, 5 to 100% MeOH w/2% formic acid) and the product collected and concentrated to give product 16 (40 mg, 64%) as a yellow glass.

2-((1-hydroxy-3,6,9,12-tetraoxapentadecan-15-yl)amino)-4-(3,6,6-trimethyl-4-oxo-4,5,6,7-tetrahydro-1H-indazol-1-yl)benzamide (19) and 2,2'-(4,7,10,13,16-pentaoxanonadecane-1,19-diylbis(azanediyl))bis(4-(3,6,6-trimethyl-4-oxo-4,5,6,7-tetrahydro-1H-indazol-1-yl)benzamide) (20)

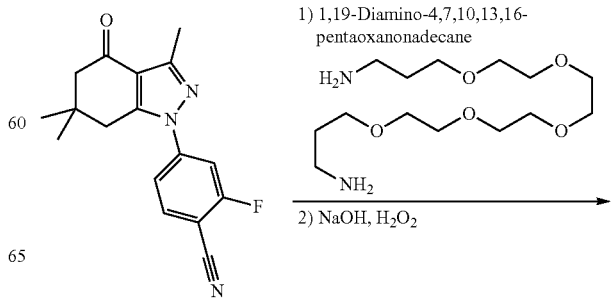

Example 5. Synthesis of PU-H71 Derivatives

N1-(3-(6-amino-8-((6-iodobenzo[d][1,3]dioxol-5-yl)thio)-9H-purin-9-yl)propyl)-4,7,10,13,16-pentaoxanonadecane-1,19-diamine (22)

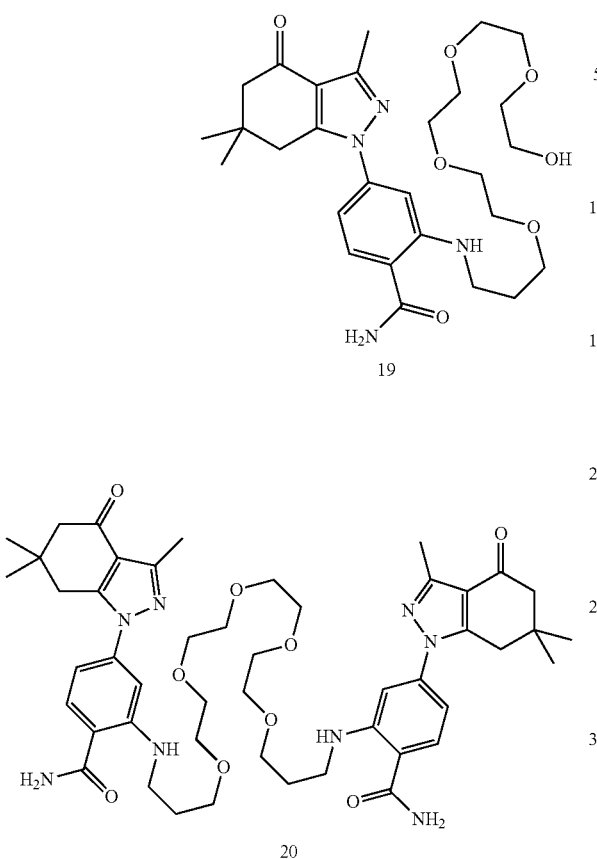

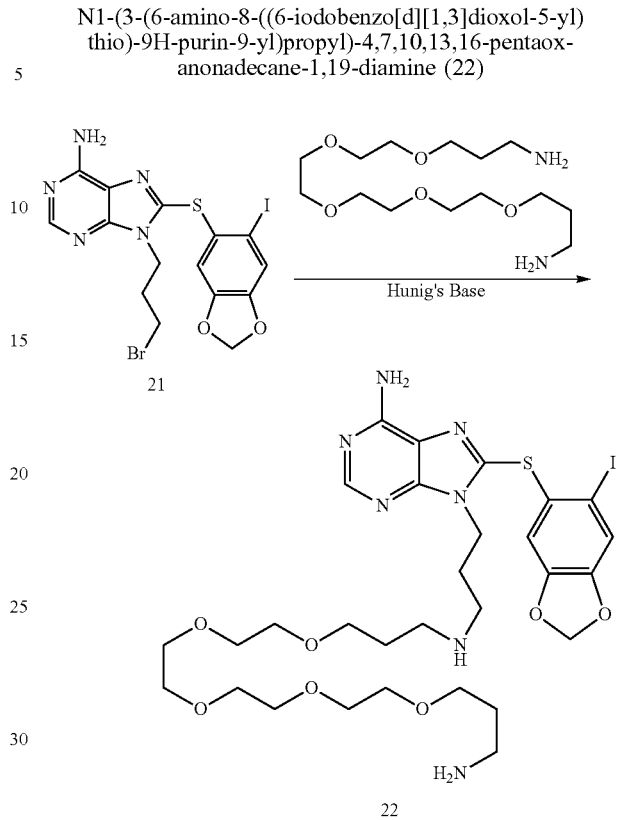

Using the synthesis of Amine 8, two by-products resulting from bis-coupling and a diamine impurity were recovered. The mixture (~100 mg) was dissolved in DMSO (1 mL) and injected on a prep HPLC (PFH-002_078 Prep, 5 to 100% methanol, Agilent C-18, 21.1×25 cm). The early eluting peaks was concentrated to give alcohol 19 (48 mg). (ESI): m/z 547.5 [M+H]$^+$. The later eluting peak was concentrated to give the symmetrical compound 20 (34 mg). (ESI): m/z 899.7 [M+H]$^+$.

9-(3-Bromopropyl)-8-((6-iodobenzo[d][1,3]dioxol-5-yl)thio)-9H-purin-6-amine (21, prepared according to *Bioorg. Med. Chem.* 19, 2603-2614 (2011)) (14 mg, 26 μmol) was treated with 1,19-diamino-4,7,10,13,16-pentaoxanonadecane (24 mg, 79 μmol) in ethanol (1 mL) and DMSO (400 μL). The ethanol was removed under vacuum and the mixture stirred at RT for 1 day. The mixture was purified by preparative HPLC (5 to 100% methanol, 20 mL/m, Agilent C-18, 21.1×25 cm) to give the product 22 (14 mg, 70%) as a clear oil. (ESI): m/z 762.2 [M+H]$^+$.

1-(23-(6-amino-8-((6-iodobenzo[d][1,3]dioxol-5-yl)thio)-9H-purin-9-yl)-4,7,10,13,16-pentaoxa-20-azatricosyl)-3-(3',6'-dihydroxy-3-oxo-3H-spiro[isobenzofuran-1,9'-xanthen]-5-yl)thiourea (23)

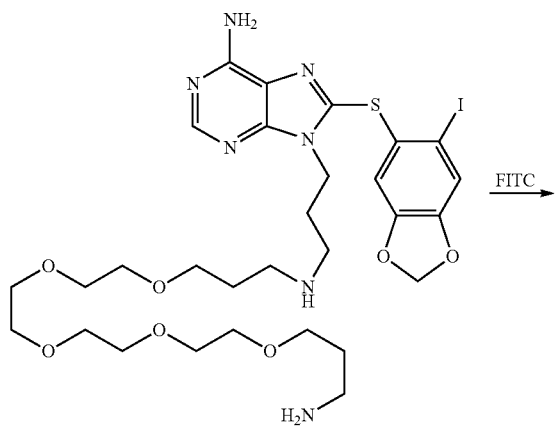

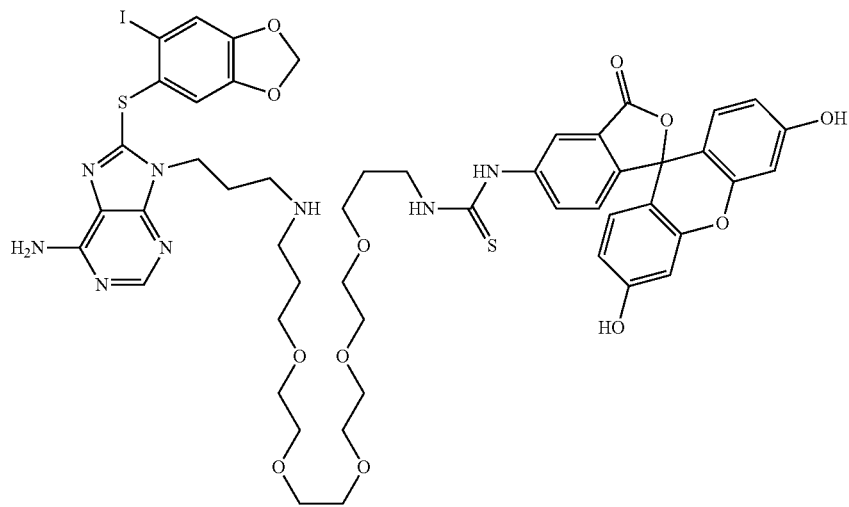

23

Amine (22) (all 14 mg, 18 μmol) was dissolved in ethanol (1 mL) and added to FITC (10 mg, 25.7 μmol). Additional solid persisted so more ethanol (250 μL) was added, followed by DMSO (250 μL) and Hunig's base (25 μL). The mixture was concentrated and purified by preparative HPLC (PFH-003-027Prep, 5 to 100% methanol, 20 mL/m, Agilent C-18, 21.1×25 cm) to give the fluorescent product (23) (16 mg, 75%) as a yellow glass. (ESI): m/z 1151.3 [M+H]$^+$.

Example 6. Synthesis of Compound with a Cleavable Linker (E)-4-((5-(2-((tert-butoxycarbonyl)amino)ethyl)-2-hydroxyphenyl)diazenyl)benzoic acid (17)

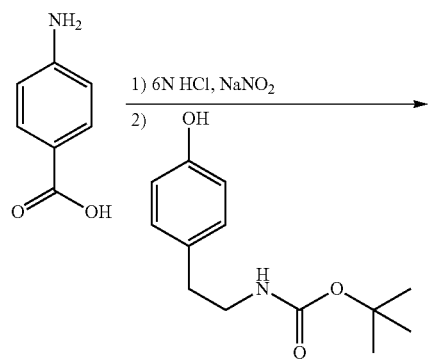

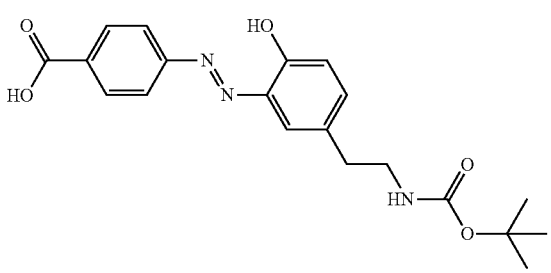

17

4-Aminobenzoate (500 mg, 3.6 mmol) was slurried in 6N HCl (10 mL), cooled to 0° C. and treated slowly with sodium nitrite (629 mg, 9.11 mmol). After stirring for 20 m, the mixture was added slowly to an ice-cooled solution of N-Boc tyramine (865 mg, 3.6 mmol) in saturated sodium bicarbonate solution (40 mL) with added sodium bicarbonate (4 g) and a bit of acetone (~5 mL). The orange reaction slurry was left to stir overnight. The reaction mixture was treated 1N HCl (100 mL) until acidic and then stirred an additional 2 h. The solids were filtered off, washed with water and air dried, then dried under vacuum to give 17 (1.03 g, 73%) as a reddish-orange solid. The product was used as is though it contained a minor impurity by NMR. TLC (9/1 CH$_2$Cl$_2$/MeOH) R$_f$=0.20; $^1$H NMR (DMSO-d$_6$) δ 13.19 (br s, 1H), 10.82 (s, 1H), 8.11 (d, J=8.5 Hz, 2H), 8.05 (d, J=8.5 Hz, 2H), 7.55 (s, 1H), 7.28 (d, J=8.3 Hz, 1H), 7.00 (d, J=8.3 Hz, 1H), 6.88 (t, 1H), 3.12 (m, 2H), 2.67 (t, J=6.8 Hz, 2H), 1.33 (s, 9H); MS (ESI): m/z 384.2 [M]$^-$, 791.4 [2M+Na]$^-$; HRMS (ESI) [M+Na]$^+$ calcd for C$_{20}$H$_{23}$N$_3$O$_5$Na, 408.1536; found 408.1518.

(E)-tert-butyl 3-((4-((19-((2-carbamoyl-5-(3,6,6-trimethyl-4-oxo-4,5,6,7-tetrahydro-1H-indazol-1-yl)phenyl)amino)-4,7,10,13,16-pentaoxanonadecyl)carbamoyl)phenyl)diazenyl)-4-hydroxyphenethylcarbamate (18)

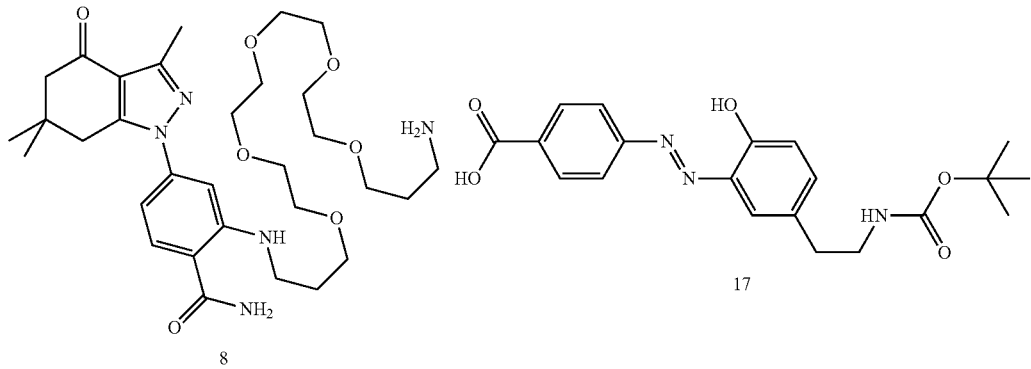

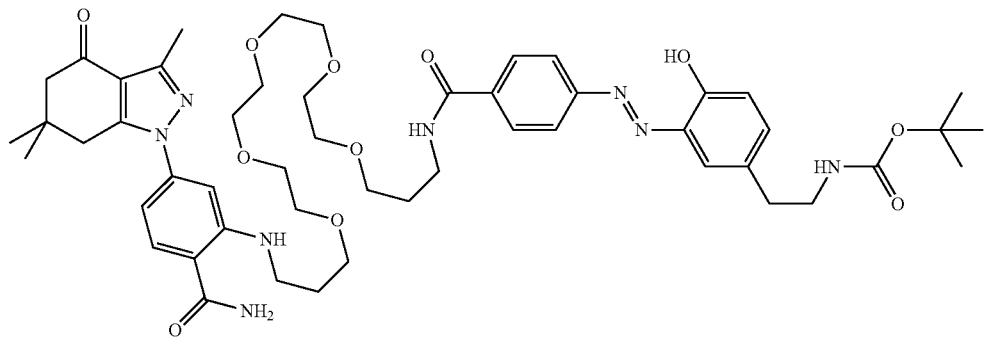

Amine 8 (483 mg, 800 μmol), acid 17 (308 mg, 800 μmol), EDC (161 mg, 840 μmol) and HOBT (113 mg, 840 μmol) and 2 chips of DMAP and were dissolved in CH$_2$Cl$_2$ (10 mL) and stirred at RT for 2 h. The reaction mixture was added to a column and chromatographed (2.5×20 cm, silica gel, CH$_2$Cl$_2$ (300 mL), 9/1 CH$_2$Cl$_2$/MeOH (300 mL), 4/1 CH$_2$Cl$_2$/MeOH (300 mL). The active fractions were combined and concentrated to a frothy glass to give 18 (560 mg, 72%). The hard glass was scraped out to give an orange powder (460 mg). TLC (9/0.9/0.1 CH$_2$Cl$_2$/MeOH/NH$_3$) R$_f$=0.44; $^1$H NMR (DMSO-d$_6$) δ 10.85 (s, 1H), 8.60 (br t, 1H), 8.40 (br t, 1H), 8.02 (br s, 4H), 7.92 (b s, 1H), 7.73 (d, J=8.1 Hz, 1H), 7.55 (s, 1H), 7.27 (d, J=8.1 Hz, 1H), 7.00 (d, J=8.1 Hz, 1H), 6.88 (br t, 1H), 6.76 (s, 1H), 6.66 (d, J=8.1 Hz, 1H), 3.47 (m, 20H), 3.19 (m, 1H), 3.12 (m, 1H), 2.90 (s, 2H), 2.67 (t, 2H), 2.52 (m under DMSO, 2H), 2.38 (s, 3H), 2.31 (s, 2H), 1.77 (m, 4H), 1.33 (s, 9H), 0.99 (s, 6H); HRMS (ESI) [M+H]$^+$ calcd for C$_{51}$H$_{71}$N$_8$O$_{11}$, 971.5237; found 971.523575.

Example 7. Preparation of Affinity Chromatography Resin with a Cleavable Linker (E)

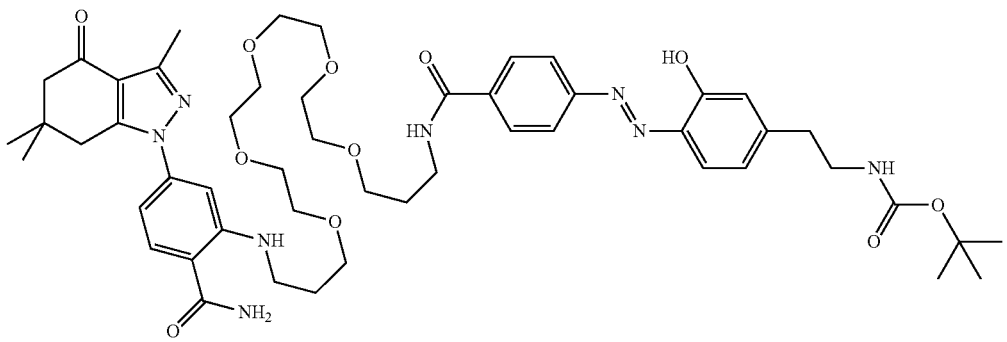

18

1) TFA
2) CNBr-activated Sepharose™ 4B

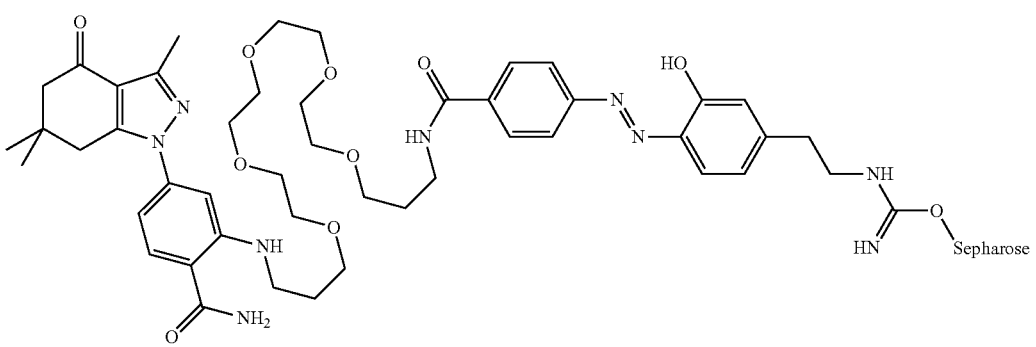

E

High buffer 0.1 M TRIS-HCl, 0.5 M NaCl pH=8
Storage buffer 0.1M $KH_2PO_4$, pH=7.4 w/200 mg $NaN_3$/L CNBr-activated Sepharose™ 4B was obtained from GE Healthcare Life Sciences. The following procedure generally followed GE Healthcare Instructions 71-7086-00 AFA.
Buffers and Solutions:
Swelling solution 1 mM HCl
Coupling buffer 0.1 M $NaHCO_3$, 0.5 M NaCl, pH=8.3
Capping solution 1 M ethanolamine
Low buffer 0.1 M AcOH/NaAcOH, 0.5 M NaCl pH=4

Ligand 18 (25 mg 25.74 μmol) was dissolved in trifluoroacetic acid (1 mL). TLC (9/1/0.1: $CH_2Cl_2$/MeOH/$NH_3$) showed loss of starting material and formation of a lower product, corresponding to compound 24 (HRMS (ESI) $[M+H]^+$ calcd for $C_{46}H_{63}H_8O_9$, 871.4713; found 871.4696). The mixture was concentrated, then dissolved in ethanol (5 mL) and concentrated again. The residue was then dissolved in ethanol (5 mL) for addition to the resin.

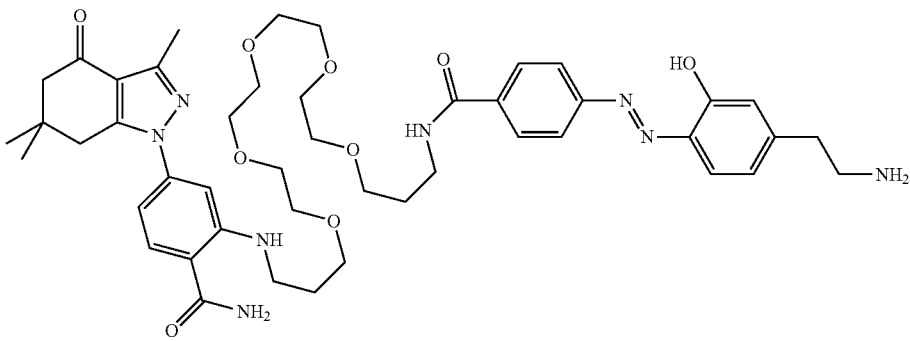

24

In a big 275 mL column, CNBr-activated Sepharose™ 4B (25 g) was swelled in 1 mM HCl (450 ml) and then washed with 1 mM HCl (5 L). The resin was washed with coupling buffer (125 mL) and then slurried with coupling buffer (125 mL). The mixture was then treated with the compound described above. The mixture was tumbled at RT for 4 h. The resin was then drained and washed with coupling buffer (5×125 mL), diluted with more coupling buffer (~125 mL) and treated with capping solution (2 mL) and rotated at RT for 2 h. The solution was drained and washed with 3 rounds of high buffer/low buffer (250 mL ea.) and finally washed with water (250 mL) and transferred in storage buffer (125 mL) to a bottle and stored at 4° C.

Example 8. Synthesis of Other Compounds for Hsp90 Binding and Cell Penetration Comparisons 2-((19-((1-oxo-2,2,6,6-tetramethylpiperidin-4-yl)amino)-4,7,10,13,16-pentaoxanonadecyl)amino)-4-(3,6,6-trimethyl-4-oxo-4,5,6,7-tetrahydro-1H-indazol-1-yl)benzamide (25)

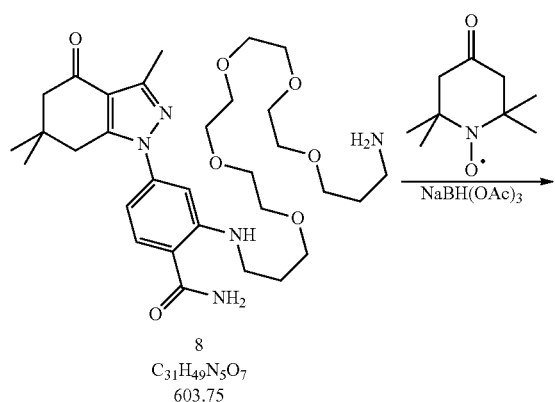

8
$C_{31}H_{49}N_5O_7$
603.75

-continued

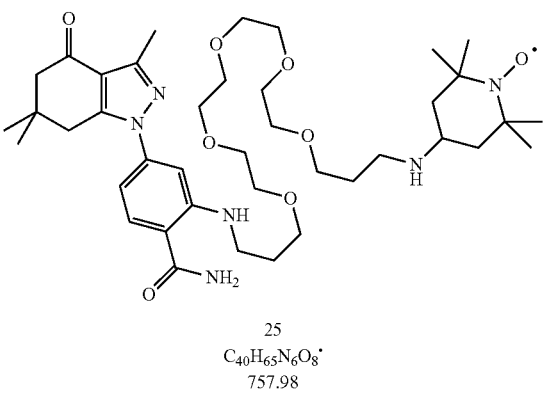

25
$C_{40}H_{65}N_6O_8\cdot$
757.98

Amine 8 (50 mg, 83 μmol) was dissolved in dichloroethane (2 mL) and treated with 4-oxo-TEMPO (14 mg, 83 μmol) followed by sodium triacetoxyborohydride (23 mg, 107 μmol) and stirred at RT overnight. TLC ($CH_2Cl_2$/MeOH/AcOH: 4/1/0.1) showed primarily a new product. The mixture was concentrated then dissolved in DMSO/water and chromatographed (5 to 100% MeOH, Agilent C-18 21.2×250 mm) to give product 25 (39 mg, 63%) as a glass. TLC (9/0.9/0.1 $CH_2Cl_2$/MeOH/$NH_3$) $R_f$=0.55; $^1$H NMR (DMSO-$d_6$) δ spectra not assigned due to broadening by TEMPO; MS (ESI): m/z 758.5 [M+H]$^+$.

2-((19-(ferrocenemethylamino)-4,7,10,13,16-pentaoxanonadecyl)amino)-4-(3,6,6-trimethyl-4-oxo-4,5,6,7-tetrahydro-1H-indazol-1-yl)benzamide (26), 2-((19-di(ferrocenemethylamino)-4,7,10,13,16-pentaoxanonadecyl)amino)-4-(3,6,6-trimethyl-4-oxo-4,5,6,7-tetrahydro-1H-indazol-1-yl)benzamide (27)

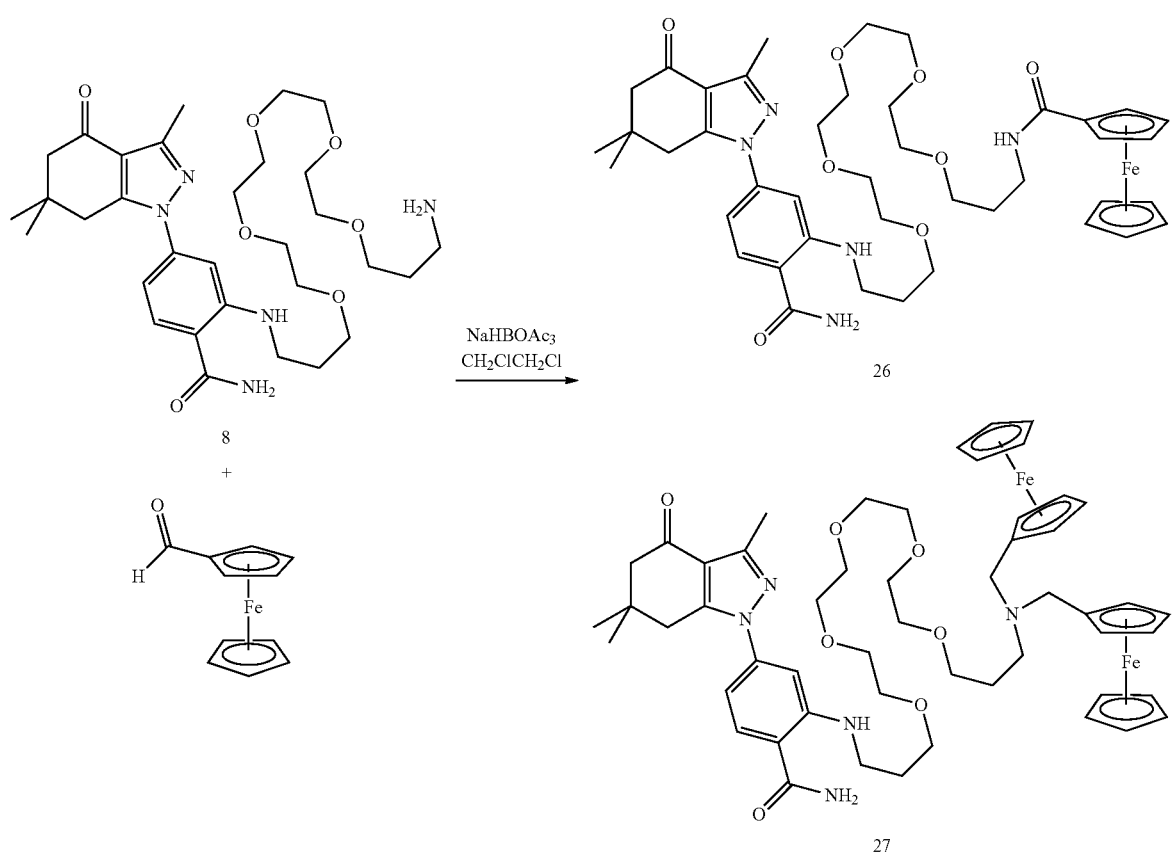

Amine 8 (673 mg, 1.11 mmol) and ferrocene carboxaldehyde (239 mg, 1.11 mmol) were dissolved in dichloroethane (5 mL) and treated with sodium triacetoxy-borohydride (283.5 mg, 1.34 mmol) followed by acetic acid (77 µL). The reaction mixture was stirred over the weekend. The mixture was adsorbed onto silica (3 ®), added to a dry column (1.5×12 cm silica gel) and eluted with 100%, 19/1/0.1, then 9/1/0.1: $CH_2Cl_2$/MeOH/$NH_4OH$ (300 mL ea.) to give the less polar product, 18 (~180 mg) and the more polar product (~650 mg), both as yellow glasses. The products were separately dissolved in DMSO and chromatographed by HPLC (Agilent Prep C-18, 2.5×25 cm, 5 to 100% MeOH w/2% formic acid) to give 26 (490 mg, 54%) and 27 (200 mg, 17%) as viscous yellow glasses. 26. TLC (9/0.9/0.1 $CH_2Cl_2$/MeOH/$NH_3$) $R_f$=0.23; $^1$H NMR ($CDCl_3$) δ 8.52 (s, 1H), 7.98 (br s, 1H), 7.51 (d, J=8.1 Hz, 1H), 6.78 (d, J=1.6 Hz, 1H), 6.59 (dd, J=1.6, 8.1 Hz, 1H), 6.44 (br s, 1H), 4.3 (br s, 2H), 4.16 (br s, 2H), 4.11 (s, 5H), 3.91 (br s, 2H), 3.57 (br m, 20H), 3.28 (br s, 2H), 2.97 (br t, 2H), 2.79 (s, 2H), 5.52 (s, 3H), 2.37 (s, 2H), 1.91 (br m, 4H), 1.08 (s, 6H); MS (ESI): m/z 802.4 [M+H]$^+$. 27 TLC (9/0.9/0.1 $CH_2Cl_2$/MeOH/$NH_3$) $R_f$=0.40; MS (ESI): m/z 1000.5 [M+H]$^+$.

2-(((1r,4r)-4-aminocyclohexyl)amino)-4-(3,6,6-trimethyl-4-oxo-4,5,6,7-tetrahydro-1H-indazol-1-yl)benzamide (28)

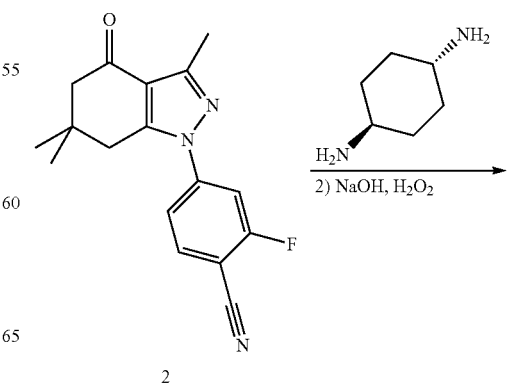

-continued

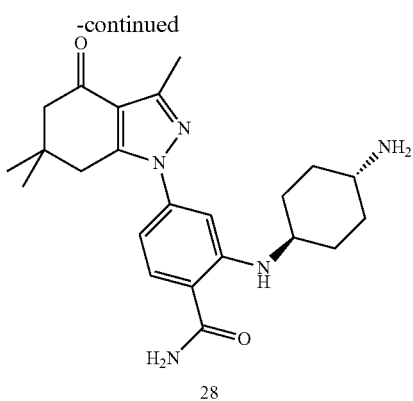

28

A mixture of 2 (500 mg, 1.68 mmol) and trans-1,4-diaminocyclohexane (1.15 g, 10 mmol) and DMSO (1.5 ml) were stirred at RT for 3 days. The mixture was then diluted with ethanol (3 mL), heated to 90° C. and treated with 50% NaOH (12 drops) and then treated, very slowly, a drop at a time, with 30% hydrogen peroxide. After each drop, the reaction foamed up a bit. After 12 drops the reaction mixture was diluted with water (20 mL) and stirred rapidly overnight. A lot of powder fell out and was filtered off, washed with water and air dried to give 28 (689 mg. 100%) as an off-white powder. MS (ESI): m/z 410.3 [M+H]+.

(1r,4r)-4-((2-carbamoyl-5-(3,6,6-trimethyl-4-oxo-4,5,6,7-tetrahydro-1H-indazol-1-yl)phenyl)amino)-N,N,N-trimethylcyclohexanaminium (29)

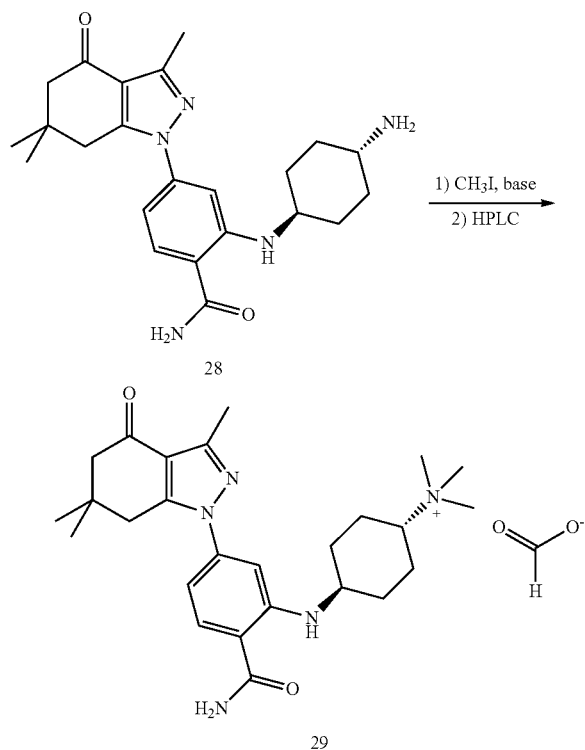

A mixture of 28 (100 mg, 244 μmol) and methyl iodide (208 mg, 1.5 mmol) were dissolved in methylene chloride (2 mL) containing solid sodium bicarbonate (123 mg, 1.5 mmol) and stirred at RT. With monitoring by LC/MS, additional methyl iodide (total 1.6 mL), sodium bicarbonate (123 mg) and DMF (500 μL) were added over 4 days until some tetra-methylation was detected. The sample was concentrated then diluted with DMSO and water to give a milky solution which was injected on the Prep HPLC (PFH-003_002 Prep, 5 to 100% methanol (0.2% formic acid), 20 mL/m, Agilent C-18, 21.1×25 cm). The active fractions were combined and stirred in ethanol to yield a powder which was filtered off to give 29 (28 mg, 23%) as a white powder. MS (ESI): m/z 452.5 [M+H]+.

Example 9. Selectivity Studies

Several media were prepared as described in Example 7, using compounds 6, 7, 8 and 9. These resins were termed A, B, C and D respectively. To prepare the resin in each case, the appropriate compound was added at 1-10 μmol/gram of resin in minimal methanol.

The ability of each resin to selectively capture Hsp90 from pig mammary gland extract, a tissue shown to be high in ATP binding proteins including native forms of Hsp90, GRP94 and TRAP1, was evaluated. The resin was incubated in the protein solution then washed with a high salt buffer. The bound proteins were removed via an SDS boil procedure, separated by SDS-PAGE electrophoresis, located by silver staining and identified using mass spectrometry (MS) sequencing. Selectivity towards Hsp90 was demonstrated by inclusion of 1 mM compound 5 in the tissue extract prior to mixing with the affinity resin. In the case of resin E (Example 7), bound proteins were eluted with 25 mM sodium dithionite in phosphate-buffered saline.

Results are illustrated in FIG. 1. Numbers indicate bands that were sequenced by MS: (1) Fatty acid synthase. (2) Hsp90 (3) Hsp90 (4) Hsp90 proteolytic fragments.

A large number of proteins, including Hsp90, were retained on some resins. The competition experiment, performed by pre-incubating the protein solution with known ligand compound 5, showed clean exclusion of Hsp90 but not other proteins, demonstrating that proteins other than Hsp90 are not client proteins.

Resins A and B showed significant non-specific binding as illustrated in FIG. 1. Resin C showed an intense band of Hsp90, and quenching with compound showed complete blocking of Hsp90 binding as well as several N-terminal fragments. MS analysis demonstrated that all of the recovered proteins were Hsp90 or proteolytic fragments of the protein, suggesting that this resin is selective for Hsp90 over GRP94 and TRAP-1. Resin D was more selective than A and B, although some non-specific binding was observed.

Following exposure of resin E to pig mammary gland extract and treatment with 25 mM sodium dithionite, the eluted proteins were identified by MS. The retained protein profile (FIG. 1, lane E) was essentially identical to resin C, except that the proteins were recovered using non-denaturing conditions.

Example 10. Additional Selectivity Studies

To further explore the selectivity, the elution of pig mammary gland proteins from gamma phosphate linked ATP Sepharose was studied with compound 8, as well as known potent Hsp90 inhibitors PU-H71 (Caldas-Lopes et al. *Proc. Natl. Acad. Sci. USA* 106(20), 8368 (2009)) and SNX-2112 (Chandarlapaty et al. *Clin. Cancer Res.* 14(1) 240 (2008)). This ATP resin has been used previously to study purine-binding proteins (Graves et al. *Mol. Pharma-* col. 2002, 62, 1364) and to discover novel Hsp90 inhibitors (Huang et al. *J. Med. Chem.* 2009, 52, 4288.)

Figure 2:
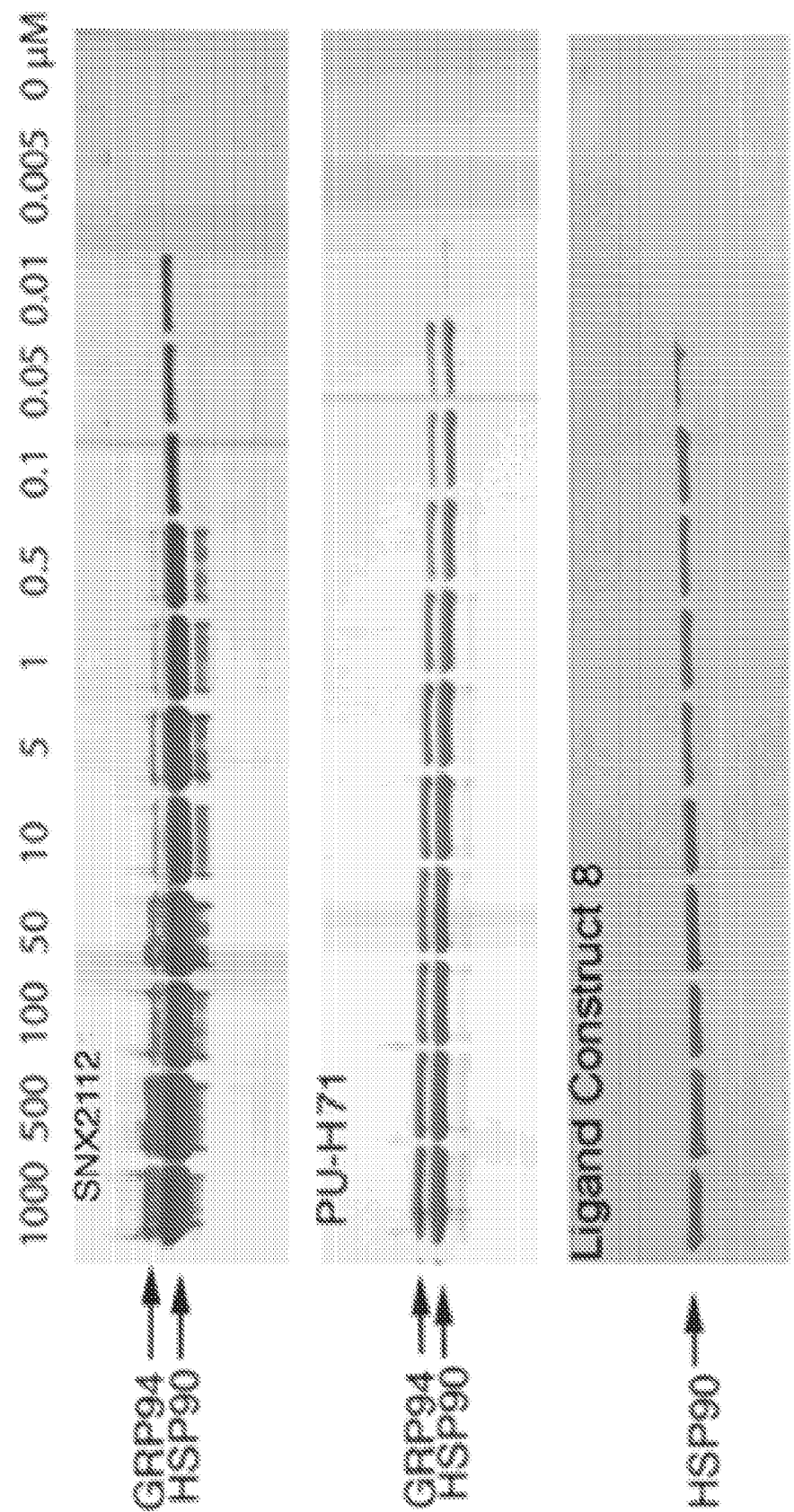
FIG. 2 is an SDS-PAGE silver stain showing elution of pig mammary gland proteins from ATP-Sepharose media with a compound described herein (8) and two known Hsp90 inhibitors.

The ATP resin was charged with the pig mammary gland extract and aliquots were distributed into individual wells. Proteins eluted from the wells with increasing amounts of indicated compound were analyzed as described above; results are illustrated in FIG. 2. Compound PU-H71 demonstrates strong potency towards both Hsp90 and GRP94, whereas SNX-2112 shows weaker affinity for GRP94. Compound 8 shows essentially no elution of GRP94.

Example 11. Additional Selectivity Studies

Figure 3:
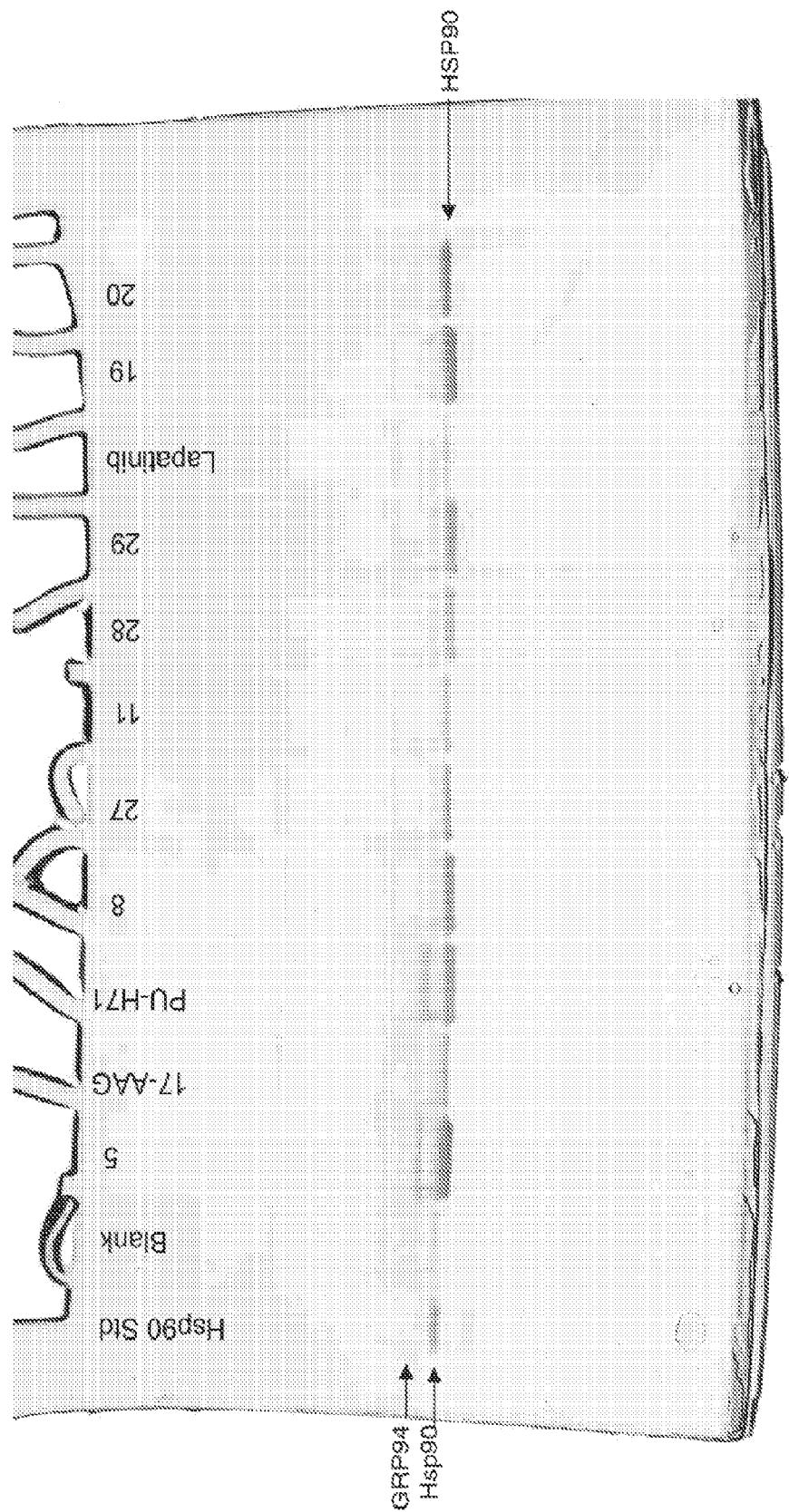
FIG. 3 is an SDS-PAGE silver stain showing elution of pig mammary gland proteins from ATP-Sepharose media with various compounds.

The purinome was captured from pig mammary gland extract as described (Hughes et al., *Bioorg Med Chem.* 2012, 20(10):3298-3305) on gamma phosphate linked ATP Sepharose. Following extensive washing with physiological buffers to remove non-specifically associated proteins, the resin was divided equally and interrogated with the indicated compounds in parallel as described (Hughes et al 2012). All eluted proteins were characterized by SDS-PAGE and silver staining, and then identified by mass spectrometry. Results are illustrated in FIG. 3. The experiment shows that compounds 5, 17-AAG (Schulte et al. *Cancer Chemoth. Pharm.* 42(4), 273 (1998)) and PU-H71 have specificity for both Hsp90 and GRP94, whereas compounds 8, 27, 11, 28, 29, 19, 20 only recognize Hsp90. Key: GRP94, glucose regulated protein 94; Hsp90, heat shock protein 90; LAPT, lapatinimb; Hsp90 STD, purified Hsp90; 17-AAG, derivatized form of geldanamycin, BLK, vehicle control consisting of buffer containing 10% DMSO used to solubilize all compounds included in the test.

Example 12. Evaluation of Compound 10 in Cancer Cells

Figure 4:
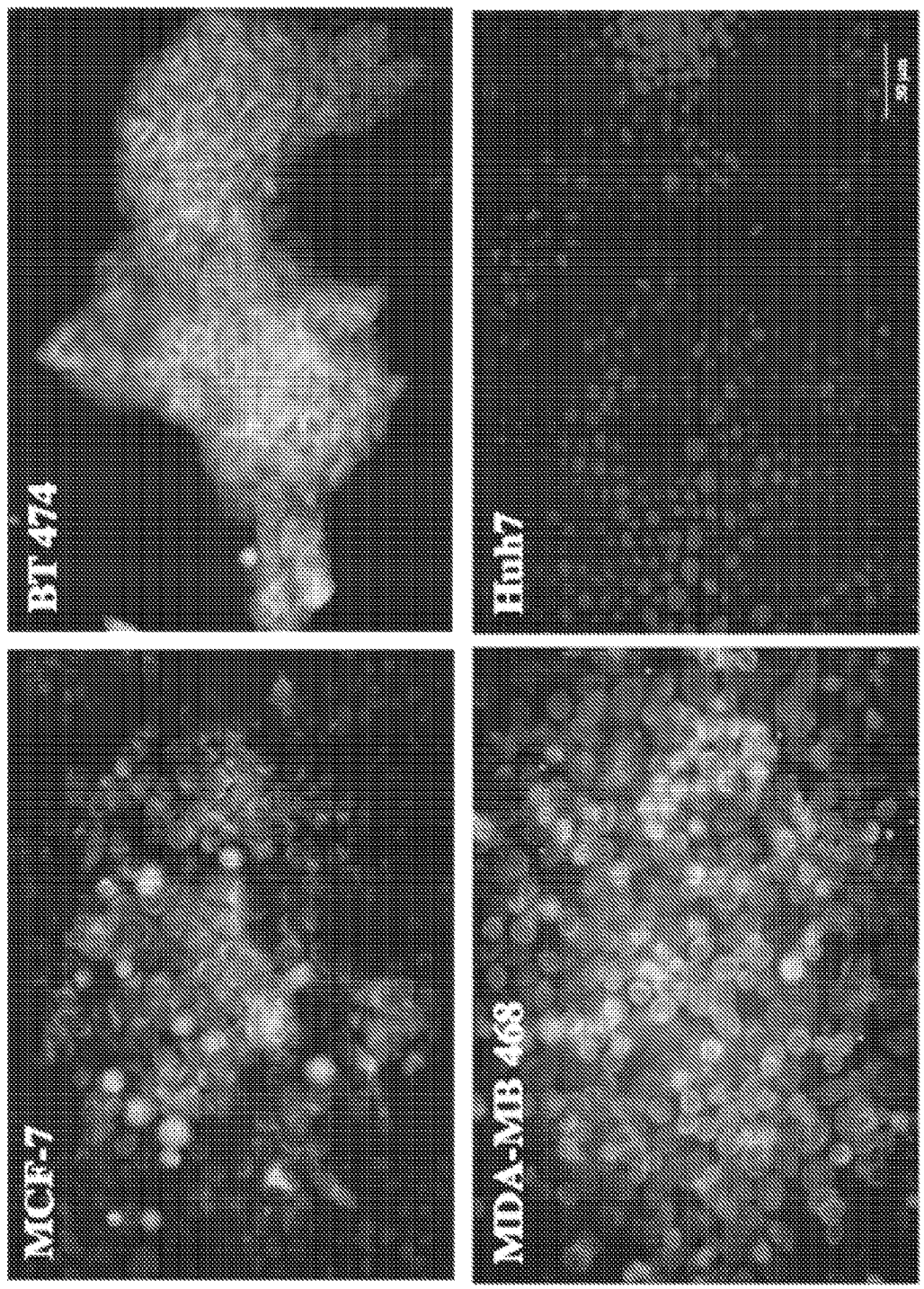
FIG. 4 represents fluorescence microscopy images of cancer cell lines treated with a compound described herein (10).

In one experiment, the fluorescein compound 10 was applied at micromolar concentrations to four types of tumor cells. As illustrated in FIG. 4, the cell lines MCF-7, BT474 and MDA-MB 468, which are metastatic forms of human breast cancer, take up the probe readily. The Huh7 cell line, a human liver non-metastatic cell line, does not absorb the probe. The probe (10) fluoresces to give green staining in images obtained; in FIG. 4, the green staining appears white. DAPI staining shows the nucleus in blue in images obtained; in FIG. 4, the blue staining appears gray.

Figure 5:
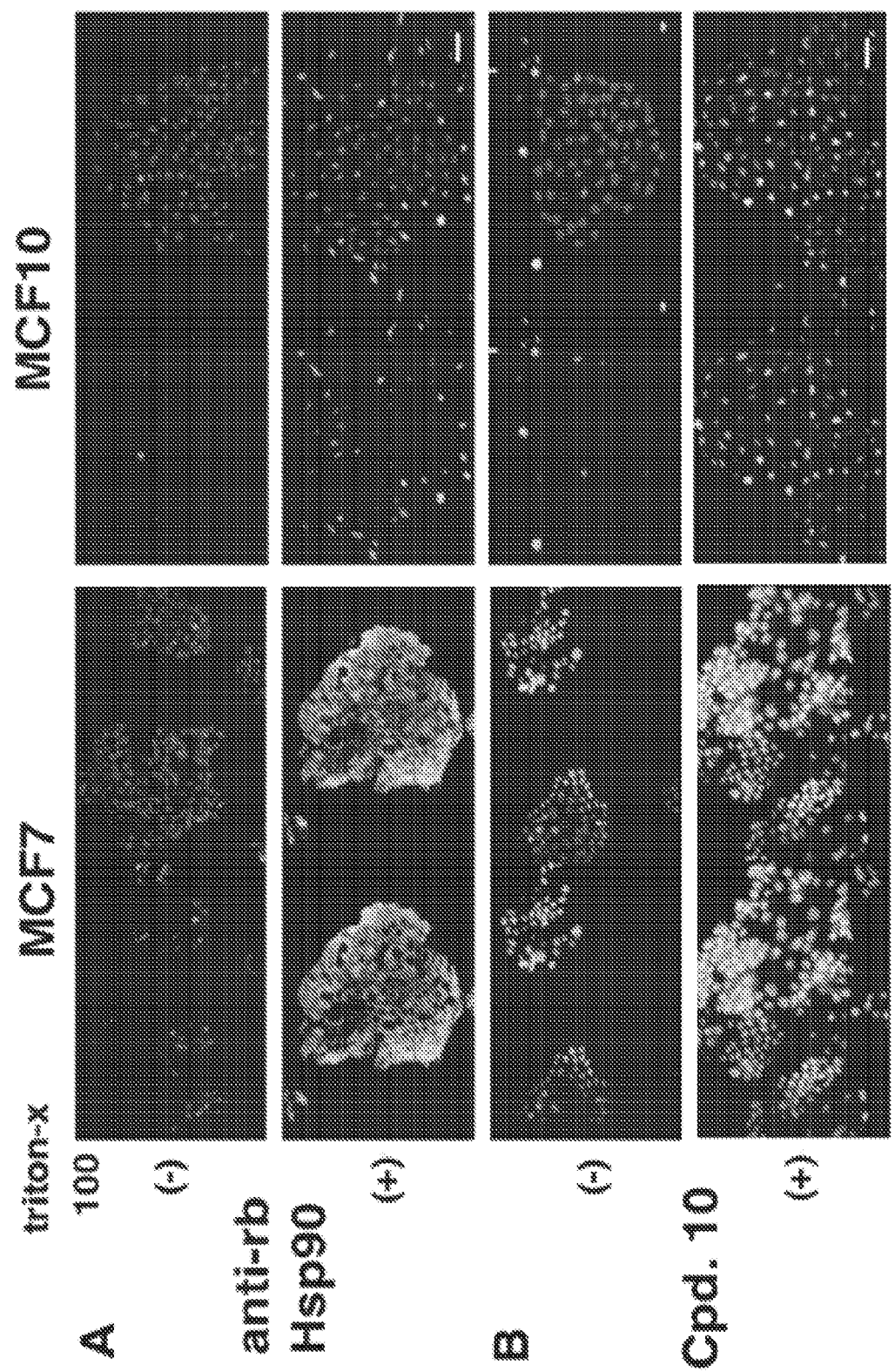
FIG. 5 shows fluorescence microscopy images of metastatic cancer cells and benign cells treated with: (A) an anti-Hsp90 antibody; and (B) compound 10.

In another experiment, MCF7 (metastatic) and MCF10 (benign) cells were treated with an Hsp90 antibody±membrane permeabilization with Triton X 100. As shown in FIG. 5A, in non-permeabilized cells the antibody recognizes surface Hsp90 in MCF7 cells but not in MCF10 cells. After permeabilization the antibody recognizes intracellular Hsp90. Significantly more Hsp90 staining is observed in the MCF7 line. The experiment was also performed using fluorescein compound 10. As shown in FIG. 5B, the probe enters and detects Hsp90 in MCF7 cells, but not in MCF10 cells. The probe also detects more intracellular Hsp90 in MCF7s following permeabilization compared with MCF10s consistent with increased expression of Hsp90. These results suggest up-regulation of Hsp90 in metastatic cells only. In FIG. 5 the green staining from compound 10 fluorescence appears white, while blue from the DAPI-stained nuclei appears gray.

Figure 6:
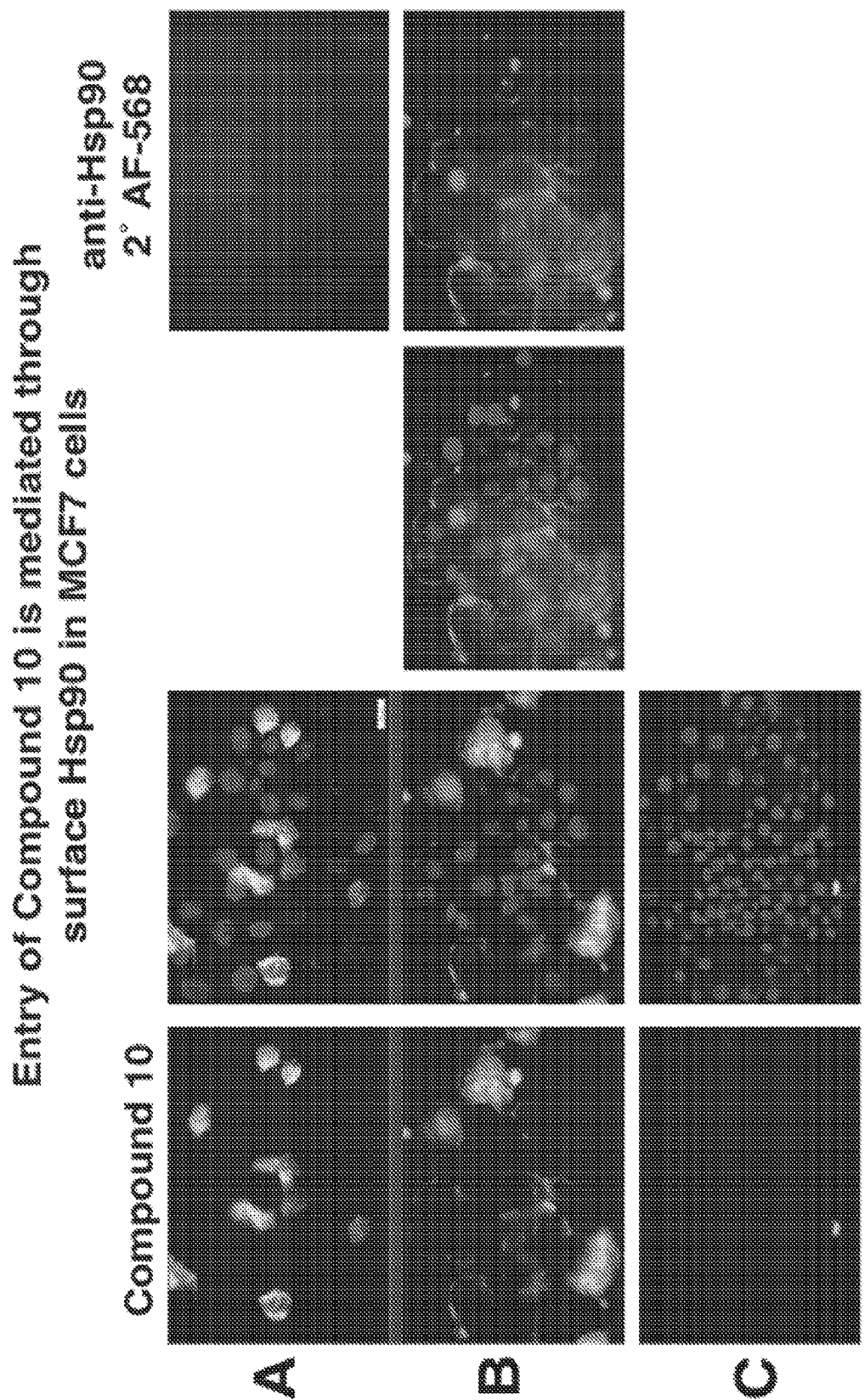
FIG. 6 shows fluorescence microscopy images of MCF7 cells treated with compound 10, in the presence or absence of an anti-Hsp90 antibody, and an Hsp90-binding compound.

As shown in FIG. 6A, compound 10 was added to MCF7 cells alone. In FIG. 6B, the compound was added in the presence of an antibody to Hsp90. The antibody prevents internalization of surface 90 causing the probe to accumulate at the membrane. In FIG. 6C, compound 5 competes away the fluorescence signal. DAPI (blue) highlights the nucleus of the cell. In FIG. 6 the green staining from compound 10 fluorescence appears white, while blue from the DAPI-stained nuclei appears gray.

Example 13. Labeling of MDA-MB-468 Tumor Cells in NOD/SCID Mice

Figure 7A:
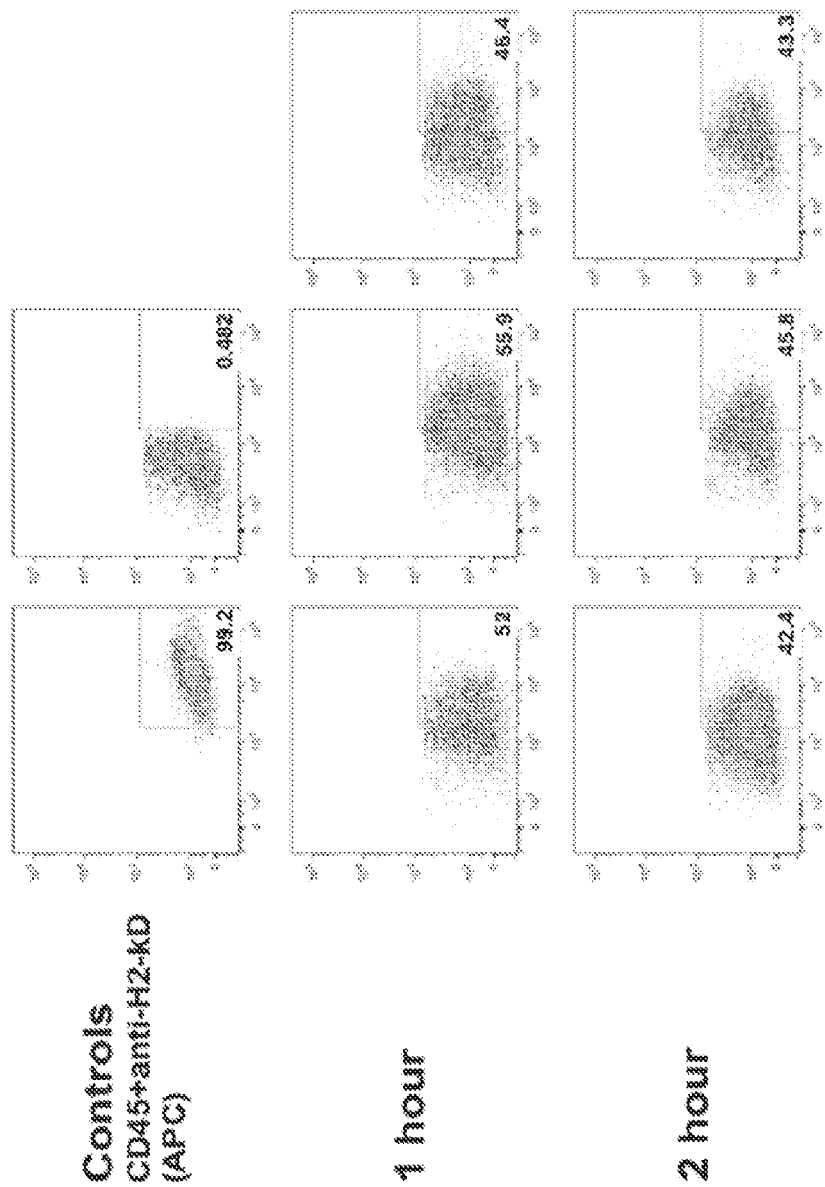
FIGS. 7A and B show labeling of MDA-MB-468 tumor cells in NOD/SCID mice.

MDA-MB-468 tumor-bearing NOD-SCID mice were ip injected with compound 10 (1 mg/mouse, in 100 µl of DMSO). After 1 and 2 hours, mice were sacrificed and tumors and spleens were harvested. Tumors were digested with collagenase/hyarulonidase/Dnase for 1 hour, and ficolled, and washed, then stained with anti-mouse CD45+ anti-H2-kd) (APC). Tumor cells were analyzed by flow cytometry, acquired by LSRII for FITC color compound 10 and mouse lineage expression. Lineage negative cells were analyzed for compound 10 labeling (% positivity is shown in each dot plot). Results are illustrated in FIG. 7A.

Figure 7B:
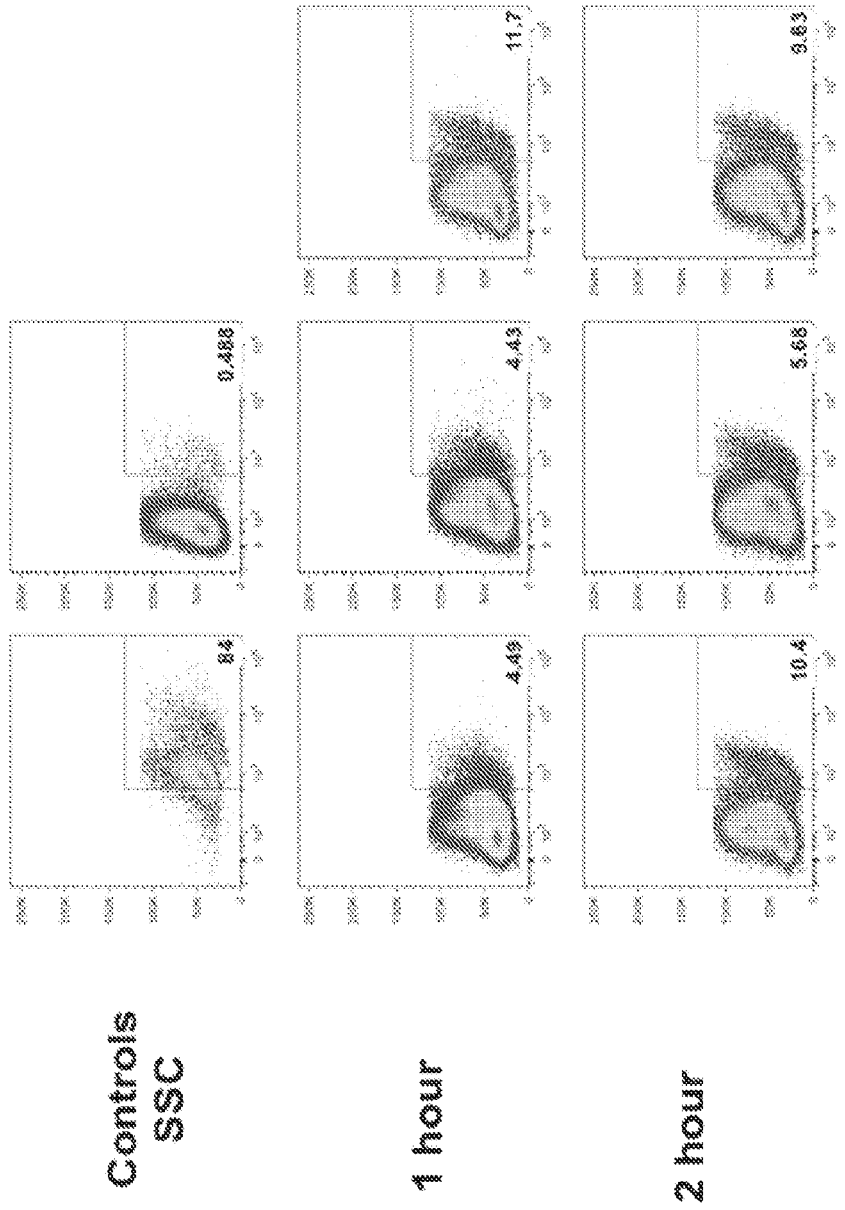

Spleen were minced and passed through the strainer. Splenocytes were acquired as described above to analyze compound 10 labeling. Results are illustrated in FIG. 7B.

Example 14. Xenografts

Figure 8:
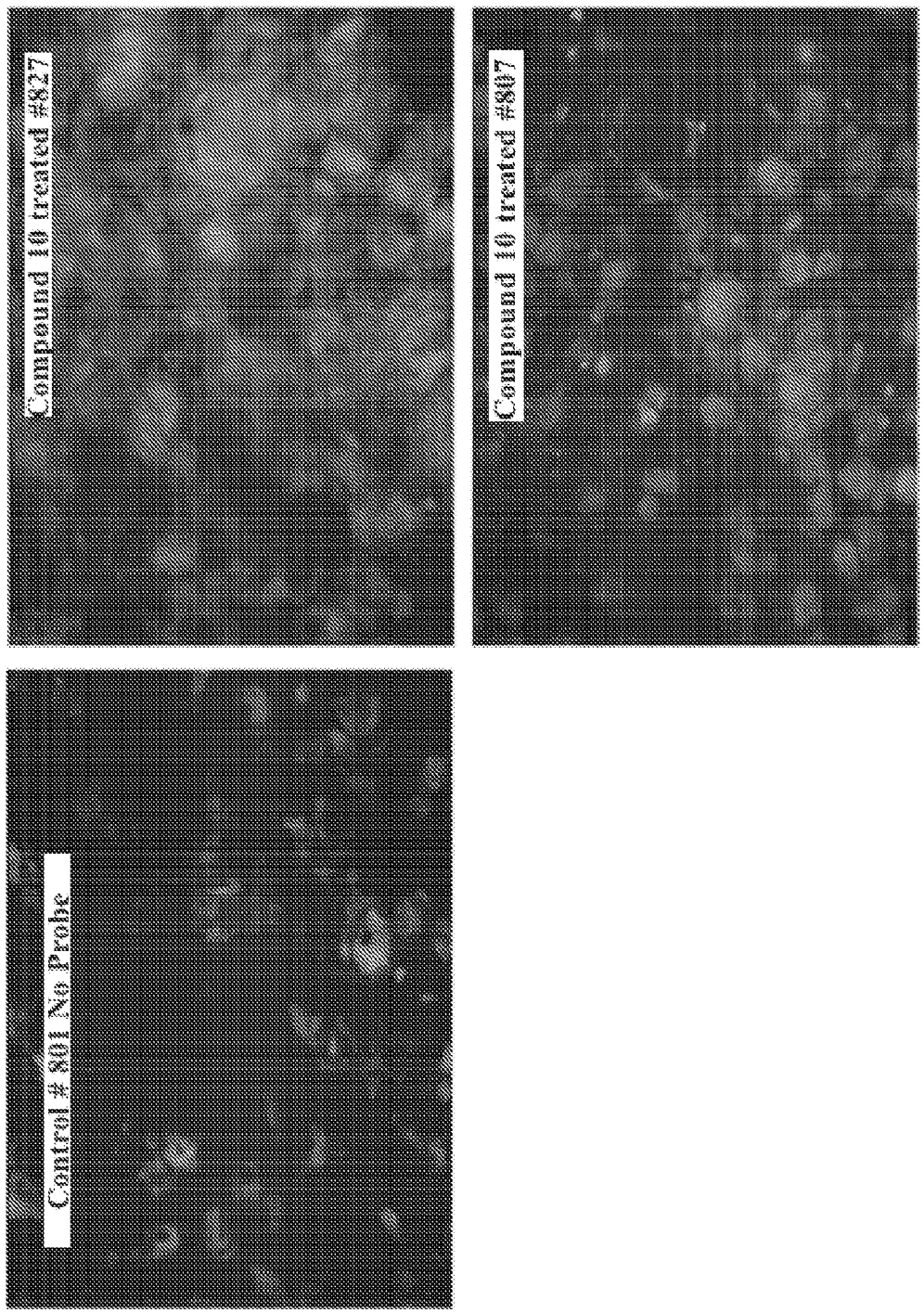
FIG. 8 shows fluorescence microscopy images of xenografts harvested one hour after injection (IP) with compound 10.

FIG. 8 shows images of xenografts (MDA-MB 468) harvested one hour after injection (IP) with compound 10. Tissue slices were prepared from the harvested xenografts and prepared for analysis by confocal analysis. The presence of compound 10 was detected within the tumor cells confirming uptake of the probe in vivo. A tissue slice from the control experiment is shown in which the animal was injected with vehicle alone (DMSO). Only background fluorescence is detected. In FIG. 8 the green staining from compound 10 fluorescence appears white or light gray, while blue from the DAPI-stained nuclei appears dark gray.

Example 15. Competition Experiments

Figure 9:
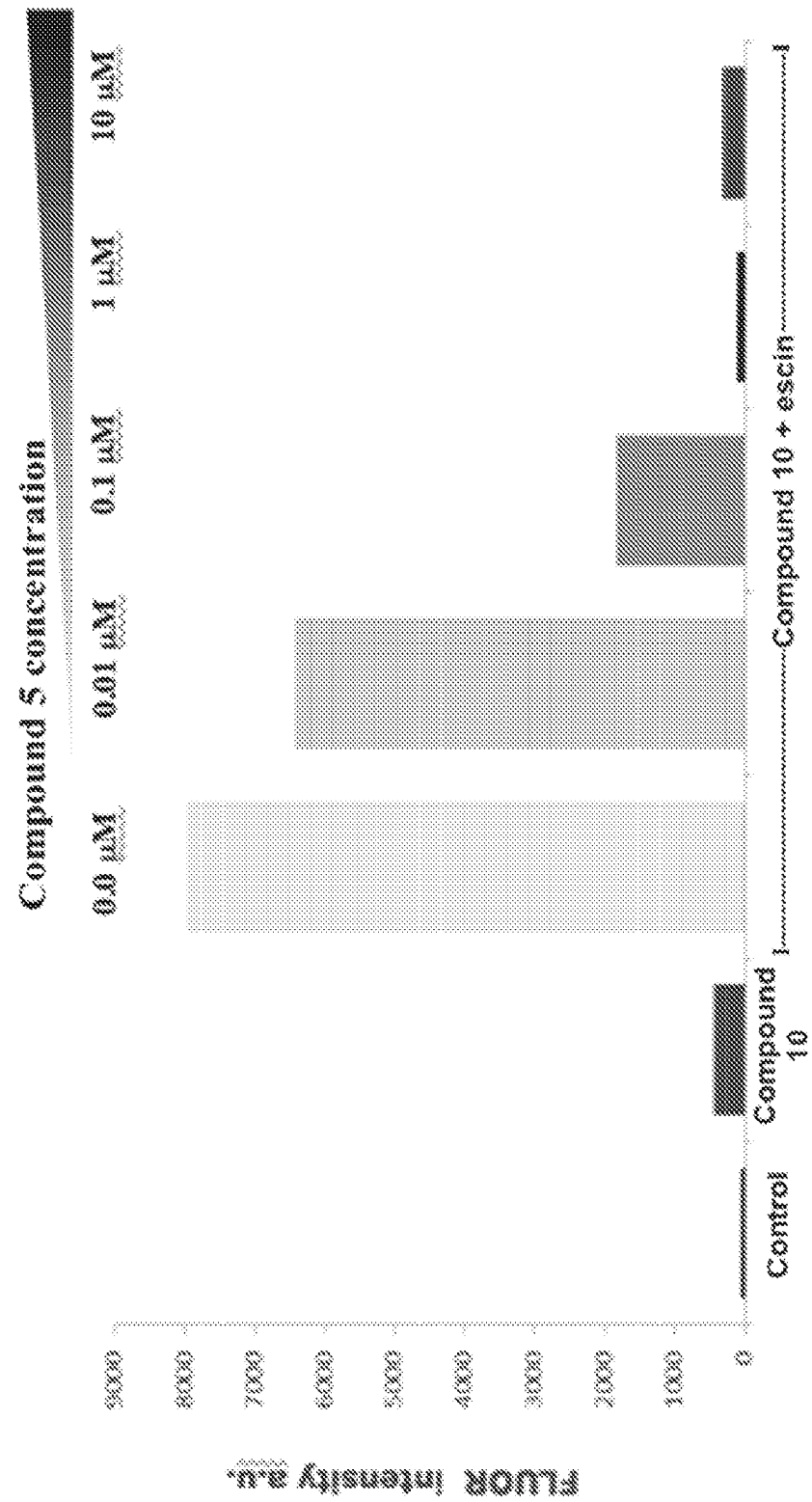
FIG. 9 shows the results of competitive binding experiments between compound 10 and the free parent drug compound 5.

BT474 cells were incubated with varying doses of compound 5 (0 µM, 0.01 µM, 0.1 µM, 1 µM and 10 µM) in the presence of a fixed concentration of compound 10 (10 µM) and a cell permeabilizing agent (escin) for 30 minutes. The cells were then washed to remove the free probe and cell extracts prepared from the homogenized cells. The amount of drug uptake was then measured by fluorescence (Ex488/Em522 nm) in a micro plate fluorescence reader. FIG. 9 shows that the signal from compound 10 can be effectively competed in vivo with the free parent drug, compound 5, in a dose-dependent manner. This data demonstrates that the fluorescence signal measured in cell and xenograft studies is derived from the probe bound to Hsp90.

Example 16. Measuring the Biodistribution of Compound 10 In Vivo in Mouse Xenografts MDA-MB-468 cells (5M cells/mouse) were injected to the flank of NOD/SCID mice. When tumors reached 5-10 mm in diameter, tumor-bearing mice were intraperitoneally injected with compound 10 (1 mg/mouse, in 100 µL of DMSO). After 2, 24, 48 or 72 hours, mice were sacrificed and tumors, livers and spleens were harvested. Tumors and livers were digested with collagenase/hyarulonidase/DNase for 1 hour at 37° C., and ficolled to eliminate debris and dead cells, and then washed. Cells in tumor digest were labeled with anti-mouse CD45-biotin+anti-H2-kD-biotin for 15 min on ice, and then 15 min with streptavidin-APC. Tumor cells were analyzed by flow cytometry to detect fluorescence from compound 10. Mouse lineage negative cells were gated for the analysis. Spleen were minced and passed through the strainer. Splenocytes, liver cells and tumor cells were analyzed by flow cytometry to detect fluorescence from compound 10.

Figure 10A:
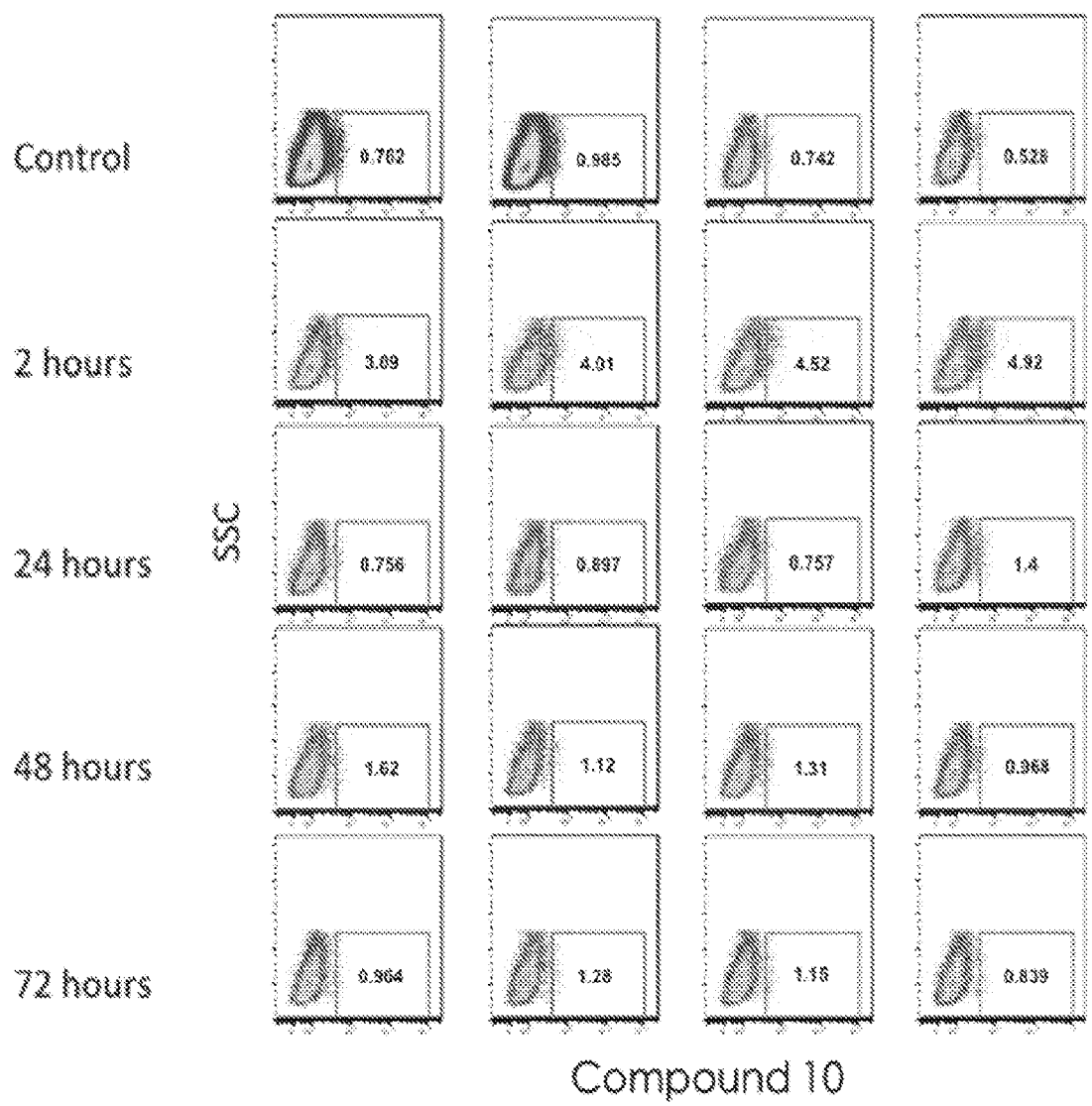
FIG. 10 shows the distribution of compound 10 in mice in (A) splenocytes; (B) liver cells; and (C) tumor cells.

Spleen were minced and passed through a strainer to get rid of aggregations/membranous tissue. Cells were stained with violet viability dye. Viable cells were analyzed for their compound 10 uptake. FIG. 10A shows little accumulation of compound 10 in splenocytes.

Figure 10B:
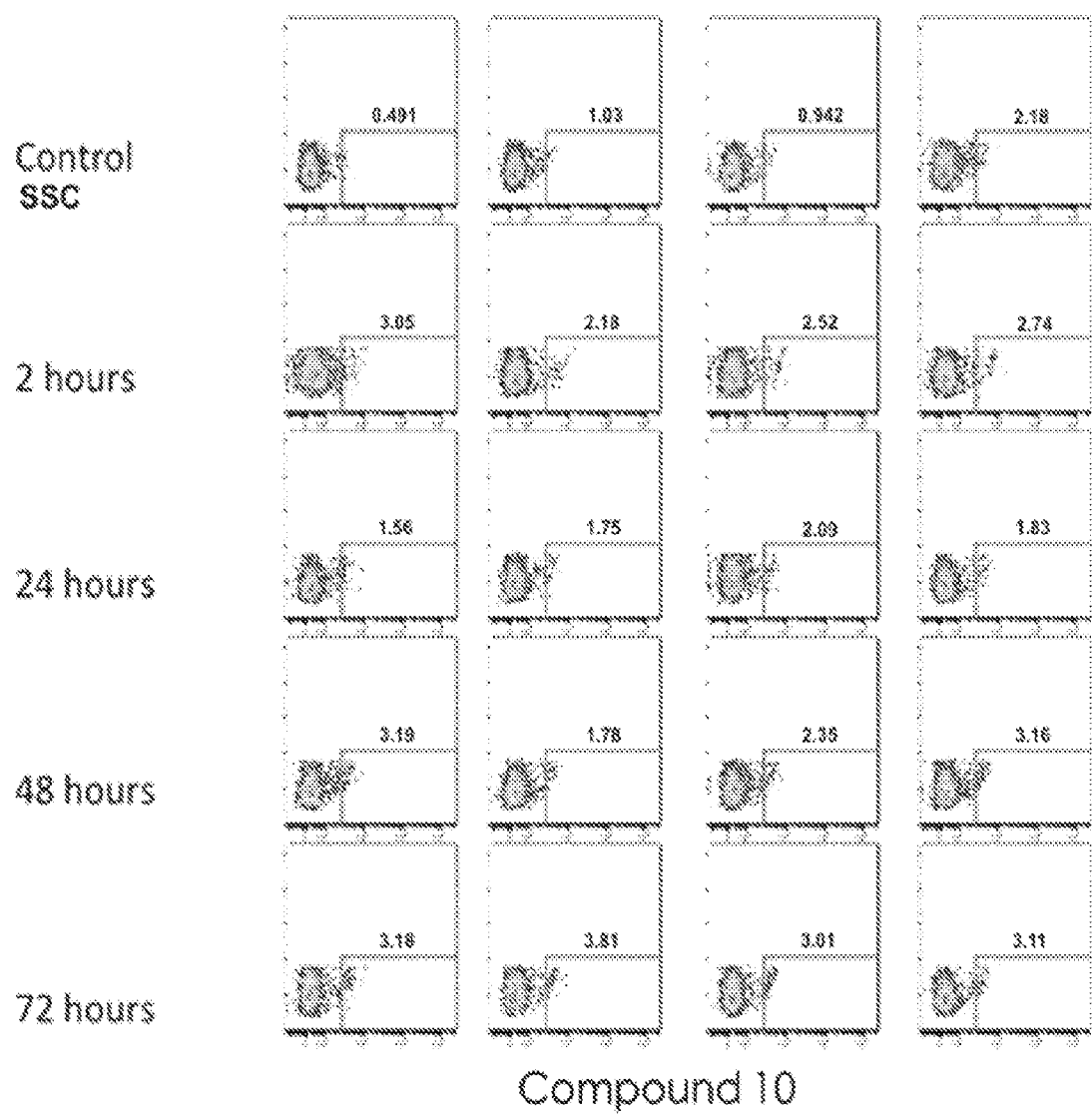

Liver tissues were minced with blades and digested with triple enzyme buffer (collagenase III, hyarulonidase, DNAse) for 1 h at 37° C., and cells were passed through a strainer to get rid of aggregations. Cells were stained with violet viability dye. Viable cells were analyzed for their compound 10 uptake. FIG. 10B shows little accumulation of compound 10 in liver cells.

Figure 10C:
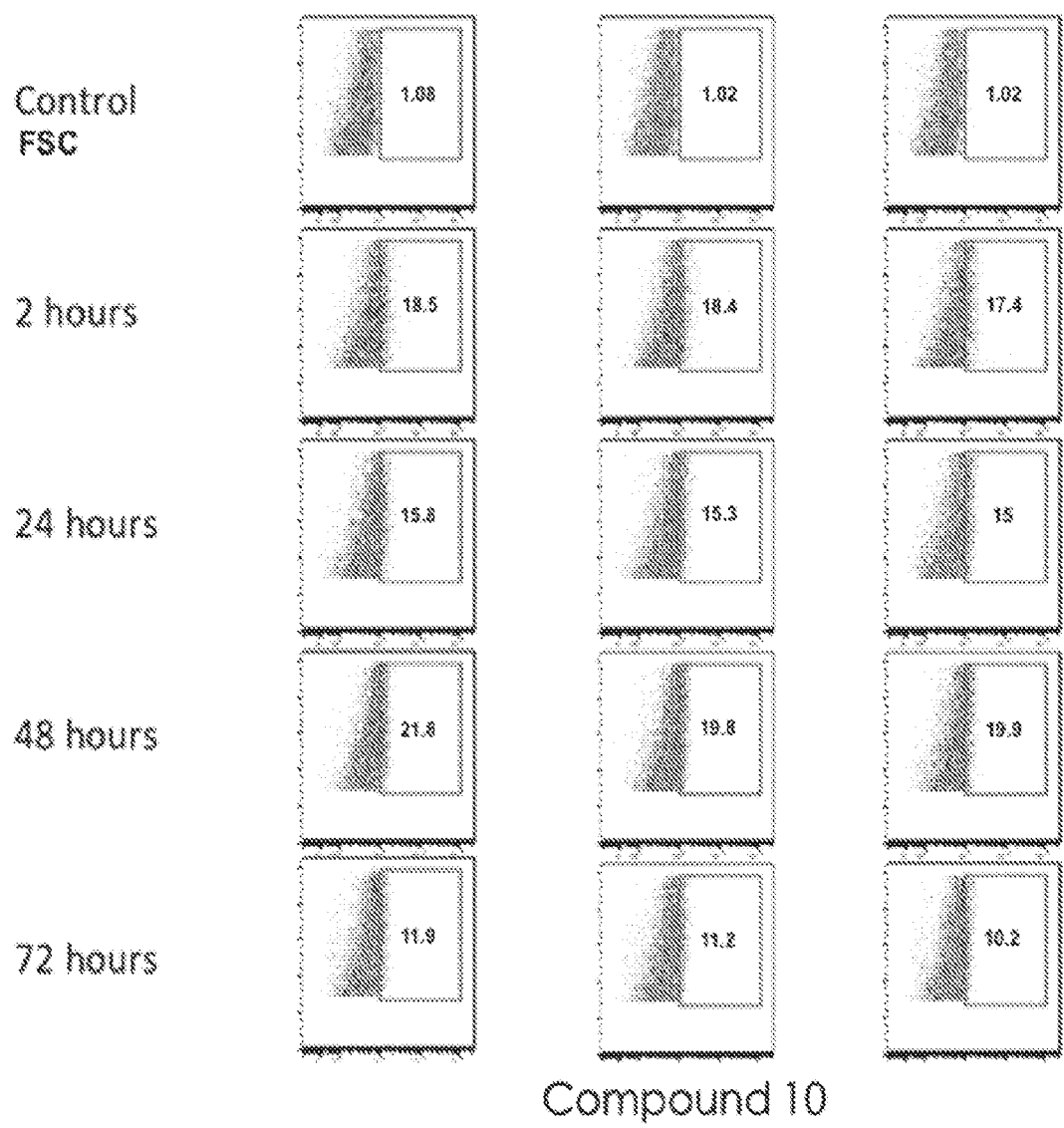

Tumor tissues were minced with blades and digested with triple enzyme buffer (collagenase III, hyarulonidase, DNAse) for 1 h at 37° C., and cells were passed through a strainer to get rid of aggregations. Cells were stained with anti-mouse CD45-biotin/anti-H2-kd-biotin and then streptavidin-APC and violet viability dye. Viable and CD45/H2-kd negative cells were analyzed for their compound 10 uptake. FIG. 10C shows a high degree of accumulation of compound 10 in tumor cells.

Figure 11:
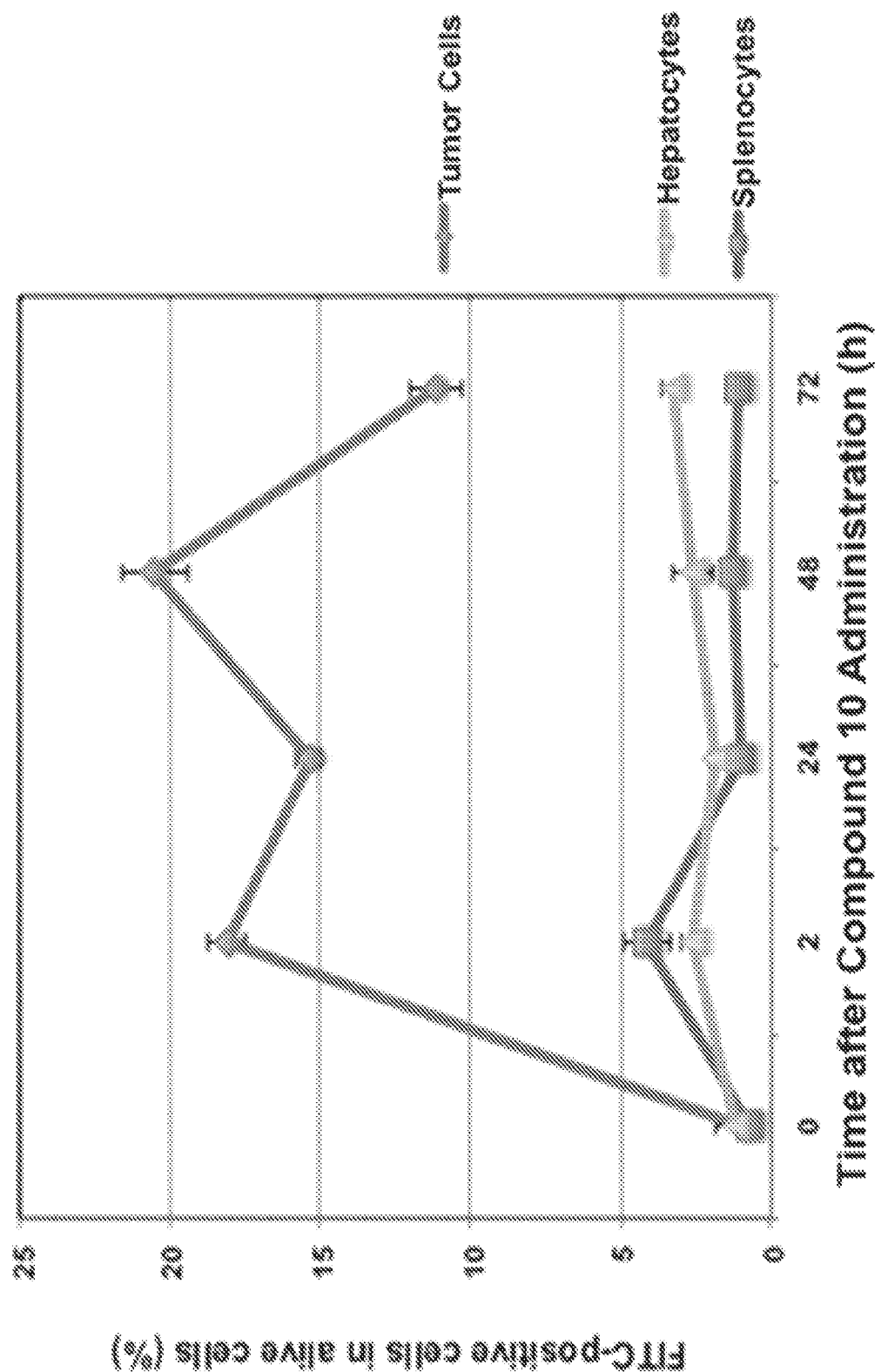
FIG. 11 shows quantitative analysis of the distribution of compound 10 in tumor cells, splenocytes and hepatocytes.

FIG. 11 shows quantitation of compound 10 accumulation in vivo following harvest of the indicated tissues from mice injected with the probe at the indicated time points (5 mice/time point).

Example 17. Tumor Labeling Experiment

Figure 12:
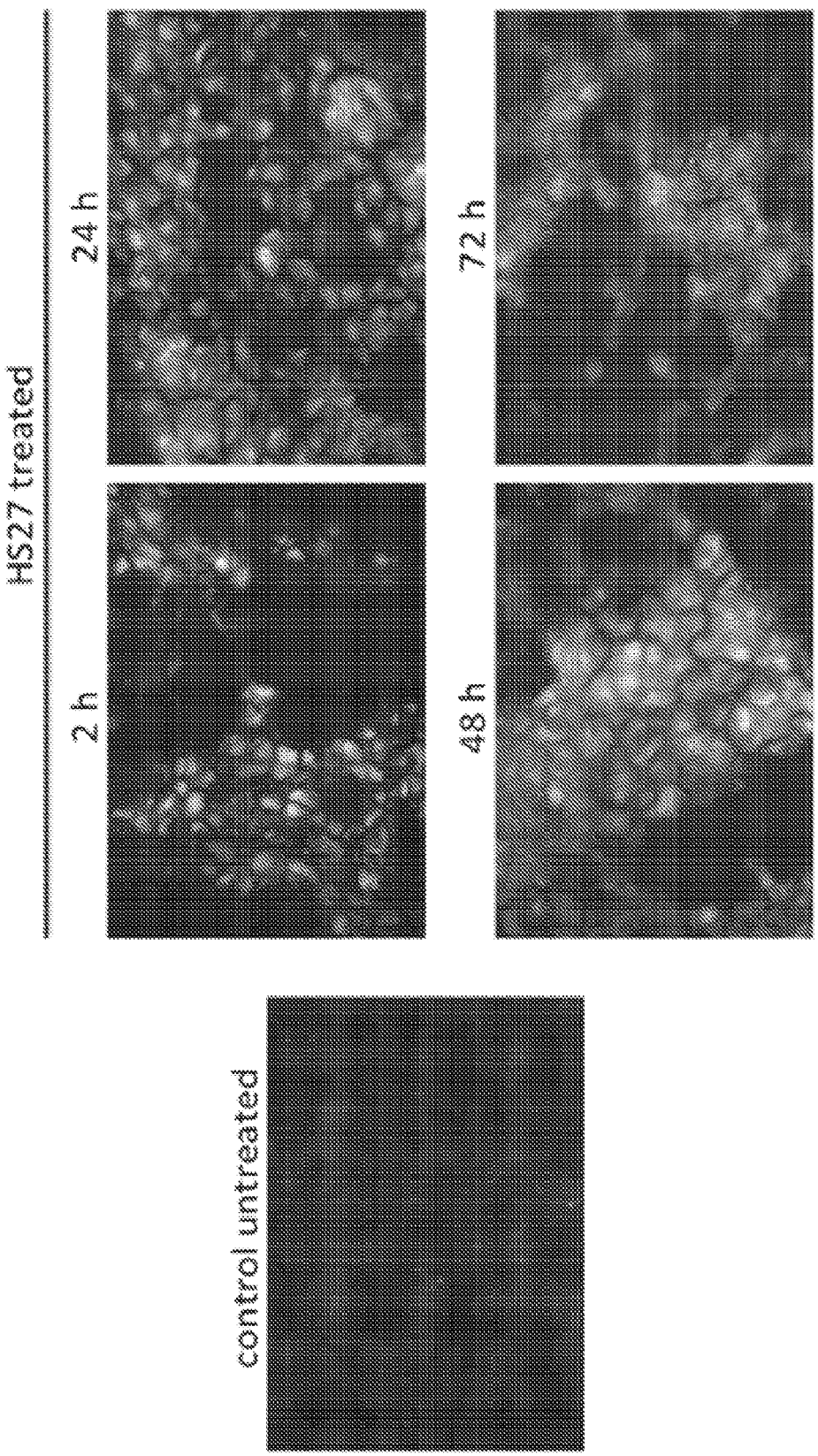
FIG. 12 shows fluorescence microscopy images of compound 10 uptake in breast cancer cells.

MDA-MB-468 tumor cells (5 M cells/mouse) were injected to the flank of NOD/SCID mice. After 3 weeks, tumor volumes reached 400-450 mm$^3$. Mice were treated/untreated with intraperitoneal injection of compound 10 (1 mg/mouse). After 2, 24, 48 and 72 hours, mice were sacrificed, and tumor tissues were frozen in OCT compound. FITC(+) cells in tumor tissues (frozen sections) were analyzed under fluorescent microscope (Axio Observer). From 2 to 48 h, tumor cells showed intense FITC signal, as shown in FIG. 12. In FIG. 12, the green staining from compound 10 fluorescence appears white or light gray.

Example 18. Recovery of Compound 10 Bound to Hsp90 In Vitro and In Vivo

Figure 13A:
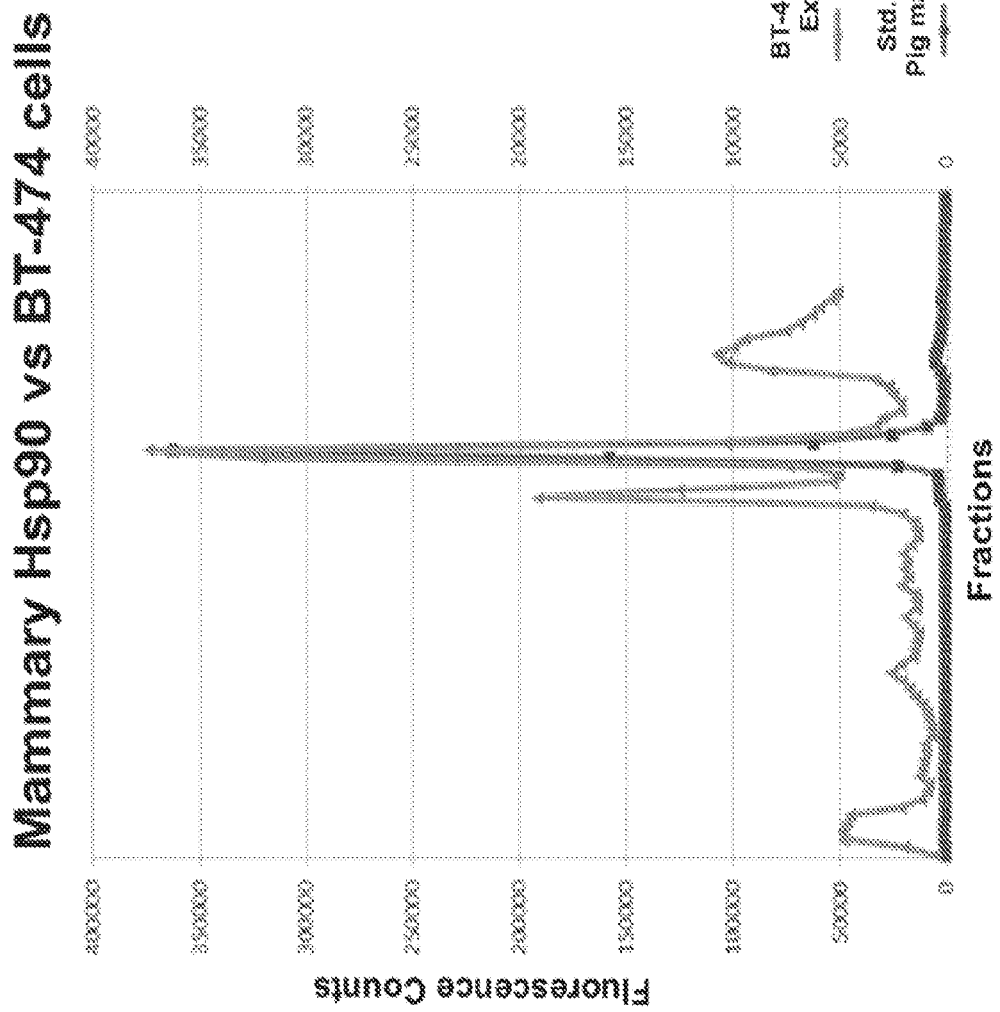
FIG. 13 shows chromatograms of Hsp90 purified from: (A) pig mammary gland and BT474 cells, and (B) MCF7 cells, treated with compound 10.

Hsp90 was purified from pig mammary gland as described in Hughes et al., *Bioorg Med Chem.* 2012, 20(10): 3298-3305. The purified protein (0.3 µg) was mixed with an excess of compound 10. The unbound probe was removed by dialysis and the labeled protein subjected to microanion exchange chromatography using a Pharmacia SMART system. Column fractions (100 µL) were collected and analyzed for fluorescence in a plate reader. Chromatographs are shown in FIG. 13A, showing a single peak was recovered by fluorescence that correlated with elution of Hsp90 as determined by Western blot and mass spectrometry. The chromatography experiment was then repeated on cell extracts prepared from MCF7 and BT474 cells treated with compound 10. In both cases a peak of fluorescence was recovered at 49 minutes that co-elutes with Hsp90.

Figure 13B:
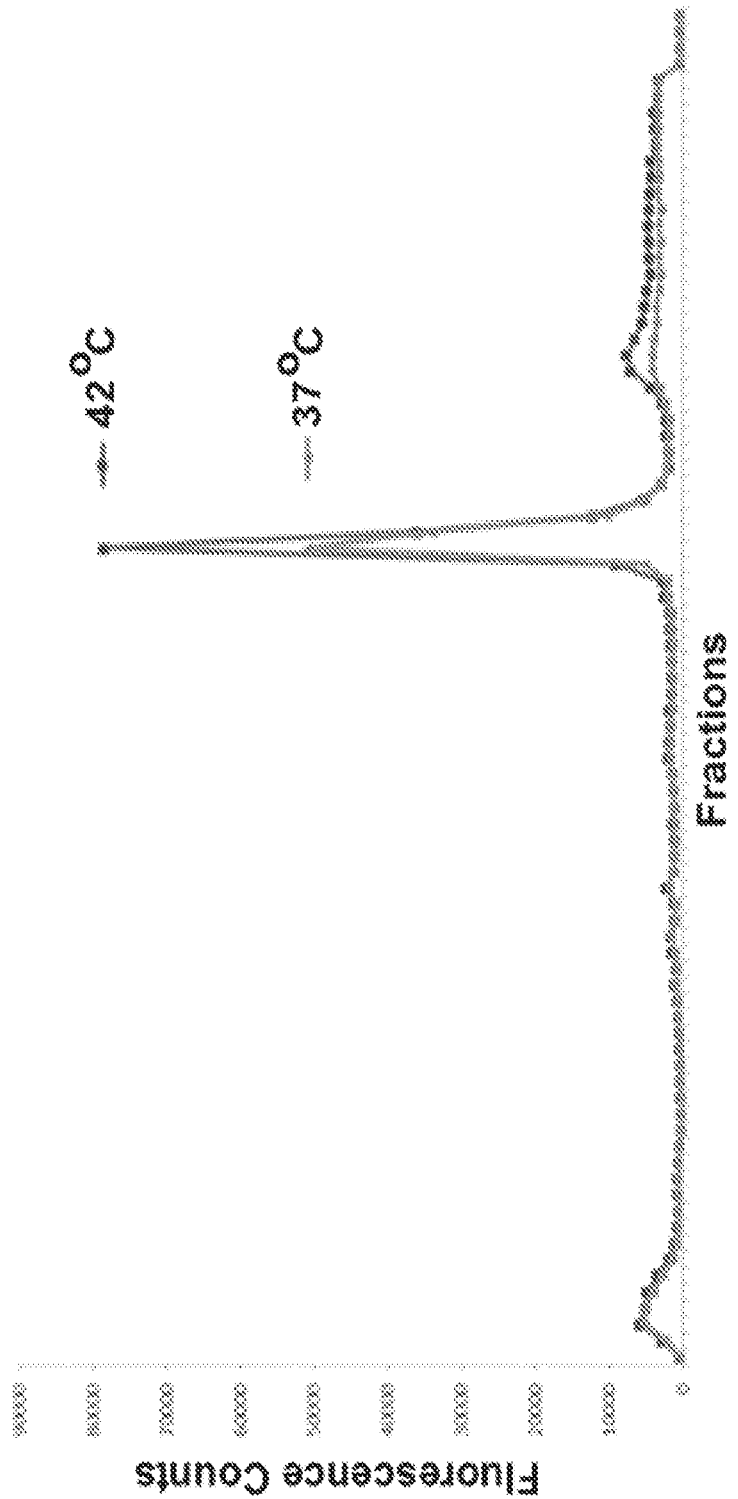

MCF cells were heated to 42° C. or maintained at 37° C. for 60 minutes. Compound 10 was added (10 µM) and after 60 minutes the cells harvested. Extracts were prepared and separated by micro anion-exchange chromatography. Column fractions were analyzed for the presence of compound 10. FIG. 13B shows that the major peak of fluorescence correlates with elution of Hsp90 and that heat treatment induces activation of the protein as reflected by increased uptake of compound 10.

Collectively these data demonstrate that compound 10 binds to Hsp90 in tumor cells and is not associated with any other cellular protein, and that the probe can be recovered bound to the protein from cell extracts.

Example 19. Imaging of HSP90 Expression in Mouse Xenografts by Fluorescence Imaging Mice with MDA MB 468 xenografts were injected with either 0.1, 0.5 or 1 mg of compound 10 intravenously. The animals were then immediately imaged in real time in an IVIS Kinetic imager (Caliper Life Science) for the presence of fluorescence at 465ex/520em. After two hours the tumors were excised and examined for the presence of compound 10.

Figure 14A:
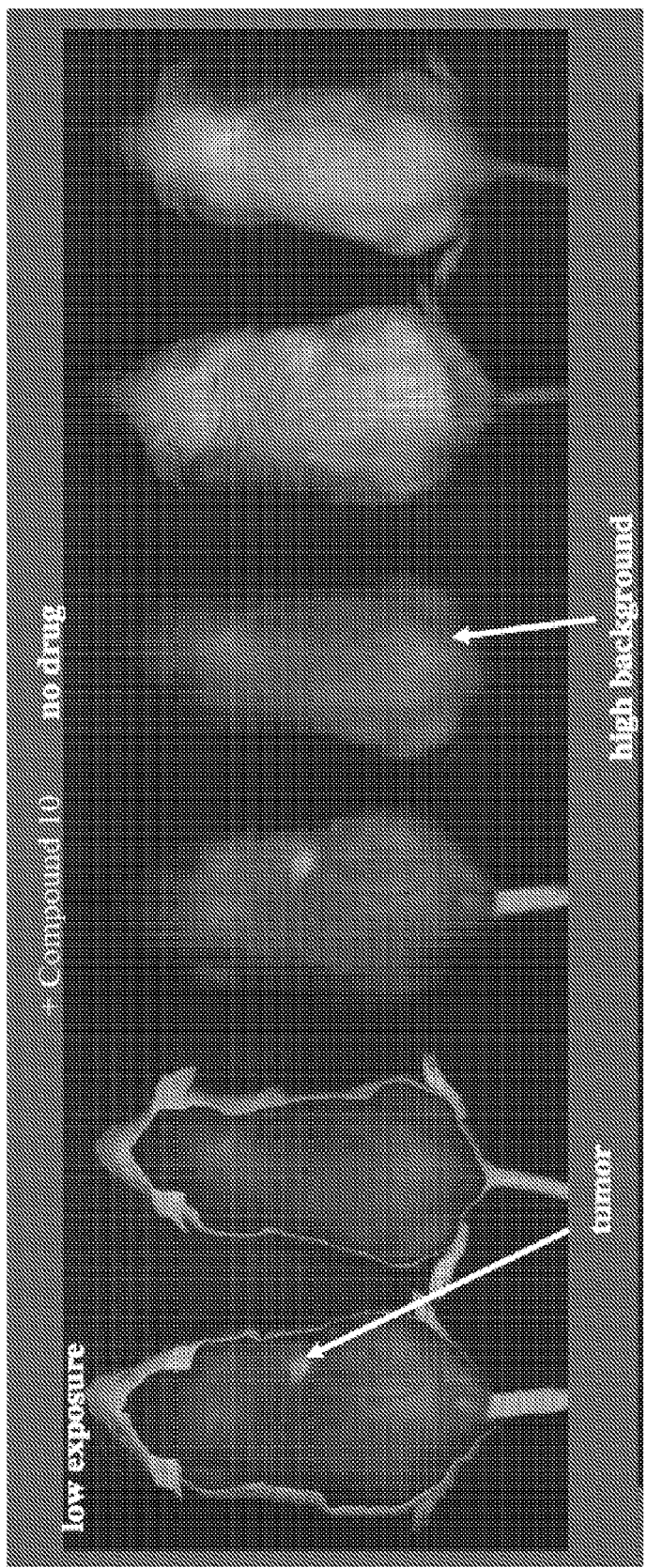
FIG. 14 shows: (A) Fluorescence images of HSP90 expression in mouse xenografts; (B) quantitative analysis of compound 10 accumulation in tumors isolated from mice; and (C) accumulation of compound 12 within tumors isolated from mice.

FIG. 14A shows rapid accumulation of compound 10 in the xenograft following tail vein injection. Red image (false, 1 vs. 2) clearly demarks the tumor over background signal (appearing very dark gray in FIG. 14A). Green image (actual, 3 vs. 4) shows clear demarcation of the tumor over and above the natural background fluorescence of the animal (with the tumor appearing bright white and background fluorescence appearing gray).

Figure 14B:
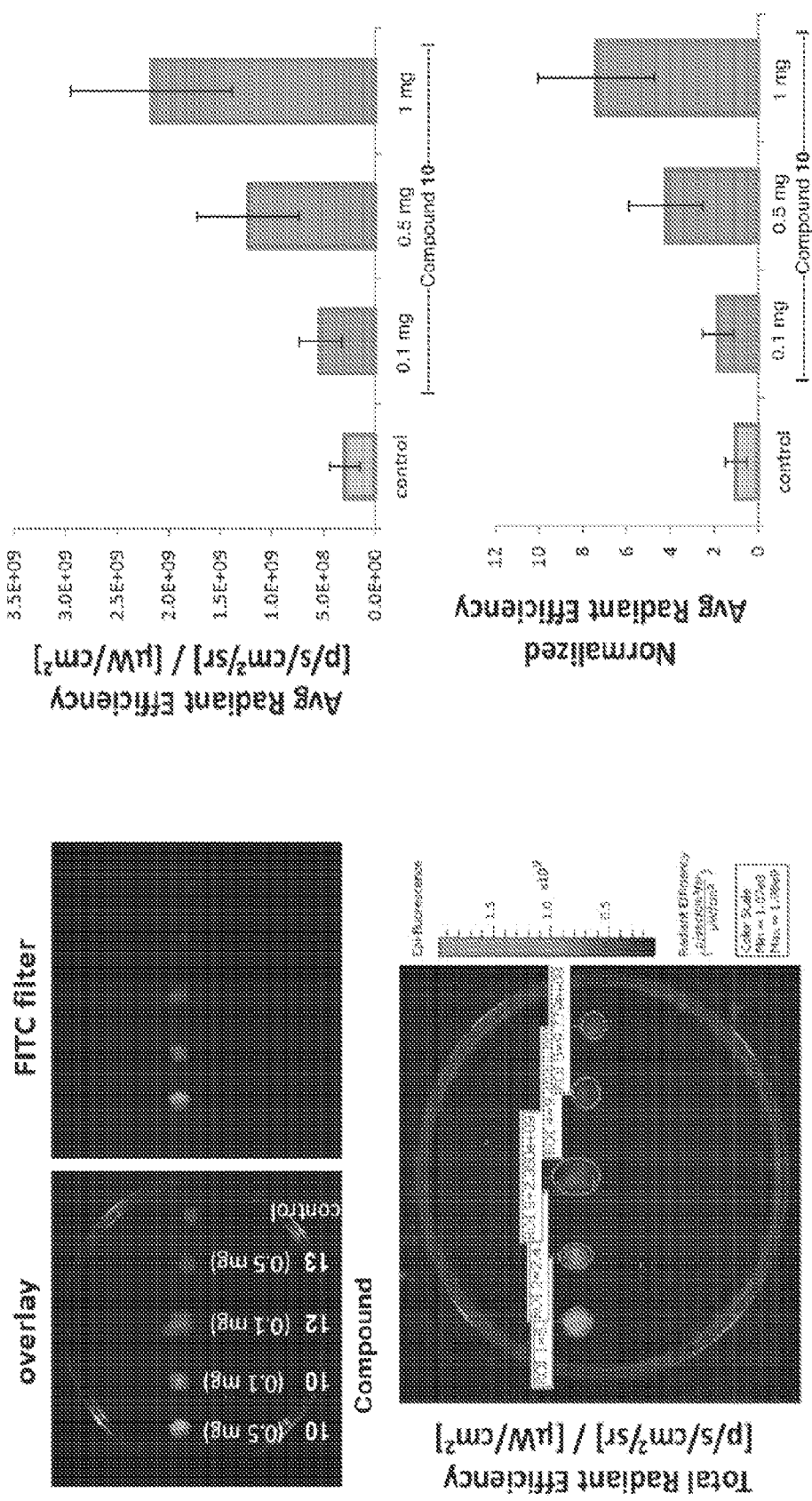

FIG. 14B shows quantitative analysis of compound 10 accumulation in tumors isolated from mice treated with the indicated doses of the compound. FIG. 14B shows the probe accumulates selectively within the tumor mass in a dose dependent manner. Measurements were made in the IVIS imager or by preparing cells extracts from the tumors and measuring their fluorescence in a microtitre plate reader.

Figure 14C:
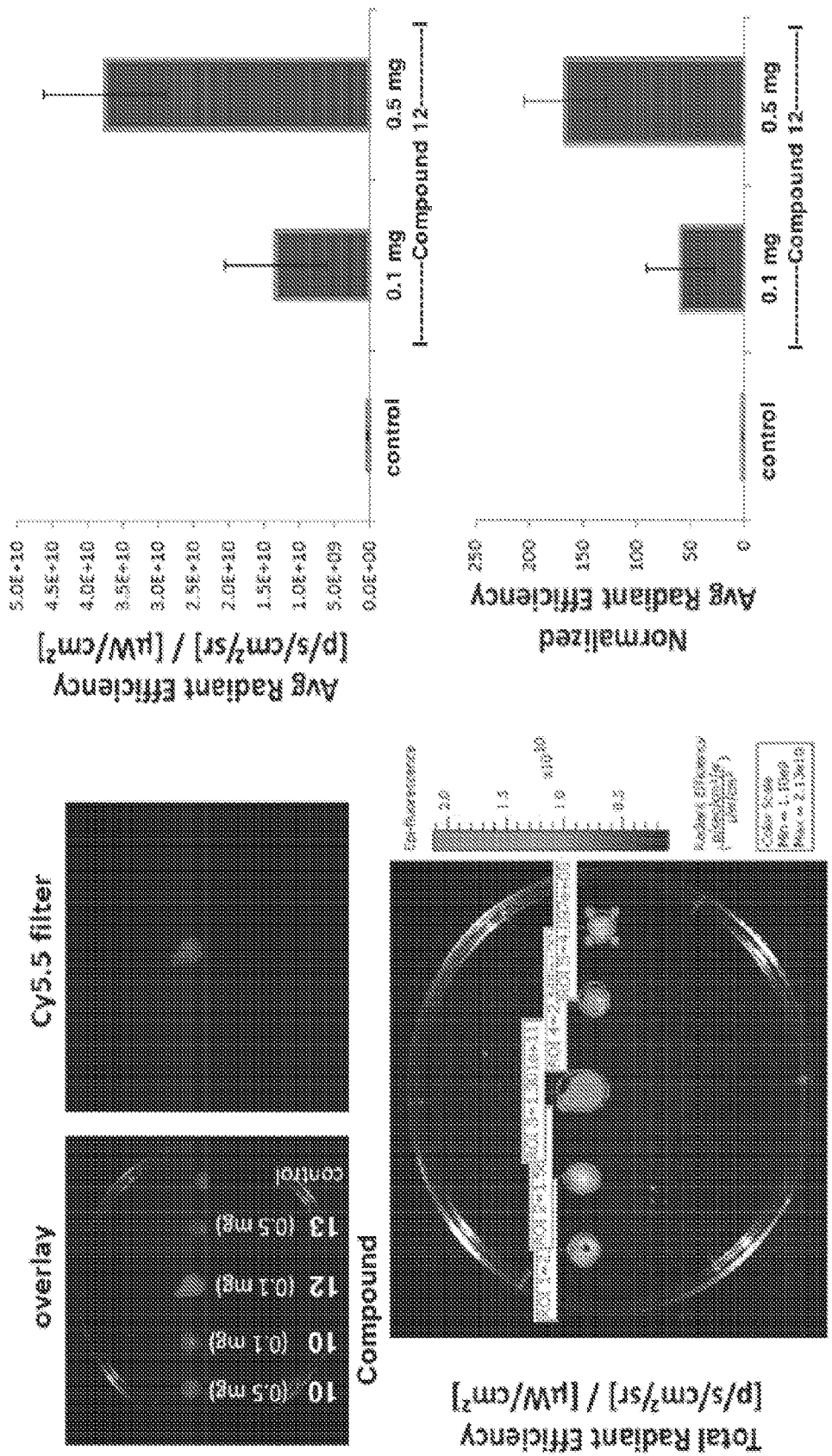

FIG. 14C shows accumulation of compound 12 within tumors isolated from mice injected with the indicated concentrations of the compound. FIG. 14C shows the probe accumulates selectively within the tumor mass in a dose dependent manner. Measurements were made in the IVIS imager or by preparing cells extracts from the tumors and measuring their fluorescence in a microtitre plate reader.

Example 20. In Vivo Detection of Compound 10 with Optical Spectroscopy

MDA-MB-468 tumor cells (1 M cells/mouse) were injected to the flank of SCID mice. Three weeks later, when tumor size reached 5-8 mm in diameter, the experiment was performed. Baseline autofluorescence levels were measured for tumor and normal tissues (skin adjacent to tumor). 1 mg or 0.5 mg of compound 10 was injected via tail vein. After drug injection, fluorescence signals were measured with the optical spectroscopy (~30 min) Two days after injection, measurement of fluorescence signal was repeated.

Figure 15:
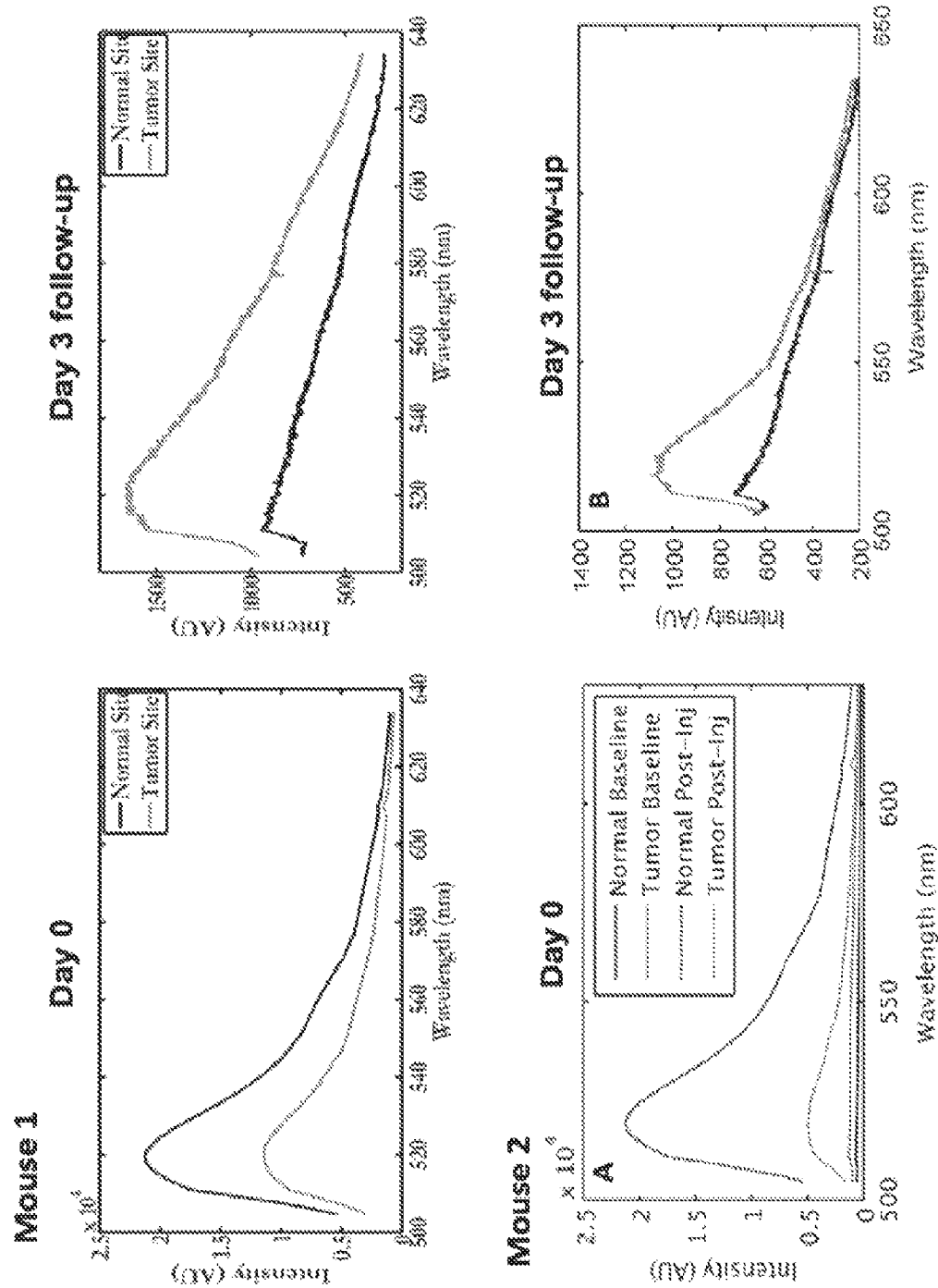
FIG. 15 shows in vivo detection of compound 10 with optical spectroscopy.

FIG. 15 shows results from two separate mice injected with compound 10 (1 mg) and the presence of the compound detected tumor by optical spectroscopy at time 0 and then 3 days later. Normal: Normal skin adjacent to tumor. All data are normalized to peak fluorescence intensity to compare fluorescence line shapes. In both mice at Day 0 Normal shows higher signal than tumor after compound 10 injection (due to poor vasculature in tumor). Measurements were made within a few minutes of injection. On Day 3, normal site has declined to pre-injection baseline level whereas the tumor still retains FITC signal in both cases. These data again demonstrate accumulation of compound 10 in tumors only and not other tissues.

Example 21. Compound 10 Recognizes Cells Infected with HIV-1

TZM-bl (Hela derived) cells were added on glass coverslips in 24-well plates (1×105 cells/well) and were allowed to attach to cover slips overnight. For infection NL4.3 virus (HIV-1) was added to medium to achieve 10 ng/mL P24 protein concentration along with DEAE dextran at a final concentration 15 µg/mL. After 48 hours of infection, compound 10 was added to the medium and incubated for 1 hour at 37° C. Later the infected cells were washed twice with phosphate-buffered saline (PBS) and fixed for 20 min in 4% paraformaldehyde. They were washed twice with PBS and permeabilized for 30 min in 50% ice cold methanol on ice. Blocking was carried out using 1% FBS for 30 minutes at room temperature after two washes with PBS. Cells were then incubated for 2 hours at room temperature with antibody against HIV-1 capsid protein P24 at 1:100 dilutions in PBS. The antibody was obtained from the AIDS Reference and Reagent Program (HIV-1 p24 Monoclonal Antibody-183-H12-5C, Catalogue number: 3537). The cells were washed three times in PBS before and after 1 h of incubation with anti-mouse Texas Red secondary antibody (1:250). (Texas Red® Goat Anti-Mouse IgG (H+L), catalogue number: T682, Life technologies). Cover slips were mounted on the slides using Prolong gold with DAPI (ProLong® Gold Antifade Reagent with DAPI Catalog Number P36935, life technologies) and observed by confocal microscopy (Fluoview FV10i Olympus).

Figure 16:
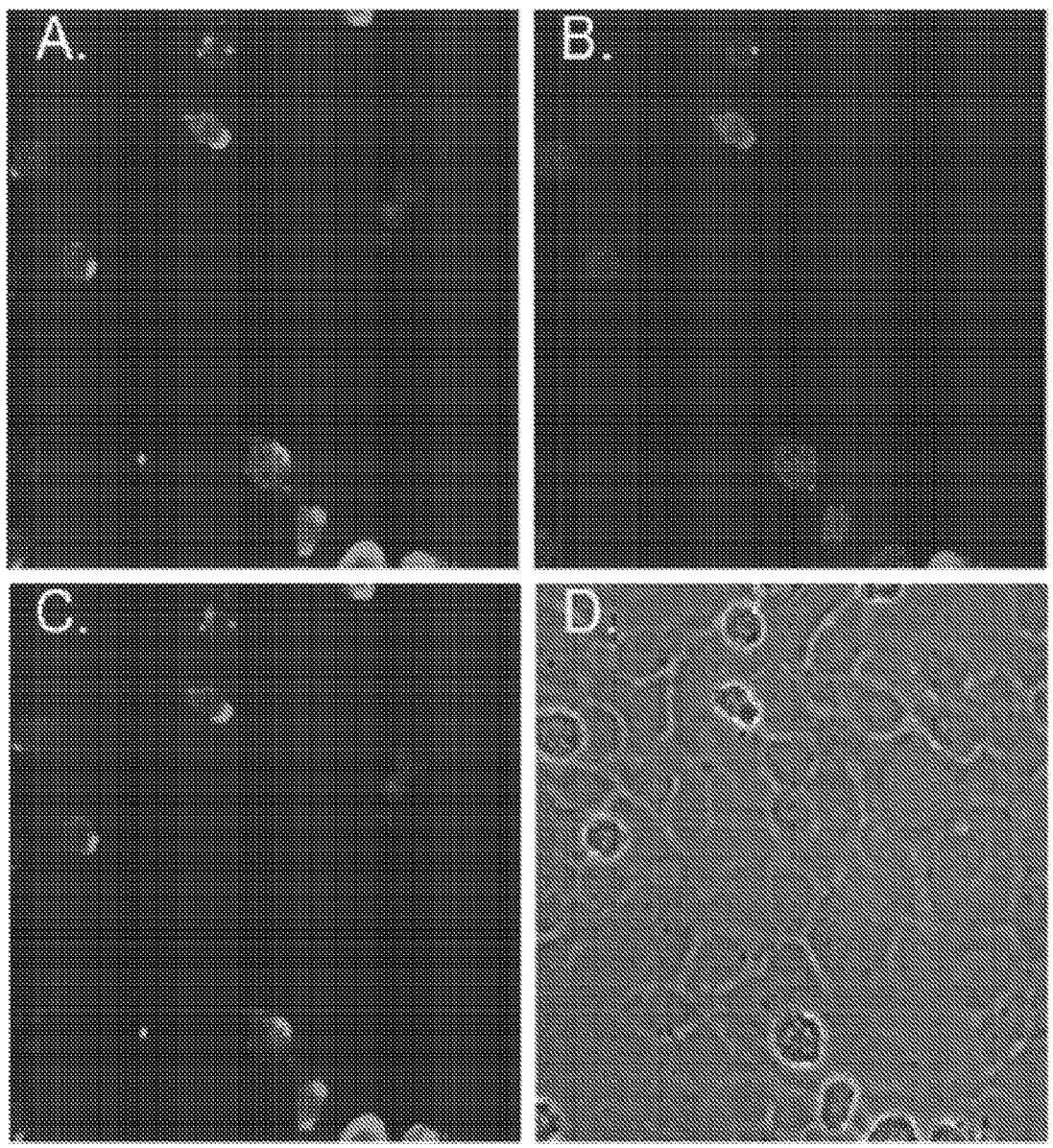
FIG. 16 shows images of cells infected with human immunodeficiency virus, treated with compound 10 and an HIV-specific antibody.

As shown in FIG. 16, panel A is an overlay of B and C; panel B shows the fluorescence from compound 10 (where green staining appears white or light gray); panel C shows fluorescence from the antibody to SP4 viral capsid protein (where red staining appears white or light gray); D shows an optical image of the entire field, showing that the probe and antibody do not recognize uninfected cells. These data demonstrate that compound 10 can be used to detect cells infected with HIV.

Example 22. Recovery of Drug-Bound Protein from Mice

Figure 17:
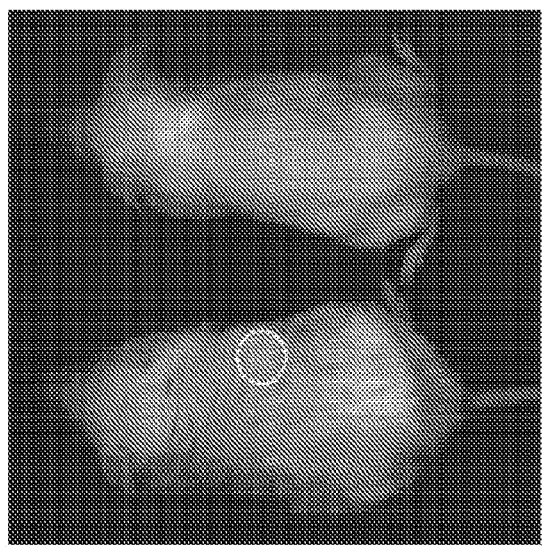
FIG. 17 shows recovery of compound 10-bound protein from mice.
Figure 17:
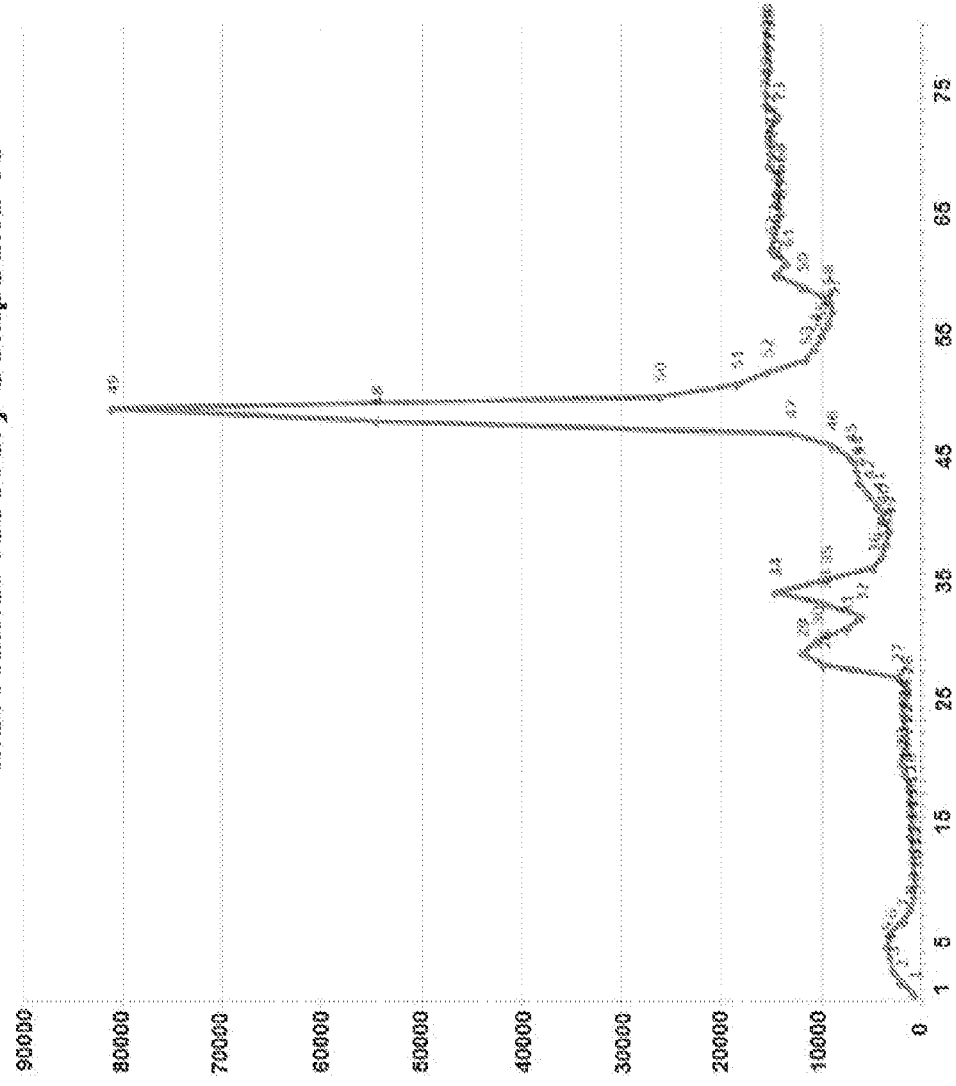

Mice were injected (IV) with 1 mg of compound 10 and the tumors were excised from the animal after 2 hours. Tissue extracts were prepared and characterized by micro anion-exchange chromatography. Column fractions were analyzed for the presence of compound 10 by fluorescence and mass spectrometry. Results are shown in FIG. 17. The major peak of fluorescence (fractions 49-53) correlates with elution of full length Hsp90. The two minor peaks (fractions 27-35) were attributable to binding to degraded forms of the N terminal domain of Hsp90.

Example 23. Synthesis of Iodine-Containing Compounds

N-(19-((2-carbamoyl-5-(3,6,6-trimethyl-4-oxo-4,5,6,7-tetrahydro-1H-indazol-1-yl)phenyl)amino)-4,7,10,13,16-pentaoxanonadecyl)-3-iodobenzamide (30)

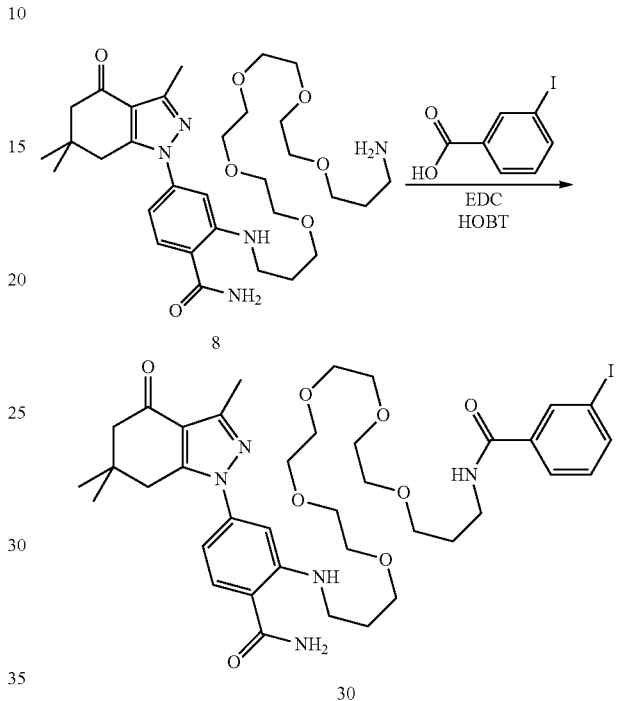

Amine (8) (165 mg, 273 umol), 3-iodobenzoic acid (68 mg, 273 umol), EDC (79 mg, 410 umol) and HOBT (37 mg, 227 umol) and were dissolved in methylene chloride (4 mL) and stirred at room temperature for 1 day. The reaction mixture was concentrated then dissolved in DMSO (1.5 mL) and purified by prep HPLC (30 to 100% methanol, 20 mL/m, Agilent C-18, 21.1×25 cm) to give 30 (155.7 mg, 68%) as a clear glass. MS (ESI): m/z 834.3 [M+H]$^+$.

N-(19-((2-carbamoyl-5-(3,6,6-trimethyl-4-oxo-4,5,6,7-tetrahydro-1H-indazol-1-yl)phenyl)amino)-4,7,10,13,16-pentaoxanonadecyl)-3-(trimethylstannyl)benzamide (31)

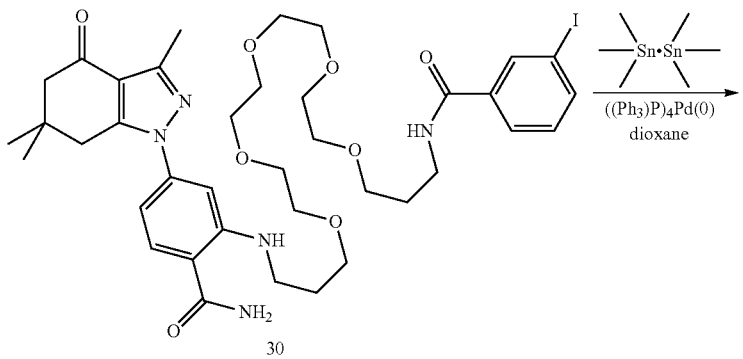

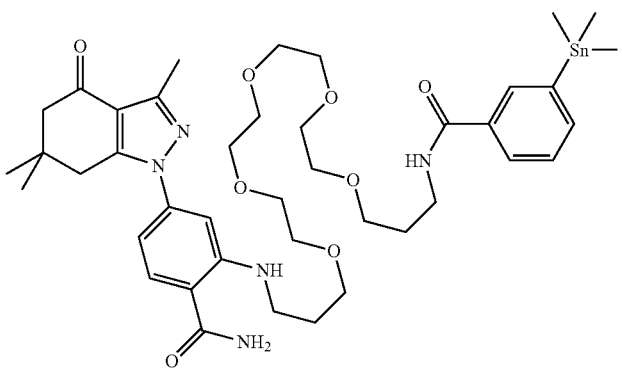

31

From *J. Org. Chem.* 2012, 77, 1931-1938 and *Appl. Radiat. Isot.* Vol. 49, No. 8, pp. 955-959, 1998. Iodide (30) (92.7 mg, 111 umol), hexamethylditin (40 mg, 122 umol) and tetrakis triphenylphosphine palladium(0) (2.6 mg 2.22 umol) were slurried in dioxane (2 mL), purged with nitrogen and heated to 100° C. for 1 h then 80° C. for 16 h. The reaction mixture was concentrated and chromatographed (silica gel, 2.5×25, $CH_2Cl_2$ (100 mL), $CH_2Cl_2$/MeOH: 19/1 (250 mL), $CH_2Cl_2$/MeOH: 9/1 (250 mL)) to give 31 (92 mg, 95%) as a slightly yellowish oil. The product was further purified by prep HPLC (30 to 100% methanol, 20 mL/m, Agilent C-18, 21.1×25 cm) to give a clear glass. MS (ESI): base peak m/z 872.4 [M+H]+.

Development of Method for Iodine Incorporation from $I_2$

Tin compound 31 (15.4 mg, 17.7 umol) was dissolved in methanol (1 mL) and treated with 1N NaOH (53 uL of 1N solution) followed by Iodine (194 uL of 0.1 M solution). The iodine color went away almost immediately. After stirring for 20 m, an aliquot was removed for LC/MS analysis. LC/MS shows clean conversion to the iodide, about 60% there. Additional iodine (194 uL) was added to test for over iodination. After a day, LC/MS showed complete and clean conversion to the mono-iodo compound 30. MS (ESI): m/z 834.3 [M+H]+.

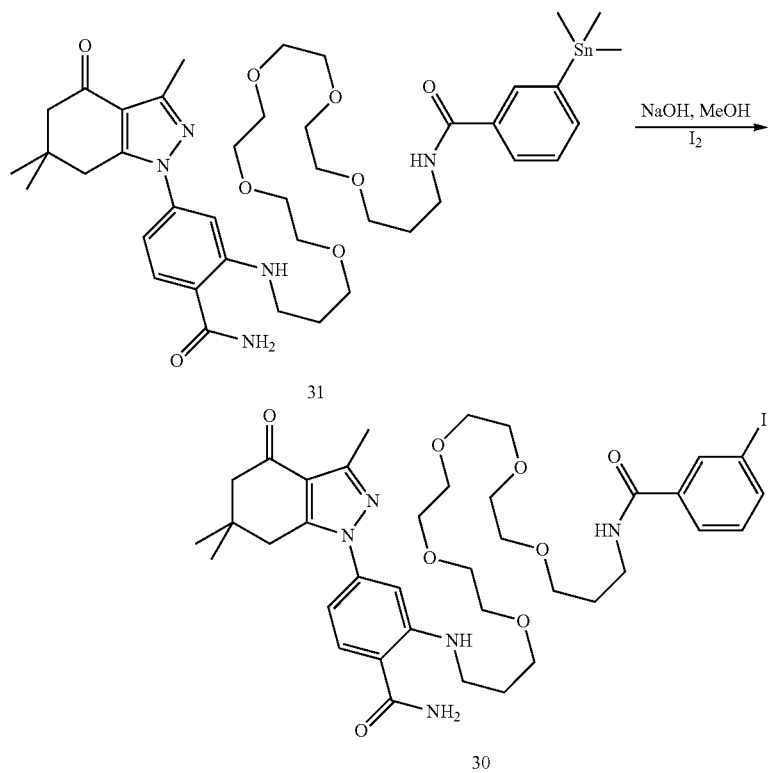

Example 24. Synthesis of Dual-Function Compounds 2-((1-(3-iodophenyl)-6,9,12,15,18-pentaoxa-2-azahenicosan-21-yl)amino)-4-(3,6,6-trimethyl-4-oxo-4,5,6,7-tetrahydro-1H-indazol-1-yl)benzamide (32)

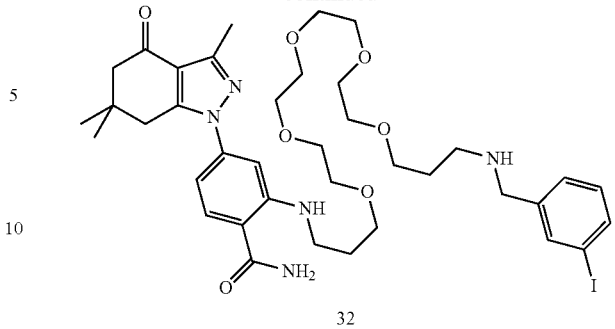

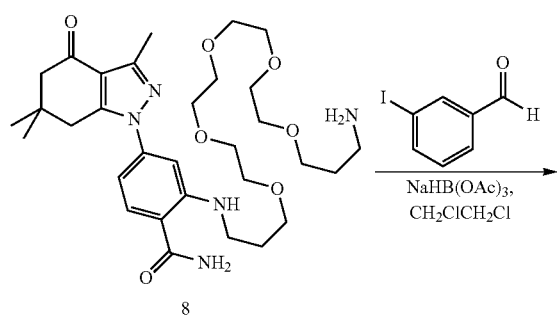

Amine 8 (100 mg, 166 umol) and 3-iodobenzaldehyde (38 mg, 166 umol) were dissolved in dichloroethane (2 mL) and treated with sodium triacetoxyborohydride (60 mg, 282 umol) and stirred at room temperature for 16 h. The sample was then loaded onto a column and chromatographed (silica gel, 2.5×15 cm, CH$_2$Cl$_2$ (100 mL), then 19/0.9/0.1: CH$_2$Cl$_2$/MeOH/NH$_3$ (200 mL), then 9/0.9/0.1: CH$_2$Cl$_2$/MeOH/NH$_3$ (450 mL)) to give 32 (108 mg, 63%) as a clear oil. MS (ESI): m/z 820.3 [M+H]$^+$.

4-(3,6,6-trimethyl-4-oxo-4,5,6,7-tetrahydro-1H-indazol-1-yl)-2-((1-(3-(trimethylstannyl)phenyl)-6,9,12,15,18-pentaoxa-2-azahenicosan-21-yl)amino)benzamide (33)

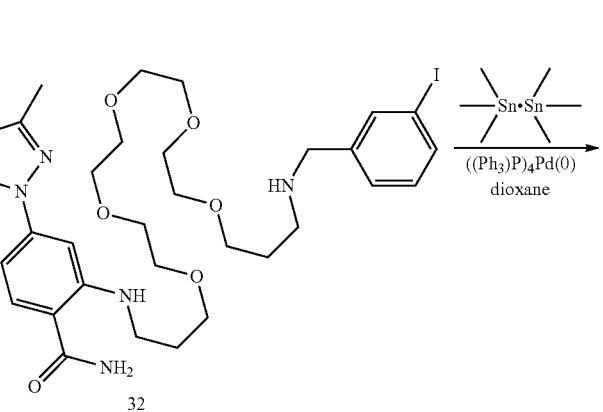

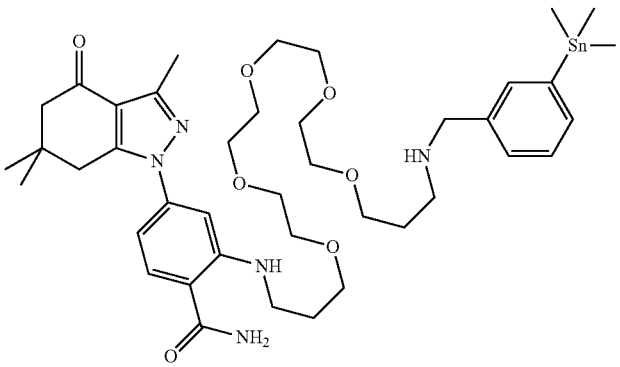

Iodide 32 (230 mg, 280 umol), hexamethylditin (101 mg, 308 umol) and tetrakis triphenylphosphine palladium(0) (6.48 mg 5.61 umol) were slurried in dioxane (5 mL), purged with nitrogen and heated to 100° C. for 45 m. The reaction mixture was concentrated then added to a column and chromatographed (silica gel, 2.5×25, CH$_2$Cl$_2$ (100 mL), CH$_2$Cl$_2$/MeOH/NH$_3$: 19/0.9/0.1 (250 mL), CH$_2$Cl$_2$/MeOH/NH$_3$: 9/0.9/0.1 (500 mL)) to give 33 (213 mg, 89%) as a dark glass. MS (ESI): base peak m/z 858.4 [M+H]$^+$.

2-((1-(((3',6'-dihydroxy-3-oxo-3H-spiro[isobenzofuran-1,9'-xanthen]-5-yl)amino)-1-thioxo-2-(3-(trimethylstannyl)benzyl)-6,9,12,15,18-pentaoxa-2-azahenicosan-21-yl)amino)-4-(3,6,6-trimethyl-4-oxo-4,5,6,7-tetrahydro-1H-indazol-1-yl)benzamide (34)

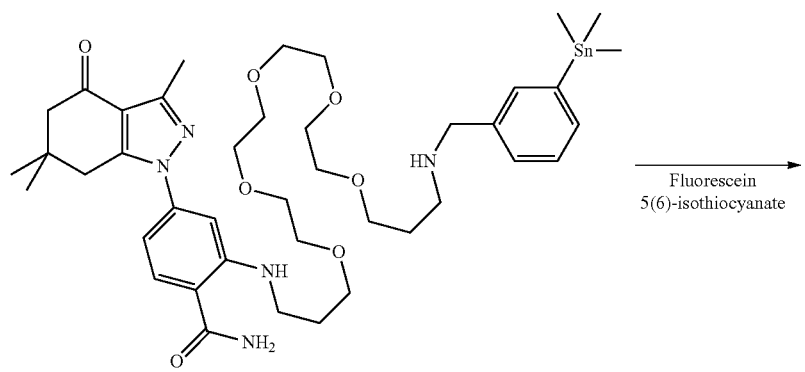

33

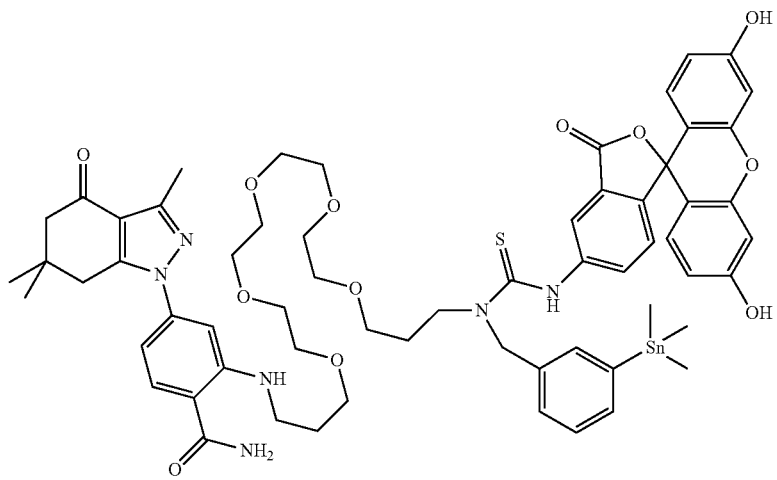

34

Tin compound 33 (116 mg, 135 umol) was dissolved in DMSO (200 uL) and treated with FITC (53 mg, 135 umol) dissolved in DMSO (200 uL) followed by Hunig's base (around 35 mg, 270 umol). The mixture was purified by prep HPLC (30 to 100% methanol, 20 mL/m, Agilent C-18, 21.1×25 cm) to give 34 (68 mg, 40%) as a yellow solid. MS (ESI): base peak m/z 1247.4 [M]$^-$.

Synthesis of Iodide Standard: 2-((1-((3',6'-dihydroxy-3-oxo-3H-spiro[isobenzofuran-1,9'-xanthen]-5-yl)amino)-2-(3-iodobenzyl)-1-thioxo-6,9,12,15,18-pentaoxa-2-azahenicosan-21-yl)amino)-4-(3,6,6-trimethyl-4-oxo-4,5,6,7-tetrahydro-1H-indazol-1-yl)benzamide (35)

Iodide 32 (31 mg, 38 umol) was dissolved in DMSO (200 uL) and treated with FITC (15 mg, 38 umol) dissolved in DMSO (200 uL) and Hunig's base (10 mg, 76 umol) and stirred for 1 h. The sample was then loaded onto a column and chromatographed (2.5×15 cm, $CH_2Cl_2$ (100 mL), then 19/1/0.1: $CH_2Cl_2$/MeOH/AcOH (1500 mL), then 9/1/0.1: $CH_2Cl_2$/MeOH/AcOH (1500 mL)) to give 35 (28 mg, 62%) as a yellow glass. MS (ESI): m/z 1207.4 [M]⁻.

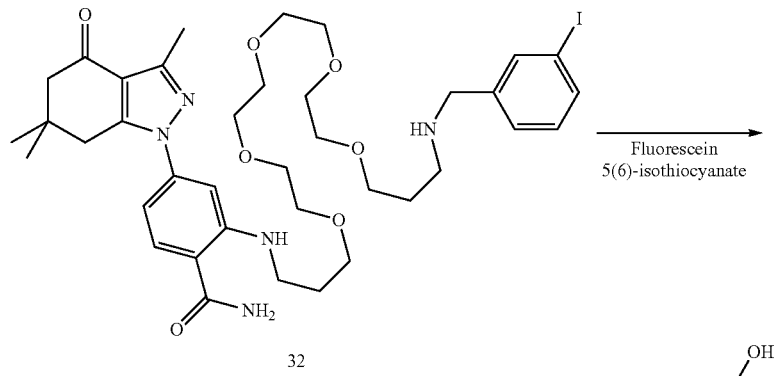

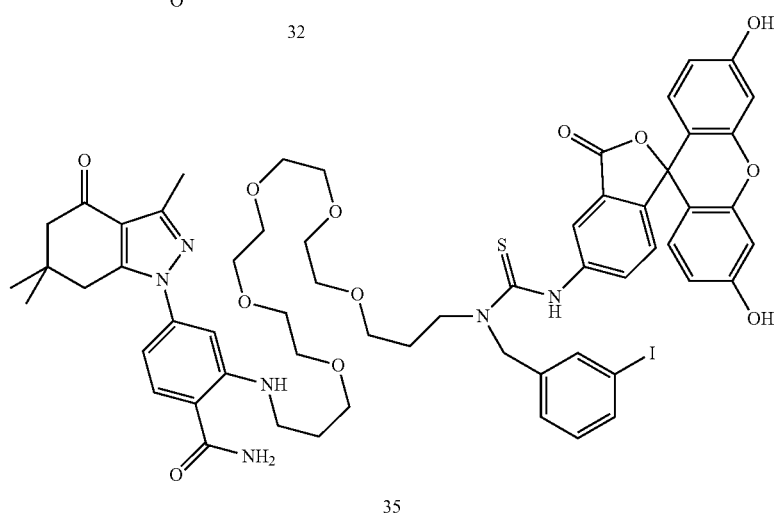

Iodination Test

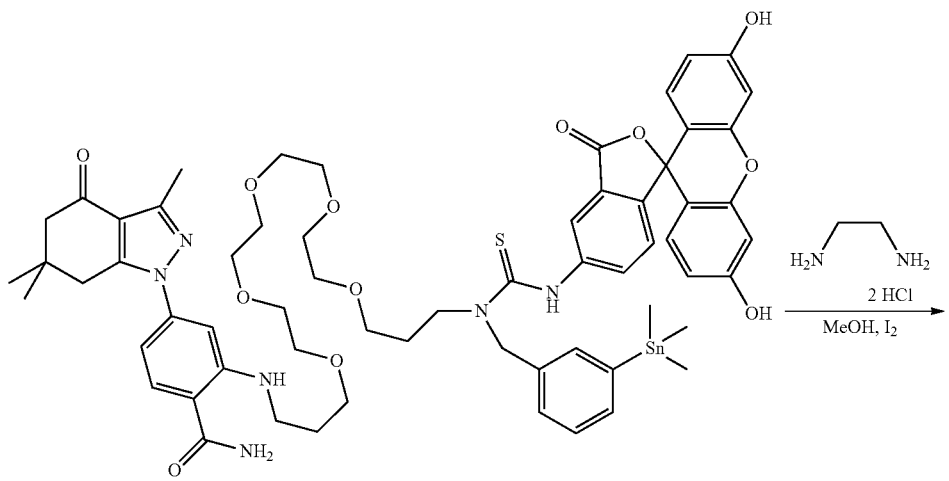

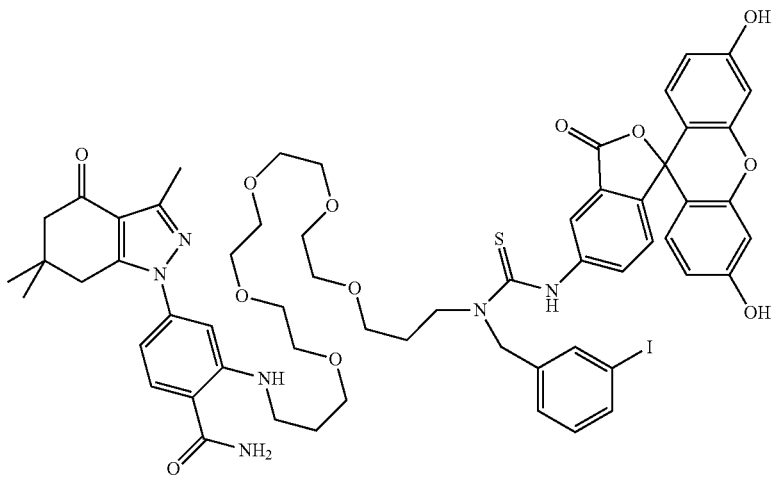

35

Tin compound 34 (1 mg, 0.8 umol) was dissolved in methanol (1 mL) and treated with ethylenediamine diHCl (1 mg in 10 uL of water) followed by iodine (8 uL of 0.1 M solution). The color dissipated instantly. After stirring for 1 day, LC/MS showed clean formation of the iodide. MS (ESI): m/z 1207.4 [M]⁻.

The iodination can be repeated using a radiolabelled iodine source to provide a dual function compound.

The invention claimed is:

1. A compound of formula (I):

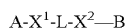

A-X$^1$-L-X$^2$—B    (I)

wherein:

A is a heat shock protein 90 binding component;

X$^1$ is selected from the group consisting of —NH—, —O—, —S—, —C(O)— and —S(O)$_2$—;

X$^2$ is selected from the group consisting of —NR—, —O—, —S—, —C(O)— and —S(O)$_2$—;

L is a divalent linker of the following formula:

—(CH$_2$)$_m$—(OCH$_2$CH$_2$)$_n$—O—(CH$_2$)$_p$— wherein:

m is 2 or 3;

n is 4, 5, 6, 7, 8, 9, 10, 11, 12, 13, 14, 15, 16, 17, 18, 19 or 20; and p is 2 or 3;

B is selected from the group consisting of a detection moiety, an anti-cancer agent, and a heat shock protein 90 binding component; and R is selected from the group consisting of —H and a detection moiety;

wherein each heat shock protein 90 binding component independently has the following formula (II):

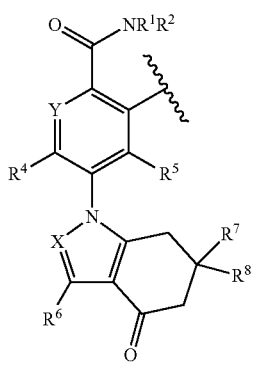

wherein:

R$^1$ and R$^2$ are independently selected from the group consisting of —H and —C$_{1-8}$-alkyl;

Y is CR$^3$ or N;

R$^3$ is —H, —F or —OCH$_3$;

R$^4$ and R$^5$ are independently selected from the group consisting of —H, —F and —OCH$_3$;

R$^6$ is —C$_{1-8}$-alkyl, —C$_{2-8}$-alkenyl, —C$_{2-8}$-alkynyl, —C$_{3-8}$-cycloalkenyl, —C$_{3-8}$-cycloalkenyl-C$_{1-8}$-alkyl, —C$_{3-8}$-cycloalkyl, —C$_{3-8}$-cycloalkyl-C$_{1-8}$-alkyl, aryl, aryl-C$_{1-8}$-alkyl, halo-C$_{1-8}$-alkyl, heteroaryl, heteroaryl-C$_{1-8}$-alkyl, heterocyclyl, heterocyclyl-C$_{1-8}$-alkyl, or hydroxy-C$_{1-8}$-alkyl;

R$^7$ and R$^8$ are independently selected from the group consisting of —H and —C$_{1-8}$-alkyl;

X is N;

and

represents the point of attachment in formula (I);

wherein each detection moiety independently comprises a fluorophore or a radioactive compound;

wherein the fluorophore is a fluorescein, a rhodamine, a coumarin, a cyanine, or a boron-dipyrromethene;
wherein the radioactive compound is a radioisotope; and
wherein the anti-cancer agent is an alkylating agent, an anti-epidermal growth factor receptor antibody, an anti-Her-2 antibody, an antimetabolite, a vinca alkaloid, an anthracycline, a platinum-based agent, a topoisomerase inhibitor, a taxane, an anti-cancer antibiotic, an immune cell antibody, an interferon, an interleukin, a heat shock protein 90 inhibitor, an anti-androgen, an anti-estrogen, an antihypercalcemia agent, an apoptosis inducer, an aurora kinase inhibitor, a Bruton's tyrosine kinase inhibitor, a calcineurin inhibitor, a $Ca^{2+}$-calmodulin-dependent protein kinase II inhibitor, a CD45 tyrosine phosphatase inhibitor, a cell division cycle 25 phosphatase inhibitor, a checkpoint kinase inhibitor, a cyclooxygenase inhibitor, a cRAF kinase inhibitor, a cyclin dependent kinase inhibitor, a cysteine protease inhibitor, a deoxyribonucleic acid intercalator, a deoxyribonucleic acid strand breaker, an E3 ligase inhibitor, an epidermal growth factor pathway inhibitor, a farnesyltransferase inhibitor, a fetal liver kinase-1 inhibitor, a glycogen synthase kinase-3 inhibitor, a histone deacetylase inhibitor, an I-kappa B-alpha kinase inhibitor, an imidazotetrazinone, an insulin tyrosine kinase inhibitor, a c-Jun N-terminal kinase inhibitor, a mitogen-activated protein kinase inhibitor, a mouse double minute 2 inhibitor, an MEK inhibitor, a matrix metalloproteinase inhibitor, a mammalian target of rapamycin inhibitor, a nerve growth factor receptor tyrosine kinase inhibitor, a p38 mitogen-activated protein kinase inhibitor, a p56 tyrosine kinase inhibitor, a platelet-derived growth factor pathway inhibitor, a phosphatidylinositol 3-kinase inhibitor, a phosphatase inhibitor, a protein phosphatase inhibitor, a protein kinase C inhibitor, a protein kinase C delta kinase inhibitor, a polyamine synthesis inhibitor, a protein tyrosine phosphatase 1B inhibitor, a protein tyrosine kinase inhibitor, an SRC family tyrosine kinase inhibitor, a spleen tyrosine kinase inhibitor, a Janus tyrosine kinase inhibitor, a retinoid, a ribonucleic acid polymerase II elongation inhibitor, a serine/threonine kinase inhibitor, a sterol biosynthesis inhibitor, a vascular endothelial growth factor pathway inhibitor, alitretinon, altretamine, aminopterin, aminolevulinic acid, amsacrine, asparaginase, atrasentan, bexarotene, carboquone, demecolcine, efaproxiral, elsamitrucin, etoglucid, a Gliadel implant, hydroxycarbamide, leucovorin, lonidamine, lucanthone, masoprocol, methyl aminolevulinate, mitoguazone, mitotane, oblimersen, omacetaxine, pegaspargase, porfimer sodium, prednimustine, sitimagene ceradenovec, talaporfin, temoporfin, trabectedin or verteporfin.

2. The compound of claim 1, wherein A has the formula:

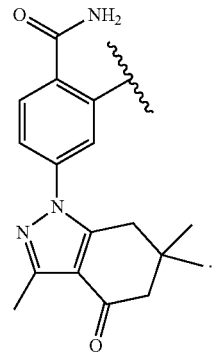

3. The compound of claim 1, wherein B is a detection moiety.

4. The compound of claim 3, wherein B is a fluorophore.

5. The compound of claim 1, wherein B is an anti-cancer agent.

6. The compound of claim 1, wherein B is a heat shock protein 90 binding component.

7. The compound of claim 1, wherein:
$R^1$ and $R^2$ are independently —H;
Y is $CR^3$;
$R^3$ is —H;
$R^4$ and $R^5$ are independently —H;
$R^6$ is —$C_{1-8}$-alkyl or halo-$C_{1-8}$-alkyl; and
$R^7$ and $R^8$ are independently —$C_{1-8}$-alkyl.

8. The compound of claim 1, wherein m is 3 and p is 3.

9. The compound of claim 1, wherein n is 4.

10. A kit comprising a compound of claim 1.

\* \* \* \* \*

UNITED STATES PATENT AND TRADEMARK OFFICE
CERTIFICATE OF CORRECTION

PATENT NO. : 9,738,643 B2
APPLICATION NO. : 14/419965
DATED : August 22, 2017
INVENTOR(S) : Timothy Haystead and Philip Floyd Hughes It is certified that error appears in the above-identified patent and that said Letters Patent is hereby corrected as shown below:

In the Specification

Column 1, Line 17:
Replace the following paragraph: [[This invention was made with U.S. Government support awarded by the National Institutes of Health, Grant Nos. 1R01-AI089526-01 and 1R01-AI090644-01. The U.S. Government has certain rights in this invention.]]

With the following paragraph: --This invention was made with government support under grant numbers 1R01-AI089526-01 and 1R01-AI090644-01 awarded by the National Institutes of Health, and grant number W81XWH-15-1-0072 awarded by the United States Army Medical Research and Materiel Command. The government has certain rights to the invention.--

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*